US011072649B2

(12) United States Patent
Hooper et al.

(10) Patent No.: US 11,072,649 B2
(45) Date of Patent: Jul. 27, 2021

(54) SYSTEMS AND METHODS FOR THE PRODUCTION OF HUMAN POLYCLONAL ANTIBODIES

(71) Applicant: SAB, LLC, Sioux Falls, SD (US)

(72) Inventors: Jay Hooper, New Market, MD (US); Eddie Sullivan, Sioux Falls, SD (US); Hua Wu, Sioux Falls, SD (US)

(73) Assignee: SAB, LLC, Sioux Falls, SD (US)

( * ) Notice: Subject to any disclaimer, the term of this patent is extended or adjusted under 35 U.S.C. 154(b) by 0 days.

(21) Appl. No.: 15/361,279

(22) Filed: Nov. 25, 2016

(65) Prior Publication Data

US 2017/0233459 A1 Aug. 17, 2017

Related U.S. Application Data

(60) Provisional application No. 62/260,023, filed on Nov. 25, 2015.

(51) Int. Cl.
| | | |
|---|---|---|
| *A61K 48/00* | (2006.01) | |
| *C12N 15/85* | (2006.01) | |
| *C07K 16/10* | (2006.01) | |
| *A61K 39/12* | (2006.01) | |
| *A61K 39/00* | (2006.01) | |

(52) U.S. Cl.
CPC .......... *C07K 16/1081* (2013.01); *A61K 39/12* (2013.01); *C07K 16/10* (2013.01); *A61K 2039/505* (2013.01); *A61K 2039/53* (2013.01); *A61K 2039/54* (2013.01); *A61K 2039/545* (2013.01); *A61K 2039/575* (2013.01); *C07K 2317/10* (2013.01); *C07K 2317/21* (2013.01); *C07K 2317/76* (2013.01); *C12N 2760/12134* (2013.01); *C12N 2760/14134* (2013.01); *C12N 2770/24134* (2013.01); *C12N 2770/36134* (2013.01)

(58) Field of Classification Search
None
See application file for complete search history.

(56) References Cited

U.S. PATENT DOCUMENTS

| | | | |
|---|---|---|---|
| 7,074,983 B2 | 7/2006 | Robl et al. | |
| 7,253,334 B2 | 8/2007 | Collas et al. | |
| 7,491,867 B2 | 2/2009 | Robl et al. | |
| 7,652,192 B2 | 1/2010 | Forsberg et al. | |
| 7,803,981 B2 * | 9/2010 | Robl ................... | A01K 67/0273 435/325 |
| 7,928,285 B2 | 4/2011 | Robl et al. | |
| 9,315,824 B2 | 4/2016 | Kuroiwa et al. | |
| 9,775,332 B2 | 10/2017 | Kuroiwa et al. | |
| 9,902,970 B2 | 2/2018 | Kuroiwa et al. | |
| 2015/0211020 A1 * | 7/2015 | Kuroiwa ............ | A01K 67/0278 800/6 |

OTHER PUBLICATIONS

Hooper et al DNA vaccine-derived human IgG produced in transchromosomal bovines protect in lethal models of hantavirus pulmonary syndrome Science translational medicine, (Nov. 26, 2014) vol. 6, No. 264, p. 264ra162 pp. 1-9.*
Hooper et al A novel Sin Nombre virus DNA vaccine and its inclusion in a candidate pan-hantavirus vaccine against hantavirus pulmonary syndrome (HPS) and hemorrhagic fever with renal syndrome (HFRS) Vaccine 31 (2013) 4314-4321.*
Sano et al . 2013 Physiological level of production of antigen-specific human immunoglobulin in cloned transgeneic cattle PLOs One pp. 1-15.*
Custer et al Active and Passive Vaccination against Hantavirus Pulmonary Syndrome with Andes Virus M Genome Segment-Based DNA Vaccine Journal of Virology, Sep. 2003, p. 9894-9905.*
Qiu et al Characterization of Zaire ebolavirus glycoprotein-specific monoclonal antibodies C l i n i c a l Immunology 2011 pp. 218-227.*
Audet et al. 2014 Molecular Characterization of the Monoclonal Antibodies Composing ZMAb: A Protective Cocktail Against Ebola Virus Scientific Reports | 4 : 6881 pp. 1-8.*
Greenland et al Vaccine 25 (2007) 3731-3741 Review Chemical adjuvants for plasmid DNA vaccines.*
Subramanian GM, Cronin PW, Poley G, et al. A phase 1 study of PAmAb, a fully human monoclonal antibody against Bacillus anthracis protective antigen, in healthy volunteers. Clin Infect Dis. 2005;41 (1):12-20.*
Kummerfeldt et al., Raxibacumab: potential role in the treatment of inhalational anthrax Infection and Drug Resistance 2014:7 101-109.*
waynesword.palomar.edu/trfeb98.htm The Five Kingdoms of Life, downloaded Aug. 27, 2019; pp. 1-19.*
wikipedia.org/wiki/vertebrates, last visited Aug. 27, 2019; pp. 1-10.*
Miao et al., 2012; review; Polymerase Chain Reaction, ISBN 978-953-510612-8; Edited by Dr Patricia Hernandez-Rodriguez, pp. 255-282.*
Brevini et al., 2010, Theriogenology, vol. 74, pp. 544-550.*
Paris et al. 2010, Theriogenology, vol. 74, pp. 516-524.*
Munoz et al. 2008, Theriogenology, vol. 69, pp. 1159-1164.*
Petitte et al. 2004, Mech. of Develop., vol. 121, pp. 1159-1168.*
Lavial et al. 2010, Develop. Growth Diff., vol. 52, pp. 101-114015.*
Grant-Klein, et al., "A multiagent filovirus DNA vaccine delivered by intramuscular electroporation completely protects mice from ebola and Marburg virus challenge," Human vaccines & immunotherapeutics. 2012; 8(11):1703-6.

(Continued)

*Primary Examiner* — Maria G Leavitt
(74) *Attorney, Agent, or Firm* — McDonnell Boehnen Hulbert & Berghoff LLP

(57) ABSTRACT

Disclosed herein is a method for producing human antibodies against a pathogen comprising injecting a non-human animal with a pathogen-derived DNA vaccine in at least two locations of the animal; injecting the animal with an adjuvant in a location of the animal different from the location of the DNA vaccine location; collecting plasma from the animal after the injections; and purifying polyclonal antibody from the plasma.

13 Claims, 23 Drawing Sheets

Specification includes a Sequence Listing.

(56) References Cited

OTHER PUBLICATIONS

Van Drunen, et al., "Electroporation-based DNA transfer enhances gene expression and immune responses to DNA vaccines in cattle," Vaccine. 2008; 26(43):5503-9.

Kwilas, et al., "A hantavirus pulmonary syndrome (HPS) DNA vaccine delivered using a spring-powered jet injector elicits a potent neutralizing antibody response in rabbits and nonhuman primates," Current gene therapy. 2014; 14(3):200-10.

Bray, et al., "A mouse model for evaluation of prophylaxis and therapy of Ebola hemorrhagic fever," The Journal of infectious diseases. 1998; 178(3):651-61.

Bielory, et al., Human serum sickness: a prospective analysis of 35 patients treated with equine anti-thymocyte globulin for bone marrow failure. Medicine 67, 40-57 (1988).

Brocato, et al., A lethal disease model for hantavirus pulmonary syndrome in immunosuppressed Syrian hamsters infected with sin nombre virus. Journal of virology 88, 811-819 (2014).

Brocato, et al., DNA vaccine-generated duck polyclonal antibodies as a postexposure prophylactic to prevent hantavirus pulmonary syndrome (HPS). PloS one 7, e35996 (2012).

Casadeva II, Passive antibody administration (immediate immunity) as a specific defense against biological weapons. Emerging infectious diseases 8, 833-841 (2002).

Kummerfeldt, "Raxibacumab: potential role in the treatment of inhalational anthrax." Infect Drug Resist 29, 101-109 (2014).

Centers for Disease, Prevention, Hantavirus pulmonary syndrome in visitors to a national park—Yosemite Valley, California, 2012. MMWR. Morbidity and mortality weekly report 61, 952 (2012).

Centers for Disease, Prevention, Investigational heptavalent botulinum antitoxin (HBAT) to replace licensed botulinum antitoxin AB and investigational botulinum antitoxin E. MMWR. Morbidity and mortality weekly report 59, 299 (2010).

Centers for Disease, Prevention, Update: outbreak of hantavirus infection—southwestern United States, 1993. MMWR. Morbidity and mortality weekly report 42, 441-443 (1993); published online EpubJun. 18.

Clark, et al., Clinical presentation and treatment of black widow spider envenomation: a review of 163 cases. Annals of emergency medicine 21, 782-787 (1992).

Custer, et al., Active and passive vaccination against hantavirus pulmonary syndrome with Andes virus M genome segment-based DNA vaccine. Journal of virology 77, 9894-9905 (2003).

Dart, et al., Efficacy, safety, and use of snake antivenoms in the United States. Annals of emergency medicine 37, 181-188 (2001).

Deeks, et al., Rabbit antithymocyte globulin (thymoglobulin): a review of its use in the prevention and treatment of acute renal allograft rejection. Drugs 69, 1483-1512 (2009).

Elgh, et al., Serological diagnosis of hantavirus infections by an enzyme-linked immunosorbent assay based on detection of immunoglobulin G and M responses to recombinant nucleocapsid proteins of five viral serotypes. Journal of clinical microbiology 35, 1122-1130 (1997).

Flego, et al., Clinical development of monoclonal antibody-based drugs in HIV and HCV diseases. BMC medicine 11, 4 (2013).

Hammerbeck, et al., in New Generation Vaccines, M. M. Levine, Ed. (informa healthcare, New York, 2010), vol. 1, chap. 83, pp. 905-913.

Hooper, et al., A lethal disease model for hantavirus pulmonary syndrome. Virology 289, 6-14 (2001).

Hooper, et al., A novel Sin Nombre virus DNA vaccine and its inclusion in a candidate pan-hantavirus vaccine against hantavirus pulmonary syndrome (HPS) and hemorrhagic fever with renal syndrome (HFRS). Vaccine 31, 4314-4321 (2013).

Hooper, et al., DNA vaccination with hantavirus M segment elicits neutralizing antibodies and protects against seoul virus infection. Virology 255, 269-278 (1999).

Hooper, et al., Hantaan/Andes virus DNA vaccine elicits a broadly cross-reactive neutralizing antibody response in nonhuman primates. Virology 347, 208-216 (2006).

Hooper, et al., Immune serum produced by DNA vaccination protects hamsters against lethal respiratory challenge with Andes virus. Journal of virology 82, 1332-1338 (2008).

Khan, et al. Hantavirus pulmonary syndrome: at the crossroads. Current opinion in infectious diseases 14, 205-209 (2001).

Kirkpatrick, Allergic histories and reactions of patients treated with digoxin immune Fab (ovine) antibody. The Digibind Study Advisory Panel. The American journal of emergency medicine 9, 7-10; and discussion 33-14 (1991).

Knust, et al., Twenty-year summary of surveillance for human hantavirus infections, United States. Emerging infectious diseases 19, 1934-1937 (2013).

Kohler, C. Milstein, Continuous cultures of fused cells secreting antibody of predefined specificity. Nature 256, 495-497 (1975).

Martinez, et al., Person-toperson transmission of Andes virus. Emerging infectious diseases 11, 1848-1853 (2005).

Matsushita, et al., Triple immunoglobulin gene knockout transchromosomic cattle: bovine lambda cluster deletion and its effect on fully human polyclonal antibody production. PloS one 9, e90383 (2014).

Nolte, et al., Hantavirus pulmonary syndrome in the United States: a pathological description of a disease caused by a new agent. Human pathology 26, 110-120 (1995).

Nunez, et al.,Yosemite Hantavirus Outbreak Investigation, Hantavirus infections among overnight visitors to Yosemite National Park, California, USA, 2012. Emerging infectious diseases 20, 386-393 (2014).

Olinger, Jr., et al., Delayed treatment of Ebola virus infection with plant-derived monoclonal antibodies provides protection in rhesus macaques. Proceedings of the National Academy of Sciences of the United States of America 109, 18030-18035 (2012).

Padula, et al., Hantavirus pulmonary syndrome outbreak in Argentina: molecular evidence for person-to-person transmission of Andes virus. Virology 241, 323-330 (1998).

Pettitt, et al., Therapeutic intervention of Ebola virus infection in rhesus macaques with the MB-003 monoclonal antibody cocktail. Science translational medicine 5, 199ra113 (2013).

Qiu, et al., Successful treatment of ebola virus-infected cynomolgus macaques with monoclonal antibodies. Science translational medicine 4, 138ra181 (2012).

Ray, et al., Study of Andes virus entry and neutralization using a pseudovirion system. Journal of virological methods 163, 416-423 (2010).

Reichert, Antibodies to watch in 2014, mid-year update. mAbs 6, 1-4 (2014).

Safronetz, et al, Pathophysiology of hantavirus pulmonary syndrome in rhesus macaques. Proceedings of the National Academy of Sciences of the United States of America 111, 7114-7119 (2014).

Sana, et al., Physiological level production of antigen-specific human immunoglobulin in cloned transchromosomic cattle. PloS one 8, e78119 (2013).

Schmaljohn, et al, Isolation and initial characterization of a newfound hantavirus from California. Virology 206, 963-972 (1995).

Schmaljohn, et al., in Fields Virology, D. M. Knipe, P. M. Howley, Eds. (Lippincott, Williams, and Wilkins, Philadelphia, 2006), pp. 1741-1789.

Schmaljohn, et al., Vaccines for hantaviruses. Vaccine 27 Suppl4, D61-64 (2009).

Seddik, et al. Development of an improved method for production of antiscorpion F(ab')2 fragment of IgG with high yield and potency. Journal of natural toxins 11, 123-132 (2002).

Trkola, et al., Delay of HIV-1 rebound after cessation of antiretroviral therapy through passive transfer of human neutralizing antibodies. Nature medicine 11, 615-622 (2005).

Trombley, et al., Comprehensive panel of real-time TaqMan polymerase chain reaction assays for detection and absolute quantification of filoviruses, arenaviruses, and New World hantaviruses. The American journal of tropical medicine and hygiene 82, 954-960 (2010).

Van Drunen Little-van den Hurk et al., "Electroporation-based DNA transfer enhances gene expression and immune responses to DNA vaccines in cattle" Vaccine 26:5503-09 (2008).

(56) References Cited

OTHER PUBLICATIONS

Vial, et al., Incubation period of hantavirus cardiopulmonary syndrome. Emerging infectious diseases 12, 1271-1273 (2006).

Wilson, et al., Epitopes involved in antibody-mediated protection from Ebola virus. Science 287, 1664-1666 (2000).

Young, et al., The incubation period of hantavirus pulmonary syndrome. The American journal of tropical medicine and hygiene 62, 714-717 (2000).

Zaki, et al., Hantavirus pulmonary syndrome. Pathogenesis of an emerging infectious disease. The American journal of pathology 146, 552-579 (1995).

Bounds et al., "Human Polyclonal Antibodies Produced through DNA Vaccination of Transchromosomal Cattle Provide Mice with Post-Exposure Protection against Lethal Zaire and Sudan Ebolaviruses." PLoS One 10(9):e0137786 (Sep. 2015).

Dye et al., "Production of Potent Fully Human Polyclonal Antibodies against Ebola Zaire Virus in Transchromosomal Cattle." Sci Rep. 6:24897 (Apr. 2016).

Hooper et al., "DNA vaccine-derived human IgG produced in transchromosomal bovines protect in lethal models of hantavirus pulmonary syndrome." Sci Transl Med. 6(264):264ra162 (Nov. 2014).

Rizvanov et al., "Replication and immunoactivity of the recombinant Peromyscus maniculatus cytomegalovirus expressing hantavirus G1 glycoprotein in vivo and in vitro." 24(3):327-34 (Jan. 2006; Epub Aug. 11, 2005).

Safronetz et al., "Adenovirus vectors expressing hantavirus proteins protect hamsters against lethal challenge with andes virus." J Virol. 83(14):7285-95 (Jul. 2009; Epub Apr. 29, 2009).

Martinez-Valdebenito et al., "Person-to-Person Household and Nosocomial Transmission of Andes Hantavirus, Southern Chile, 2011" Emerg Infect Dis. 20(10):1629-36 (Oct. 2014).

Stein et al., "Human polyclonal antibodies produced in transchromosomal cattle prevent lethal Zika virus infection and testicular atrophy in mice" Antiviral Research 146:164-173 (2017).

Vial et al., "High-dose intravenous methylprednisolone for hantavirus cardiopulmonary syndrome in Chile: a double-blind, randomized controlled clinical trial." Clin Infect Dis. 57(7):943-51 (Oct. 2013; Epub Jun. 19, 2013).

\* cited by examiner

SYSTEMS AND METHODS FOR THE PRODUCTION OF HUMAN POLYCLONAL ANTIBODIES

CROSS-REFERENCE TO RELATED APPLICATION(S)

This application claims priority to U.S. Provisional Application No. 62/260,023 that was filed on Nov. 25, 2015. The entire content of this provisional application is hereby incorporated herein by reference.

TECHNICAL FIELD

The disclosure relates to systems and methods for the production of human antibodies against various pathogens.

BACKGROUND

Current immunoglobulin products, such as human intravenous immunoglobulin (IVIG), monoclonal antibodies, and animal-derived polyclonal antibodies (pAbs), have known limitations. For example, human pAb products require large volumes of plasma from many convalescent human donors with confirmed high titers to make a commercial product. Although animal-derived pAbs could be an alternative, they typically have very high reactogenicity since animal-derived antibody products are foreign proteins in humans. This can cause a variety of adverse effects such as severe allergic reactions (anaphylaxis). To avoid serious side effects, animal antibodies are usually processed into smaller F(ab) or $F(ab')_2$ fragments, but this often reduces their half-life and potency. Monoclonal antibodies can be humanized or chimerized to human Fc fragments to avoid this, however, they are directed against a single epitope that may be subject to rapid mutational escape. This has led to the development of oligoclonal cocktails, but like monoclonal products, there are difficulties developing and producing enough of the product in a timely manner to assist in an outbreak scenario. There is a need in the art for rapid approach that combines the good safety profile of human polyclonal antibody products with high neutralizing antibody activity.

SUMMARY OF THE INVENTION

Disclosed herein is a method for producing human antibodies against a pathogen comprising injecting a non-human animal that produces human antibody with a pathogen-derived DNA vaccine in at least two locations of the animal; injecting the animal with an adjuvant in a location of the animal different from the location of the DNA vaccine location; collecting plasma from the animal after the injections; and purifying human polyclonal antibody from the plasma. In certain aspects, the location of adjuvant injection is adjacent to the location of DNA-vaccine injection. According to further aspects, the pathogen is selected from a group consisting of: Hantavirus, Ebola virus, Venezuelan Equine Encephalitis, and Zika virus.

In certain aspects, the non-human animal vaccinated in the instantly disclosed method is an ungulate and the ungulate is a transchromosomal ungulate. In exemplary embodiments, the transchromosomal ungulate has a human artificial chromosome (HAC) vector comprising genes encoding: one or more human antibody heavy chains, wherein each gene encoding an antibody heavy chain is operatively linked to a class switch regulatory element; one or more human antibody light chains; and one or more human antibody surrogate light chains, and/or an ungulate derived IgM heavy chain constant region; wherein at least one class switch regulatory element of the genes encoding the one or more human antibody heavy chains is replaced with an ungulate-derived class switch regulatory element.

Disclosed herein is a human polyclonal antibody against a pathogen, produced by injecting a non-human animal that produces human antibody with a pathogen-derived DNA vaccine and injecting an adjuvant at a different location on the animal from the location of the DNA vaccine injection. According to certain exemplary embodiments, a human polyclonal antibody against a pathogen is produced by injecting a non-human animal with a pathogen-derived DNA vaccine in at least two locations of the animal and injecting the animal with an adjuvant in a location of the animal different from the location of the DNA vaccine locations; collecting plasma from the animal after the injections; and purifying human polyclonal antibody from the plasma. In certain aspects, the pathogen is a virus. In further aspects, the virus is selected from the group consisting of: Hantavirus, Ebola virus, Venezuelan Equine Encephalitis, and Zika virus.

BRIEF DESCRIPTION OF THE DRAWINGS

FIG. 3 shows data demonstrating the bioavailability of purified a-HPS TcB human IgG in Syrian hamsters.

FIG. 4A shows survivial data demonstrating the efficacy of a-HPS TcB human IgG to protect against lethal HPS caused by ANDV when administered after exposure.

FIG. 4B shows ANDV data demonstrating the efficacy of a-HPS TcB human IgG to protect against lethal HPS caused by ANDV when administered after exposure.

FIG. 5A shows survival data demonstrating efficacy of a-HPS TcB human IgG to protect against lethal HPS caused by SNV when administered after exposure. FIG. 5B shows viral genome quantification data demonstrating efficacy of a-HPS TcB human IgG to protect against lethal HPS caused by SNV when administered after exposure.

FIG. 6A shows a schematic demonstrating the timeline of the vaccinations (black arrows), blood collections (red arrows) and plasma collections (blue arrows) for the TcBs.

FIG. 6B shows ELISA data showing IgG titers. FIG. 6C shows ELISA data showing IgG titers.

FIG. 7A shows data showing antibody titer from plasma collected from TcBs.

FIG. 7B shows data showing antibody titer from plasma collected from TcBs.

FIG. 7C shows data showing antibody titer from plasma collected from TcBs.

FIG. 8A shows data showing bioavailability of purified EBOV/SUDV human pAbs in mice.

FIG. 8B shows data showing bioavailability of purified EBOV/SUDV human pAbs in mice.

FIG. 9A shows weight loss data of BALB/c mice challenged with maEBOV when administered purified EBOV/SUDV human pAbs before or after challenge of BALB/c mice challenged with maEBOV when administered purified EBOV/SUDV human pAbs before or after challenge.

FIG. 9B shows survival data of BALB/c mice challenged with maEBOV when administered purified EBOV/SUDV human pAbs before or after challenge.

FIG. 10A shows weight loss data from BALB/c mice administered high, medium, or low doses of purified EBOV/SUDV human pAbs after maEBOV challenge.

FIG. 10B shows survival data from BALB/c mice administered high, medium, or low doses of purified EBOV/SUDV human pAbs after maEBOV challenge.

FIG. 11A shows weight loss data from IFNR −/− mice challenged with SUDV when administered purified EBOV/SUDV human pAbs after challenge.

FIG. 11B shows survival data from IFNR −/− mice challenged with SUDV when administered purified EBOV/SUDV human pAbs after challenge.

FIG. 21 shows the efficacy of combined TcpAb treatment against aerosol co-infection with influenza and VEEV.

FIG. 22 shows data demonstrating Zika virus neutralization activity in a Plaque Reduction Neutralization Test (PRNT).

DETAILED DESCRIPTION

Figure 1A:
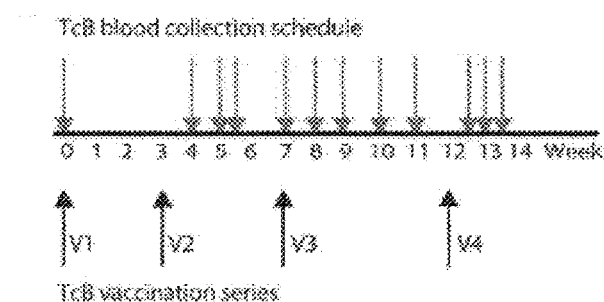
FIG. 1A shows a schematic demonstrating demonstrating experimental dosing regieme and sample collection.

Although the present invention has been described with reference to preferred embodiments, persons skilled in the art will recognize that changes may be made in form and detail without departing from the spirit and scope of the invention.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "analog" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein the term "adjuvant" refers to a compound that, when used in combination with a specific immunogen in a formulation, augments or otherwise alters or modifies the resultant immune response. Modification of the immune response includes intensification or broadening the specificity of either or both antibody and cellular immune responses. Modification of the immune response can also mean decreasing or suppressing certain antigen-specific immune responses.

As used herein, the term "DNA vaccine" means a nucleotide that when introduced into a mammal, induce the expression of encoded polypeptide antigens within the mammals, and cause the mammals' immune system to become reactive against the antigens. In certain embodiments the DNA vaccine is in the form of a DNA plasmid. DNA plasmid is one that includes an encoding sequence of a recombinant antigen that is capable of being expressed in a mammalian cell, upon the DNA plasmid entering after injection. In certain embodiments, injection is by way of needle-free injections. In alternative embodiments, the injection uses electroporation. Preferably, the encoding sequence is a consensus antigen that elicits an immune response in the target mammal. In some embodiments, the encoding sequence is constructs were optimized for mammalian expression, which can include one or more of the following: including the addition of a Kozak sequence, codon optimization, and RNA optimization. In some embodiments, these optimized encoding sequences can be subcloned into the pWRG7077 eukaryotic expression vector.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as the immunogenic composition, or can be administered separately. Either the protein or an expression vector encoding the protein can be administered to produce an immunostimulatory effect.

As used herein an "effective dose" generally refers to that amount of the immunogenic composition sufficient to induce immunity, to prevent and/or ameliorate virus infection or to reduce at least one symptom of infection and/or to enhance the efficacy of another dose of a immunogenic composition. An effective dose may refer to the amount of the immunogenic composition sufficient to delay or minimize the onset of an infection. An effective dose may also refer to the amount of the immunogenic composition that provides a therapeutic benefit in the treatment or management of infection. Further, an effective dose is the amount with respect to the immunogenic composition alone, or in combination with other therapies, that provides a therapeutic benefit in the treatment or management of a viral infection. An effective dose may also be the amount sufficient to enhance a subject's (e.g., a human's) own immune response against a subsequent exposure to virus. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease or reduces the severity of symptoms.

As used herein, the term "human antibody" means an antibody produced in a non-human animal that is otherwise indistinguishable from antibody produced in a human vaccinated by the same DNA vaccine. This is in contrast to "humanized antibodies" which are modified to have human characteristics, such as through generation of chimeras, but that maintain attributes of the host animal in which they are generated. Because human antibody made according to the instantly disclosed method is comprised of IgG that are fully human, no enzymatic treatment is needed to eliminate the risk of anaphylaxis and serum sickness associated with heterologous species IgG.

As used herein, the term "operably linked" refers to a first DNA molecule joined to a second DNA molecule, wherein the first and second DNA molecules are arranged so that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter is capable of affecting the transcription or translation of the transcribable DNA molecule.

As used herein, the term "pathogen" means any bacterium, virus or other disease causing microorganism. Examples include, but are not limited to, a virus, a viroid, a bacterium, a rickettsia, an acoxiella, a prion, a mycoplasma, or a fungus. Exemplary viral pathogens include Hantavirus, Ebola virus, Venezuelan Equine Encephalitis, and Zika virus. Moreover, the virus can be influenza virus, cytomegalovirus, avian leukosis-sarcoma virus (ALV), Rous Sarcoma virus (RSV), Mammalian C-type Murine leukemia virus (MLV), Feline leukemia virus (FeLV), simian sarcoma virus (SIS), B-type viruses like Mouse mammary tumor virus (MMTV), D-type viruses like Mason-Pfizer monkey virus (MPMV), Simian AIDS viruses (SRVs), HTLV-BLV group such as Human T-cell leukemia virus (HTLV), Simian T-cell leukemia virus (STLV), bovine leukemia virus (BLV). Lentivirinae comprise Human immunodeficiency virus (HIV-1 and HIV-2), Simian immunodeficiency virus (SIV), Feline immunodeficiency virus (FIV), Visna/maedi virus (MV), Equine infectious anemia virus (EIAV), Caprine arthritis-encephalitis virus (CAEV). Spumavirinae or "Foamy viruses" like Human (HSRV), Simian (SSRV), Feline (FSRV), Bovine (BSRV), Murine (MSRV), endogenous retroviruses (ERV), papilloma virus, respiratory syncytial virus, poliomyelitis virus, pox virus, measles virus, arbor virus, Coxsackie virus, herpes virus, hantavirus, hepatitis virus, Baculovirus, mumps virus, circovirus, vichaivirus, arenavirus, or rotavirus. A bacteria may be a member of the genus *Neisseria, Aerobacter, Pseudomonas, Porphyromonas, Salmonella, Escherichia, Pasteurella, Shigella, Bacillus, Helibacter, Corynebacterium, Clostridium, Mycobacterium, Yersinia, Staphylococcus; Bordetelia, Brucelia, Vibrio, Streptococcus, Plasmodium, Schisostoma, Candida*. Any microbial infections, which are present and/or transmitted as Zoonoses, Cyclozoonoses, Metazoonoses, Saprozoonoses, Anthropozoonoses, Zooanthropozoonoses and Amphixenoses, are also contemplated.

According to certain embodiments, the methods disclosed herein induce the production of high affinity human polyclonal antibodies against a pathogen in the host. These high affinity anti-pathogen antibodies demonstrate higher affinities than anti-pathogen antibodies produced through conventional methods.

The term "affinity" refers to the strength of the interaction between an epitope and an antibody's antigen binding site. The affinity can be determined, for example, using the equation $$K_A = \frac{[Ab-Ag]}{[Ab][Ag]}$$

Where $K_A$=affinity constant; [Ab]=molar concentration of unoccupied binding sites on the antibody; [Ag]=molar concentration of unoccupied binding sites on the antigen; and [Ab-Ag]=molar concentration of the antibody-antigen complex. The $K_A$ describes how much antibody-antigen complex exists at the point when equilibrium is reached. The time taken for this to occur depends on rate of diffusion and is similar for every antibody. However, high-affinity antibodies will bind a greater amount of antigen in a shorter period of time than low-affinity antibodies. The $K_A$ of the antibodies produced can vary, and range from between about $10^5$ mol$^{-1}$ to about $10^{12}$ mol$^{-1}$ or more. The $K_A$ can be influenced by factors including pH, temperature, and buffer composition.

The antibody affinity can be measured using any means commonly employed in the art, including but not limited to the use of biosensors, such as surface plasmon resonance (e.g. Biacore). Resonance units are proportional to the degree of binding of soluble ligand to the immobilized receptor (or soluble antibody to immobilized antigen). Determining the amount of binding at equilibrium with different known concentrations of receptor (antibody) and ligand (protein antigen) allows the calculation of equilibrium constants ($K_A$, $K_D$), and the rates of dissociation and association (koff, kon).

For example, KD (the equilibrium dissociation constant) is a ratio of koff/kon, between the antibody and its antigen. KD and affinity are inversely related. The lower the KD value (lower antibody concentration), the higher the affinity of the antibody. Most antibodies have KD values in the low micromolar ($10^{-6}$) to nanomolar ($10^{-7}$ to $10^{-9}$) range. High affinity antibodies are generally considered to be in the low nanomolar range ($10^{-9}$) with very high affinity antibodies being in the picomolar ($10^{-12}$) range or lower (e.g. $10^{-13}$ to $10^{-14}$ range). In one embodiment, the antibodies produced by immunization with the nanoparticles disclosed herein have a KD ranging from about $10^{-6}$ to about $10^{-15}$, from about $10^{-7}$ to about $10^{-15}$, from about $10^{-8}$ to about $10^{-15}$, and from about $10^{-9}$ to about $10^{-15}$, from about $10^{-10}$ to about $10^{-15}$, about $10^{-11}$ to about $10^{-15}$, about $10^{-12}$ to about $10^{-15}$, about $10^{-13}$ to about $10^{-14}$, about $10^{-13}$ to about $10^{-15}$, and about $10^{-14}$ to about $10^{-15}$. In a preferred embodiment, the antibodies produced by immunization according to the method disclosed herein have a KD ranging from about $10^{-10}$ to about $10^{-14}$.

The antibodies produced by the methods disclosed herein have low rate of dissociation ($K_{off}$), indicating they bind tightly to the antigen. In one embodiment, the antibodies produced by immunization with the nanoparticles disclosed herein have a $K_{off}$ ranging from about $10^{-3}$ $M^{-1}$ to about $10^{-13}$ $M^{-1}$, from about $10^{-5}$ $M^{-1}$ to about $10^{-13}$ $M^{-1}$, from about $10^{-6}$ $M^{-1}$ to about $10^{-13}$ $M^{-1}$, from about $10^{-7}$ $M^{-1}$ to about $10^{-13}$ $M^{-1}$, from about $10^{-8}$ $M^{-1}$ to about $10^{-13}$ $M^{-1}$, from about $10^{-9}$ $M^{-1}$ to about $10^{-13}$ $M^{-1}$, from about $10^{-10}$ $M^{-1}$ to about $10^{-13}$ $M^{-1}$, from about $10^{-11}$ $M^{-1}$ to about $10^{-13}$ $M^{-1}$, or from about $10^{-12}$ $M^{-1}$ to about $10^{-13}$ $M^{-1}$.

Disclosed herein is a method for producing human antibodies against a pathogen comprising: injecting a non-human animal with a pathogen-derived DNA vaccine in at least one location of the animal; injecting the animal with an adjuvant in a location of the animal different from the location of the DNA vaccine location; collecting plasma from the animal after the injections; and purifying polyclonal antibody from the plasma.

Disclosed herein is a method for producing human antibodies against a pathogen comprising injecting a non-human animal with a pathogen-derived DNA vaccine in at least two locations of the animal; injecting the animal with an adjuvant in a location of the animal different from the location of the DNA vaccine location; collecting plasma from the animal after the injections; and purifying polyclonal antibody from the plasma. In certain aspects, the location of adjuvant injection is adjacent to the location of DNA-vaccine injection. According to further aspects, the pathogen is selected from a group consisting of: Hantavirus, Ebola virus, Venezuelan Equine Encephalitis, and Zika virus.

According to certain embodiments, the at least two locations of DNA-vaccine injection are each injected with a DNA vaccine derived from a distinct strain of the pathogen. The delivery of different strains at distinct injections sites on the animal surprisingly gives rise to a more robust immunogenic response than if the distinct strains were admixed and delivered to a single injection site. The resulting pool of polyclonal antibodies have enhanced reactivity and neutralization capacity against a broader range of pathogens than mixed single site injections.

According to certain embodiments of the disclosed method, each of the at least two locations is on a separate quarter of the animal. For example, in exemplary embodiments, a first injection site is injected with a first pathogen strain on right hind quarter of the animal and the second injection site is injected with a second pathogen strain on left hind quarter of the animal. Accordingly to certain exemplary embodiments, the pathogen is Hantavirus and the two distinct strains are Sin Nombre virus and Andes Hantavirus. A person skilled in the art will appreciate that other virus pathogens and strains are possible. According to further exemplary embodiments, the pathogen is Ebola virus (EBOv) and two distinct strains are Ziare and Sudan.

According to certain aspects, the DNA vaccine is injected subcutaneously or sub-dermally and the adjuvant is injected intramuscularly.

According to still further aspects, the method further comprises delivering one or more sets of booster injections. In these embodiments, the injection steps are repeated at set intervals following 14 days or later after the initial injection. According to certain exemplary embodiments, the booster injections are delivered at an interval of about 21 to about 28 days. As will be appreciated by a person having skill in the art, other post-injection booster intervals are possible. In further exemplary intervals, booster injections are given at 2 months, 6 months and/or 12 months. Other intervals are possible.

According to certain embodiments, plasma is collected from the animal between about 6 days to about 16 days after injection. Once the plasma is collected, the polyclonal antibodies are purified. In certain embodiments, the purified polyclonal antibody made according to the instantly disclosed method is substantially similar to a purified polyclonal antibody produced by a human vaccinated with the DNA vaccine. According to further embodiments, the purified polyclonal antibody made according to the instantly disclosed method is indistinguishable from a purified polyclonal antibody produced by a human vaccinated with the DNA vaccine. "Indistinguishable," as used herein, means that a person skilled in the art would be unable to detect a species-dependent difference through the use of standard laboratory tests.

Non-human animals used in the disclosed methods are capable of generating fully human antibodies in response to inoculation with a vaccine. Various techniques for modifying the genome of non-human animals can be employed to develop an animal capable of producing human animals. In certain embodiments, human artificial chromosome (HAC) is engineered into the animal. The HAC contains the germline repertoire of the human antibody heavy chain genes (human chromosome 14 fragment) and the human antibody light chain genes either one or both of kappa (human chromosome 2 fragment) lambda (human chromosome 22 fragment). The HAC is transferred into cells of the non-human species and the animals are produced by somatic cell nuclear transfer. In certain alternative embodiments, a yeast artificial chromosome (YAC) wherein the all or part of the germline repertoire of the human antibody genes have been inserted into the YAC (same process as above) is employed to produce a suitable animal for use in the disclosed methods. In yet further embodiments, homologous recombination is employed to modify the animals genome to introduce the requisite human genes. In yet further embodiments, techniques known in the art for gene editing are employed (e.g. Zinc fingers, TALENS, CRISPR).

Various non-human animals may be suitable for use in the disclosed methods. In certain aspects, the animal is a mammal. In further aspects, the mammal is an ungulate. In still further aspects, the animal is a bovine.

According to yet further aspects, the animal is an ungulate and the ungulate is a transchromosomal ungulate. In exemplary embodiments, the transchromosomal ungulate has a human artificial chromosome (HAC) vector comprising genes encoding: one or more human antibody heavy chains, wherein each gene encoding an antibody heavy chain is operatively linked to a class switch regulatory element; one or more human antibody light chains; and one or more human antibody surrogate light chains, and/or an ungulate derived IgM heavy chain constant region; wherein at least one class switch regulatory element of the genes encoding the one or more human antibody heavy chains is replaced with an ungulate-derived class switch regulatory element.

Disclosed herein is a human polyclonal antibody against a pathogen, produced by injecting a non-human animal with a pathogen-derived DNA vaccine in at least two locations of the animal; injecting the animal with an adjuvant in a location of the animal different from the location of the DNA vaccine location; collecting plasma from the animal after the injections; and purifying polyclonal antibody from the plasma. In certain aspects, the pathogen is a virus. In further aspects, the virus is selected from the group consisting of: Hantavirus, Ebola virus, Venezuelan Equine Encephalitis, and Zika virus.

The antibodies according to the method disclosed herein neutralize the target virus. In certain embodiments, the antibodies can be broadly neutralizing antibodies and neutralize one or more virus strains, clades, or coronaviruses, or the antibodies can neutralize only one virus strain. The neutralization ability of the antibodies can be measured by any means commonly employed in the art, including, but not limited to, Fluorescence Reduction Neutralization Test (FRNT50), in vitro cell-based assays which measure the amount of virion released from immunized cells, and in vivo assays which measure the infection in an immunized animal.

In certain aspects, disclosed is a method for producing an antibody against Ebola virus (EBOV) comprising immunizing a transchromosomal (Tc) ungulate an immunogenic composition comprising a recombinant glycoprotein (rGP) of EBOV; repeating the immunization step at least one time; collecting serum from the ungulate; purifying the antibody from the serum. In certain aspects, the immunogenic composition is co-administered with an adjuvant. In further aspects, the immunization step is repeated at least 8 times. In still further aspects, the dose of immunogenic composition is increased over subsequent administrations. In yet further aspects, the dose of immunogenic composition is increased after the 4th immunization.

According to certain aspects, each immunization step is separated by a period of about 3-8 weeks. In further aspects, the immunogenic composition is administered in at a dose of about 2 mg to about 20 mg per animal.

According to certain embodiments, the Tc ungulate has a human artificial chromosome (HAC) vector. In certain aspects, the HAC comprises genes encoding: one or more human antibody heavy chains, wherein each gene encoding an antibody heavy chain is operatively linked to a class switch regulatory element; one or more human antibody light chains; and one or more human antibody surrogate light chains, and/or an ungulate derived IgM heavy chain constant region; wherein at least one class switch regulatory element of the genes encoding the one or more human antibody heavy chains is replaced with an ungulate-derived class switch regulatory element. In certain aspects, the Tc ungulate is a triple knock-out for endogenous bovine immunoglobulin genes IGHM, IGHML1, and IGL. That is, Tc ungulate is IGHM (−/−), IGHML1(−/−), and IGL (−/−).

According to certain aspects, disclosed herein is a pharmaceutical composition comprising an antibody produced according to the methods disclosed herein and a pharmaceutically acceptable carrier thereof. In certain aspects, the pharmaceutical composition further comprises an adjuvant. In still further aspects, the pharmaceutical composition further comprises an immune stimulant.

According to further aspects, disclosed herein is a method of treating or preventing a pathogen infection comprising administering to a subject in need thereof an immunogenic composition comprising an antibody produced according to the methods disclosed herein. In certain aspects, the immunogenic composition further comprises an adjuvant. In still further aspects, the immunogenic composition further comprises an immune stimulant. In yet further aspects, the immunogenic composition is administered at a dose of about 50 mg/kg to about 300 mg/kg. According to still further embodiments, the immunogenic composition is administered between about 1 day to about 12 days after the subject is infected with a pathogen. In further aspects, the administration of the immunogenic composition is repeated at 2-4 day intervals following infection.

Disclosed herein are methods for producing antibodies using a Transchromosomic (Tc) ungulate in which the ungulate immunoglobulin genes have been knocked out and a human artificial chromosome (HAC) containing the full germ line sequence of human immunoglobulin has been inserted allowing the Tc ungulates to produce fully human antibodies[19-22] Like traditional animal systems used to produce polyclonal antibodies, Tc ungulates can be hyperimmunized over a long period of time with vaccines containing strong adjuvants and/or immune stimulators.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

In this example, human antibodies to two strains of Hantavirus were produced via TC bovine. That is, the TC bovine were immunized with the two viral strains.

The use of DNA vaccine technology and transchromosomal bovines (TcBs) to produce fully human polyclonal immunoglobulins (IgG) with potent antiviral neutralizing activity is demonstrated. Specifically, two hantavirus DNA vaccines [Andes virus (ANDV) DNA vaccine and Sin Nombre virus (SNV) DNA vaccine] were used to produce a candidate immunoglobulin product for the prevention and treatment of hantavirus pulmonary syndrome (HPS). A needle-free jet injection device was used to vaccinate TcB, and high titer neutralizing antibodies (titers >1000) against both viruses were produced within 1 month. Plasma collected at day 10 after the fourth vaccination was used to produce purified a-HPS TcB human IgG. Treatment with 20,000 neutralizing antibody units (NAU)/kg starting 5 days after challenge with ANDV protected seven of eight animals, whereas zero of eight animals treated with the same dose of normal TcB human IgG survived. Likewise, treatment with 20,000 NAU/kg starting 5 days after challenge with SNV protected immunocompromised hamsters from lethal HPS, protecting five of eight animals. The findings that the a-HPS TcB human IgG is capable of protecting in animal models of lethal HPS when administered after exposure provides proof of concept that this approach can be used to develop candidate next-generation polyclonal immunoglobulinbased medical products without the need for human donors, despeciation protocols, or inactivated/attenuated vaccine antigen.

Here, the possibility of using DNA vaccine technology to produce high-titer a-HPS neutralizing antibodies in TcB is demonstrated. The antibodies specifically target both ANDV and SNV, illustrating the capacity to use single TcB animal to produce antibodies aimed at multiple pathogens. Furthermore, it is showed that purified a-HPS TcB human IgG produced using this platform protect when used as a post-exposure prophylactic in two animal models of lethal HPS.

Materials and Methods

Study Design

This study evaluated the potential of TcB vaccinated with ANDV and SNV DNA vaccines to express human IgG and the efficacy of these antibodies to prevent lethal hantavirus disease in two small-animal models. Purified TcB human IgG was evaluated by both classical plaque reduction and PsVNAs, and bioavailability of these antibodies was assessed in the Syrian hamster. Finally, the ability of TcB human IgG to prevent lethal disease caused by ANDV in immunocompetent hamsters and SNV in immunosuppressed hamsters was evaluated. Animals were assigned randomly at the beginning of each study.

Virus and Cells

Twice plaque-purified SNV strain CC107 and ANDV strain Chile-9717869 were propagated in Vero E6 cells [Vero C1008; American Type Culture Collection (ATCC) CRL 1586]. The VSVDG*rLuc pseudovirion (PsV) is a recombinant vesicular stomatitis virus (VSV) derived from a full-length complementary DNA clone of the VSV Indiana serotype in which the G protein gene has been replaced with the Renilla luciferase gene. ANDV and SNV PsV were produced in human embryonic kidney (HEK) 293 cells using DNA vaccine plasmids pWRG/AND-M[opt2] and pWRG/SN-M[opt], respectively, by known methods. Vero, HEK 293T, and Vero E6 cells were maintained in Eagle's minimum essential medium with Earle's salts containing 10% fetal bovine serum, 10 mM Hepes (pH 7.4), and penicillin-streptomycin (Invitrogen) at 1×, and gentamicin sulfate (50 mg/ml) (Vero E6 cells only) [complete Eagle's minimum essential medium (cEMEM)] at 37° C. in a 5% $CO_2$ incubator.

Transchromosomal Bovine

The two TcBs used in this study have homozygous triple knockout in endogenous bovine immunoglobulin genes (IGHM−/−IGHML1−/−IGL−/−) and contain human artificial chromosome (HAC) vector labeled as KcHACD. This HAC vector consists of human chromosome 14 fragment, which contains the entire human immunoglobulin heavy chain locus except that the IGHM constant region remains bovine; and human chromosome 2 fragment, which contains the entire human immunoglobulin k light chain locus.

TcB Vaccination

As shown in Table 1 below, two TcBs were vaccinated at 3- to 4-week intervals with both the ANDV DNA vaccine, pWRG/AND-M[opt2], and the SNV DNA vaccine, pWRG/SN-M[opt], via the PharmaJet IMStratis injection device. Each vaccine was administered with two injections of 3 mg each behind the ear and on the hind leg (for 6 mg total per site). The ANDV DNA vaccine was administered on the left side of the animal; the SNV DNA vaccine was administered on the right side of the animal. To evaluate whether co-administration of DNA vaccine with adjuvant plus immune stimulator could enhance immune response, Tc animal #2 was administrated with Montanide ISA 206 adjuvant (Seppic) plus the saponinderived immune stimulant Quil A (Accurate Chemicals) adjacent to each DNA vaccination site at the final booster (V4). The adjuvant formulation [Quil A (0.5 mg/ml) in a 50% solution of ISA 206] was administered as a 1-ml injection using needle and syringe. The adjuvant was administered adjacent (1 to 2 cm) to each DNA vaccination site (2 ml total). At V4, Tc animal #1 was administered the DNA vaccine without adjuvant.

TABLE 1

| TC Bovine | Vaccination | Vaccine Formulation |
|---|---|---|
| #2207; #2210 | V1 to V3 at 3-4 week intervals | AND Vaccine: 12 mg AND-M plasmid (left side) SN Vaccine: 12 mg SN-M plasmid (right side) |
| #2207 | V4 | AND Vaccine: 12 mg AND-M plasmid (left side) SN Vaccine: 12 mg SN-M plasmid (right side) |
| #2210 | V4 | AND Vaccine: 12 mg AND-M plasmid (left side) + Adjuvant SN Vaccine: 12 mg SN-M plasmid (right side) + Adjuvant |

Purification of Fully Human IgG

TcB plasma collected from day 10 after V4 of Tc animal #2 was the source material for purifying fully human IgG against hantaviruses using the method described below. Frozen Tc plasma was thawed at room temperature overnight, pH-adjusted to 4.80 with dropwise addition of 20% acetic acid (Fisher, catalog #A491), fractionated by caprylic acid (Amresco, catalog #E499) at a caprylic acid/total protein ratio of 1.0, and then clarified by centrifugation at 10,000 g for 20 min at room temperature. The supernatant containing IgG was then neutralized to pH 7.50 with 1 M tris, 0.22 mm—filtered, and affinity-purified with an a-human IgG light chain-specific column, KappaSelect (GE Healthcare, catalog #17545804). Fully human IgG was further purified by passage over an a-bovine IgG heavy chain-specific affinity column (Capto HC15 from GE Healthcare, catalog #17-5457-03). The purified a-HPS human IgG has a protein concentration of 8.42 mg/ml in a sterile-filtered buffer consisting of 10 mM glutamic acid monosodium salt, 262 mM D-sorbitol, and Tween (0.05 mg/ml) (pH 5.5).

Pseudovirion Neutralization Assay

The PsVNA was performed using a known method. Briefly, an initial 1:10 dilution of heat-inactivated sera was made followed by fivefold serial dilutions (in triplicate) that were mixed with equal volume of cEMEM containing 4000 focus-forming units of PsV of interest with 10% human complement (Sigma) and then incubated overnight at 4° C. After this incubation, 50 ml was inoculated onto Vero cell monolayers in a clear bottom black-walled 96-well plate (Corning). Plates were incubated at 37° C. for 18 to 24 hours. The medium was discarded, and cells were lysed according to the luciferase kit protocol (Promega #E2820). A Tecan M200 Pro was used to acquire luciferase data. The values were graphed using GraphPad Prism software (version 6) to calculate the percent neutralization. Data for each dilution series were fit to a four-parameter logistic curve using GraphPad Prism and then PsVNA80 neutralization titers were interpolated. Geometric mean titers from triplicates were reported.

Plaque Reduction Neutralization Test

PRNT was performed using Vero E6 cells using a known method. The 80% PRNT titer (PRNT80 titer) is the reciprocal of the highest serum dilution reducing the number of plaques by 80% relative to the average number of plaques in control wells that received medium alone.

ANDV Lethal Disease Model Using Syrian Hamsters

Female Syrian hamsters aged 6 to 8 weeks (Harlan) were anesthetized by inhalation of vaporized isoflurane using an IMPAC 6 veterinary anesthesia machine. Once anesthetized, hamsters were injected with 200 PFU of ANDV diluted in phosphate-buffered saline (PBS). Intramuscular (caudal thigh) injections consisted of 0.2 ml delivered using a 1-ml syringe with a 25-gauge, 5/8-inch needle. The mean day to death of a 200-PFU intramuscular challenge in this model is 11, with a range of 9 to 14.

SNV Lethal Disease Model Using Transiently Immunosuppressed Syrian Hamsters

Female Syrian hamsters aged 6 to 8 weeks (Harlan) were used in this experiment. The hamsters were anesthetized by inhalation of vaporized isoflurane using an IMPAC 6 veterinary anesthesia machine for all injections described below. Hamsters were transiently immunosuppressed by daily injections of dexamethasone and cyclophosphamide administered by the intraperitoneal route starting on day −3 and ending on day 13 after virus challenge using a known process. Hamsters were challenged by intramuscular injection of 0.2 ml of PBS containing 2000 PFU of SNV on day 0. The mean day to death of a 2000-PFU intramuscular challenge in this model is 13, with a range of 10 to 14.

N-Specific ELISA

The ELISA used to detect N-specific antibodies (N-ELISA) is a known method. The endpoint titer was determined as the highest dilution that had an optical density (OD) greater than the mean OD for serum samples from negative control wells plus 3 SDs. The PUUV N antigen was used to detect ANDV and SNVN-specific antibodies as previously reported.

Isolation of RNA and Real-Time PCR

About 250 mg of lung tissue was homogenized in 1.0 ml of TRIzol reagent using gentleMACS M tubes and a gentleMACS dissociator on the RNA setting. Serum samples were added directly to TRIzol reagent. RNA was extracted from TRIzol samples as recommended by the manufacturer. The concentration of the extracted RNA was determined using a NanoDrop 8000 instrument and raised to a final concentration of 10 ng/ml. Real-time PCR was conducted on a Bio-Rad CFX thermal cycler using an Invitrogen Power SYBR Green RNA-to-Ct 1-Step kit according to the manufacturer's protocols. Primer sequences are as follows: SNV S 26F, 5'-CTACGACTAAAGCTGGAATGAGC-3'; SNV S 96R, 5'-GAGTTGTTGTTCGTGGAGAGTG-3' (50). Cycling conditions were 30 min at 48° C., 10 min at 95° C., followed by 40 cycles of 15 s at 95° C. and 1 min at 60° C. Data acquisition occurs after the annealing step.

Statistical Analysis

Survival analyses were done using Kaplan-Meier survival analysis with log-rank tests. P values of less than 0.05 were considered significant. Comparison of levels of viral genome was done using Student's t test. Analyses were conducted using GraphPad Prism (version 6).

Results

TcB Vaccination Responses

In this specific example, the addition of the co-located adjuvant injection in the fourth vaccination significantly boosted the titers of both vaccine strains, which was an unexpected result.

Figure 1B:
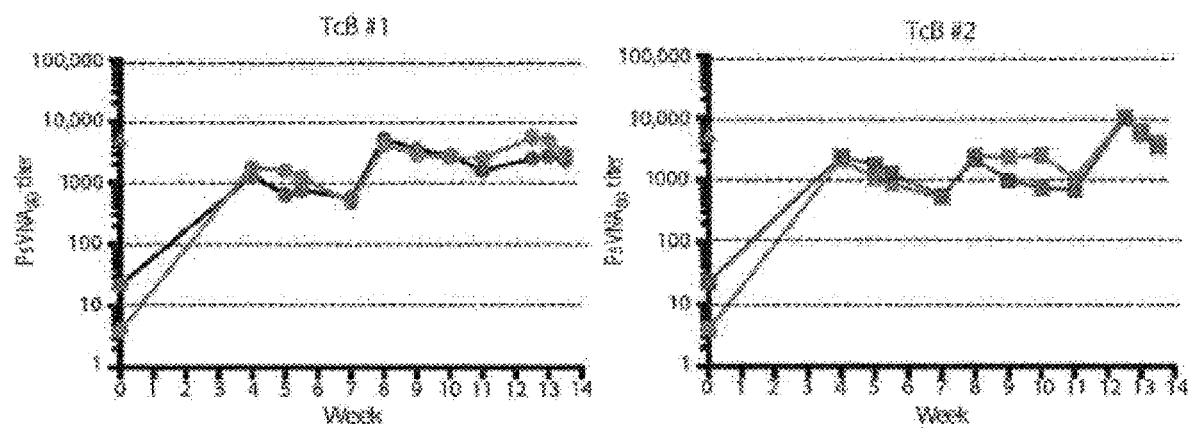
FIG. 1B shows data demonstrating the neutralizing antibody responses in TcBs vaccinated with hantavirus DNA vaccine plasmids.
Figure 1C:
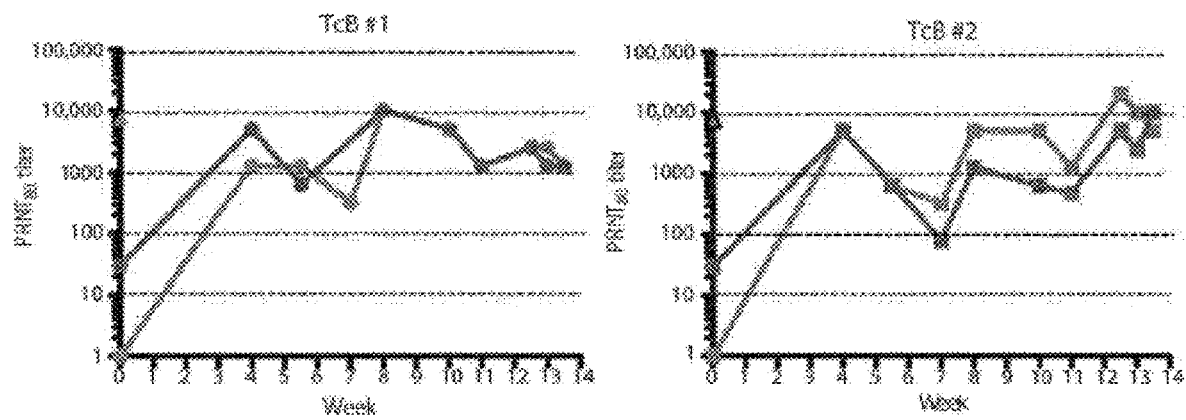
FIG. 1C shows data demonstrating the neutralizing antibody responses in TcBs vaccinated with hantavirus DNA vaccine plasmids.

The construction and testing of first generation ANDV DNA vaccines and SNV DNA vaccines that encode the full-length glycoproteins of ANDV and SNV, respectively, were previously reported. Here, the goal was to co-administer the ANDV and SNV DNA vaccine plasmids to TcB to produce human neutralizing antibodies against both ANDV and SNV. With the PharmaJet Stratis needle-free disposable syringe jet injection device, two TcBs carrying the HAC vector labeled as KcHACD in the triple KO background (23) were vaccinated four times, intramuscularly, with both the ANDV and SNV DNA vaccines at separate locations. To evaluate whether an adjuvant plus immune stimulator would enhance immune response to the vaccine, TcB #2 was administrated ISA 206 adjuvant plus the saponin-derived immune stimulant Quil A adjacent to each DNA vaccination site at the final booster [fourth vaccination (V4)]. As a control, TcB #1 was given a DNA vaccine without adjuvant for V4. Serum samples and large volumes of plasma were collected before the initial vaccination and after the second, third, and fourth vaccinations (FIG. 1A). Neutralizing antibody titers were determined using a pseudovirion neutralization assay (PsVNA) and a classical plaque reduction neutralization test (PRNT) (FIGS. 1B and 1C). Both bovines developed neutralizing antibodies against ANDV and SNV. Titers decreased with time after the second vaccination, with higher responses after the third and fourth boost. The neutralizing activity against both ANDV and SNV was similar, and both the PsVNA and PRNT resulted in the same trends in neutralizing activity. a-ANDV titers from TcB sera eventually surpassed the a-ANDV titers in human convalescent fresh-frozen plasma (FFP) used in previous passive protection experiments (for example, TcB #1 PRNT80=10, 240 versus human FFP PRNT80=7240) (11).

Neutralizing Activity of Purified TcB Human IgG

Fully human IgG (referred hitherto as TcB human IgG) were purified from plasma collected from one of the immunized animals (TcB #2). Human IgG and bovine IgM capture enzyme linked immunosorbent assay (ELISA) and SDS-polyacrylamide gel electrophoresis (SDS-PAGE) indicated that about 97% of the immunoglobulin was human IgG and 3% was IgM. The human IgG isotype subclass distribution of IgG1, IgG2, IgG3, and IgG4 was 54, 44, 1.1, and 0.37%, respectively, comparable to in human IVIG (intravenous immunoglobulin): 67, 26, 2.6, and 2.5%, respectively. The purified TcB human immunoglobulin (8.42 mg/ml) was evaluated for a-SNV (FIG. 2A) and a-ANDV (FIG. 2B) neutralizing activity in the PsVNA and the PRNT. High levels of both a-ANDV and a-SNV neutralizing antibodies were detected. a-ANDV convalescent FFP was used as a positive control for a-ANDV activity. The purified TcB human IgG had higher a-ANDV activity than the FFP in both the PsVNA and the PRNT. Also, whereas the FFP had only low levels of cross-neutralizing activity against SNV, the purified TcB human IgG had potent neutralizing activity against both ANDV and SNV. To confirm that the human IgG was the major contributor to the neutralizing activity, IgG was depleted from the purified immunoglobulin (8.42 mg/ml) by incubating with protein G-labeled magnetic beads. This process removed IgG from the sample as visualized by SDS-PAGE. Pre- and post-depletion samples were evaluated for a-ANDV neutralizing activity in the PsVNA. The anti-ANDV neutralizing activity in the IgG-depleted sample was reduced from PsVNA80 titer of 4565 to 63, demonstrating that the IgM contribution to neutralizing activity was minimal.

Bioavailability of TcB human IgG in Syrian Hamsters

Figures 3, 4A, 4B:
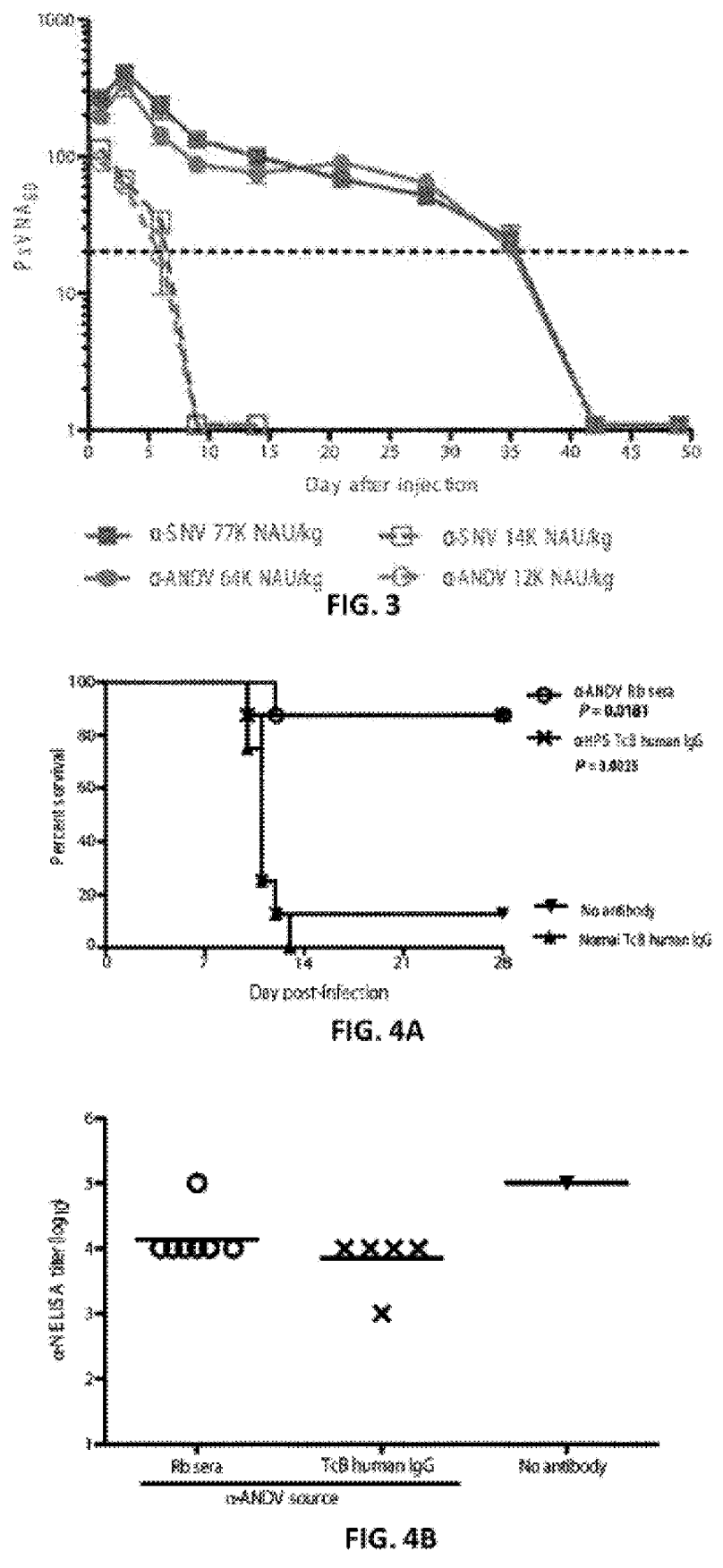

ANDV causes a disease in Syrian hamsters that closely resembles HPS in humans (24). Similarly, SNV causes HPS in Syrian hamsters that have been transiently immunosuppressed (15). Before testing the TcB human IgG for protection in the hamster models, the bioavailability of this candidate product in hamsters was evaluated. Groups of hamsters were injected subcutaneously with either a high dose {a-ANDV [64,000 neutralizing antibody units (NAU)/kg] equating to a-SNV human IgG (77,000 NAU/kg), or 52.63 mg/kg} or low dose [a-ANDV (12,000 NAU/kg) equating to a-SNV human IgG (14,000 NAU/kg), or 9.87 mg/kg] of purified fully human IgG from TcB #2. Serum samples were obtained on the indicated day after injection until neutralization activity was no longer detected. a-ANDV and a-SNV neutralizing antibody titers were determined by PsVNA (FIG. 3). Hamsters administered a high dosage of a-ANDV and a-SNV human IgG had detectable titers against both viruses out to day 35, whereas hamsters administered a low dosage of fully human IgG only had detectable titers out to day 6. Half-lives were calculated to be 5.8 and 6.8 days for a-ANDV and a-SNV, respectively.

Protection From Lethal ANDV Challenge

To determine the protective efficacy of a-HPS TcB human IgG in a model of lethal HPS caused by ANDV, hamsters were challenged with 200 plaque-forming units (PFU) of ANDV. One group was then administered purified a-HPS TcB human IgG (16.45 mg/kg) (a-ANDV activity, 20,000 NAU/kg), subcutaneously, on days 5 and 8 after challenge. Negative control hamsters were injected with normal TcB human IgG (16.45 mg/kg) purified from the same, but prevaccinated, TcB. Positive control hamsters were administered a single dose (12,000 NAU/kg) of previously described a-ANDV rabbit sera produced using the ANDV DNA vaccine on day 5 (16). A fourth group of eight hamsters was exposed to virus but not treated with antibody.

Seven of eight hamsters treated with a-HPS TcB human IgG survived with no signs of disease (n=8; P=0.0025, Kaplan-Meier with log-rank test, when compared to normal TcB human IgG). Similarly, seven of eight hamsters receiving the positive control rabbit sera survived (n=8; P=0.0181, Kaplan-Meier with log-rank test, when compared to no antibody control). In contrast, all eight hamsters treated with the normal TcB human IgG developed HPS disease and succumbed 10 to 13 days after challenge. Only one of eight hamsters in the untreated group survived (FIG. 4A). All surviving hamsters had positive a-nucleocapsid (N) ELISA titers 28 days after challenge, indicating a productive ANDV infection (FIG. 4B). The results of this experiment demonstrated that the a-HPS TcB human IgG was capable of protecting against ANDV when used as a post-exposure prophylactic.

Protection From Lethal SNV Challenge

A lethal HPS animalmodel involving SNV infection of transiently immunosuppressed hamsters was recently described. Using this model, it was determined whether the a-HPS TcB human IgG could protect against lethal disease caused by SNV. Groups of immunosuppressed hamsters were challenged with 2000 PFU of SNV. One group of hamsters was then administered purified a-HPS TcB human IgG (21.9 mg/kg) (a-SNVactivity, 20,000 NAU/kg) on days 5 and 8 after challenge. Negative control hamsters were given normal TcB human IgG (21.9 mg/kg) purified from the same, but prevaccinated, TcB. Positive control hamsters were administered previously described a-SNV rabbit sera (20,000 NAU/kg) produced using the SNVDNAvaccine (13), and a fourth group of hamsters was not injected with antibody.

Figures 5A, 5B:
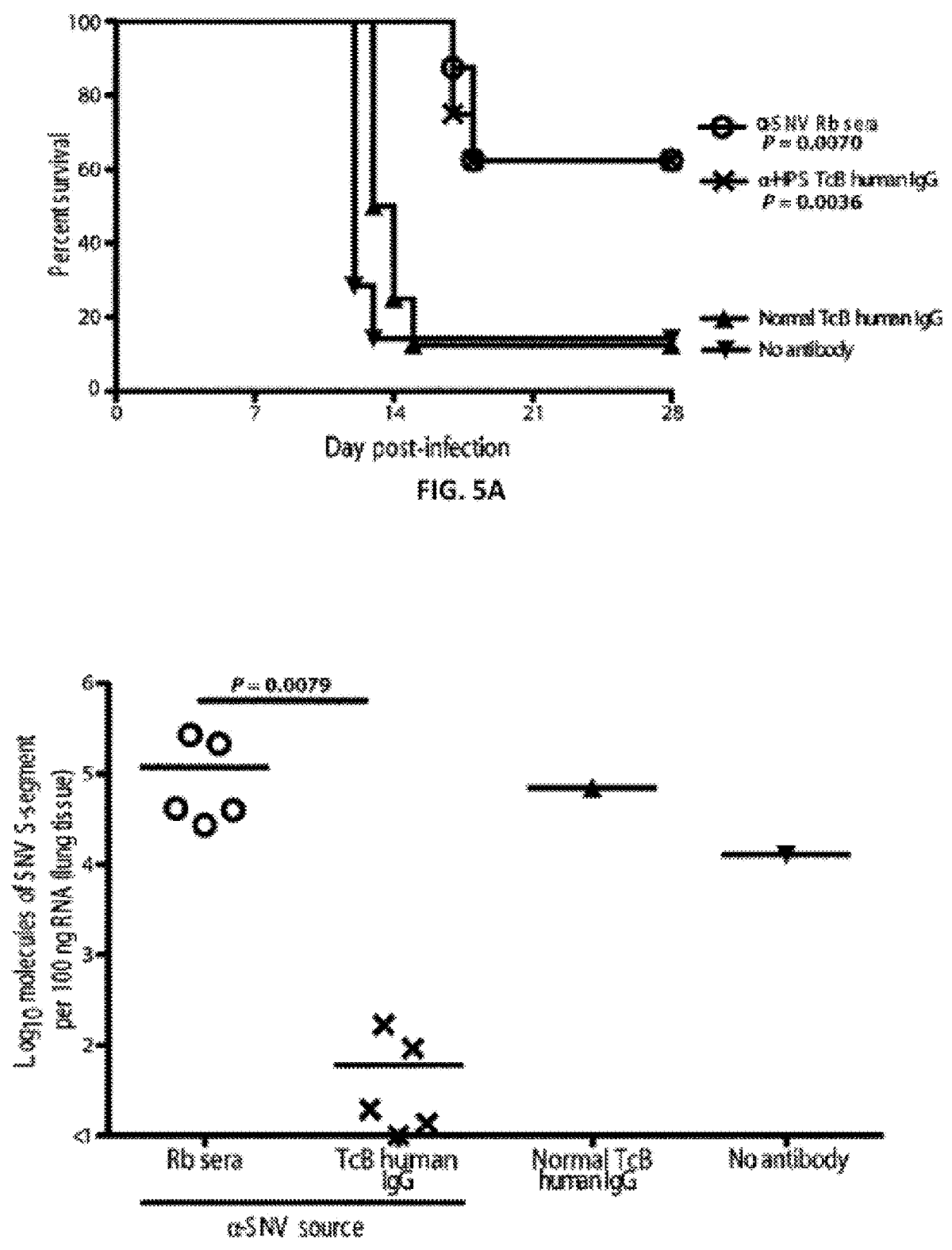

Five of eight hamsters receiving the a-HPS TcB human IgG survived (n=8; P=0.0036, Kaplan-Meier with log-rank test, when compared to normal TcB human IgG). The same survival rate was observed for the positive control group (n=8; P=0.0070, Kaplan-Meier with log-rank test, when compared to no antibody control). In contrast, seven of eight of the hamsters injected with either the normal TcB human IgG group or left untreated group succumbed. Moreover, a-HPS TcB human IgG treatment resulted in an increased mean time to death compared to normal TcB human IgG (17 to 18 days versus 12 to 15 days) (FIG. 5A). This is a statistically significant delay in death (n=8; P=0.0179, Kaplan-Meier with log-rank test, when compared to normal TcB human IgG; n=8; P=0.0157, Kaplan-Meier with log-rank test, when compared to untreated controls). The results of this experiment demonstrated that the a-HPS TcB human IgG was capable of protecting against SNV when used as a post-exposure prophylactic.

Continuous cyclophosphamide treatment precludes the hamster from mounting an antibody response to SNV infection. Therefore, lung tissue collected from surviving hamsters on day 28 was used to evaluate the levels of SNV viral genome detected by RT-PCR (FIG. 5B). Lung tissue from hamsters receiving a-SNV rabbit sera contained similar levels of viral genome as seen previously (15). Hamsters receiving a-HPS TcB human IgG had significantly reduced viral genome detected (n=5; P=0.0079, t test).

Discussion

Here, it is demonstrated that it is possible to combine DNA vaccine technology with the TcB platform to produce polyclonal human IgG specifically targeting multiple viruses. In a relatively straightforward process, it was possible to synthesize the vaccine, vaccinate the TcB, collect large volumes of plasma, and purify human polyclonal antibodies with extraordinarily potent neutralizing activity against two different viruses. Humans who have survived HPS are not required for this product, and although it is made in an animal, there is no need for a despeciation step. Using a DNA vaccine approach resulted in consistent patterns of neutralizing antibody response against ANDV and SNV as measured by both the PsVNA and PRNT.

The vaccine used to produce the human IgG in TcB is purified plasmid DNA. This approach allowed for specifically targeting the virus glycoproteins without the need to modify the proteins (such as remove transmembrane regions and produce His-tagged fusion proteins) or develop specific protocols for virus glycoprotein purification. Because a conventional killed or attenuated vaccine grown in mammalian cell culture was not used, the possibility that the product will contain antibodies against cell culture contaminants was eliminated. The same DNA vaccine plasmids (pWRG/AND-M[opt2] and pWRG/SN-M[opt]) used in this process are advancing toward clinical trials as an active vaccine for HPS. The flexibility of the DNA vaccine/TcB platform allows for the rapid design and development of human polyclonal formulations against multiple viruses as long as the DNA vaccine elicits high-titer neutralizing antibodies.

The PharmaJet IMStratis device was recently shown to effectively deliver hantavirus DNA vaccines to both rabbits and nonhuman primates. Here, DNA vaccination of the TcB using the Stratis device elicited high-titer neutralizing antibodies to two viruses after the second vaccination. This device is FDA 510(k)—cleared and can be used in the field without the need for an electric or compressed gas power source. Moreover, the vaccination procedure is relatively painless, and the animals did not need to be anesthetized before vaccination. It is possible that other means of DNA delivery, such as intramuscular electroporation, could also generate even higher levels of neutralizing antibody titers. Also, the ISA 206/Quil A adjuvant was used for a single vaccination in this study. The increased titer after that boost suggests that this veterinary use adjuvant has the potential to significantly enhance the immune response to DNA vaccines.

Here, the TcB human immunoglobulin (8.4 mg/ml) was dosed at 20,000 NAU/kg delivered to hamsters on days 5 and 8 after exposure. This is equivalent to 16 mg/kg for a 70 kg human. Previous work with a-ANDV FFP in the hamster model indicated that 12,000 NAU/kg was a conservative protective dose. It can be predicted that if 12,000 NAU/kg is sufficient to confer clinical benefit, then a dose as low as 9.6 mg/kg might be effective. The TcBs used in this study produced 68% (TcB #1) and 79% (TcB #2) fully human IgG before purification. Purification increased the percent of fully human IgG to 97%. The manufacturing process for TcB-derived human IgG to be used in preclinical studies and future clinical studies includes a polishing step (Q Sepharose chromatography) to remove residual bovine IgM from the final Tc human IgG product. TcB produces fully human IgG (up to 15 g/liter), and 30 to 60 liters of plasma can be collected per animal per month. This platform can be scaled by the addition of animals depending on need. It is expected that optimization of vaccine dose, delivery, schedule, and adjuvant formulation will increase the potency of the product. Also, further manipulation of the TcB genome by additional gene transfer and/or the insertion of mutations in the Fc might increase not only levels of fully human IgG but also IgG half-life (41).

As with any antiviral treatment, it is important to control for nonspecific protection attributable to the innate immune response. Here, normal purified TcB human immunoglobulin was included as a control in both the ANDV and SNV challenge experiments. This material was collected, before vaccination, from the same animal used to produce the a-ANDV TcB human immunoglobulin. Ideally, the amount and isotype of immunoglobulin would be identical in the test article and control in a passive transfer experiments. However, because the amount of residual IgM in the control sample (0.84%) was less than that in the a-HPS TcB human immunoglobulin (3.07%), the possibility cannot be ruled out that residual IgM could trigger a difference in the innate response to the treatment. There was no significant protection conferred by the control antibody in either the ANDV or SNV challenge experiments. The late time point (day 5) when a-HPS TcB human immunoglobulin was first administered makes it unlikely that the innate immune response contributed to the observed protection. Even strong inducers of innate immunity fail to protect hamsters against lethal HPS caused by ANDV if administered later than 3 days after challenge. For example, a VSV-vectored Ebola vaccine elicited a protective innate immune response that protected hamsters against lethal HPS caused by ANDV, but only if administered on day 3 or earlier. Conversely, administration of the vaccine on day 5 or later did not protect hamsters from lethal HPS (44). One limitation of this study was that the mechanism of protection against HPS in the hamster model was not addressed. Although it was demonstrated that the purified TcB-derived IgG has potent ANDV and SNV neutralizing activity in vitro, serial blood collections were not performed to measure the effects of antibody treatment on viremia, and serial pathology experiments were not performed to monitor evidence of disease. The onset of viremia is dependent on the route of virus challenge. After intramuscular challenge, viremia is detected on day 6 and the mean day to death is day 11 (45), whereas after intranasal challenge, viremia is detected later and the mean day to death is day 17 (16). Consistent with differences in the onset of viremia, passive transfer of antibody protected against intramuscular challenge if antibody was administered starting on day 5 or earlier, whereas after intranasal challenge, passive transfer was successful when starting later (day ≤8) (11, 14, 16). On the basis of these findings, it was hypothesized that the polyclonal neutralizing antibody administered before viremia confers protection by limiting or delaying widespread dissemination of virus to the endothelium. The most likely mechanism of in vivo neutralization is the binding of the antibodies to the virus envelope glycoproteins, preventing entry into target cells. For potential licensure under Animal Rule, determining the pathophysiological mechanism through serial pathology experiments will likely be required.

Although this proof-of-concept work targeted HPS, the implications are more wide-ranging. DNA vaccines eliciting protective antibodies to many infectious agents and toxins have been reported. Our work indicates that it is possible to combine this class of vaccine with the TcB platform to produce purified fully human IgG with functional activity (such as neutralizing antibodies), capable of conferring protection in lethal disease models when administered after exposure. Many of the polyclonal antibody-based products that are currently licensed target infectious diseases and toxins for which DNA vaccines have been described. The combination of these DNA vaccines and the TcB platform might allow the production of protective human IgG products without the need for human donors, heterologous animal species, or conventional yet more cumbersome vaccine methodology.

Example 2

In this example, human antibodies to two Ebola virus strains were produced via TC bovine. That is, the TC bovine were immunized with the two Filovirus strains.

DNA vaccination of transchromosomal bovines (TcBs) with DNA vaccines expressing the codon-optimized (co) glycoprotein (GP) genes of Ebola virus (EBOV) and Sudan virus (SUDV) produce fully human polyclonal antibodies (pAbs) that recognize both viruses and demonstrate robust neutralizing activity. Each TcB was vaccinated by intramuscular electroporation (IM-EP) a total of four times and at each administration received 10 mg of the EBOV-GPco DNA vaccine and 10 mg of the SUDV-GPco DNA vaccine at two sites on the left and right sides, respectively. After two vaccinations, robust antibody responses (titers >1000) were detected by ELISA against whole irradiated EBOV or SUDV and recombinant EBOV-GP or SUDV-GP (rGP) antigens, with higher titers observed for the rGP antigens. Strong, virus neutralizing antibody responses (titers >1000) were detected after three vaccinations when measured by vesicular stomatitis virus-based pseudovirion neutralization assay (PsVNA). Maximal neutralizing antibody responses were identified by traditional plaque reduction neutralization tests (PRNT) after four vaccinations. Neutralizing activity of human immunoglobulins (IgG) purified from TcB plasma collected after three vaccinations and injected intraperitoneally (IP) into mice at a 100 mg/kg dose was detected in the serum by PsVNA up to 14 days after administration. Passive transfer by IP injection of the purified IgG (100 mg/kg) to groups of BALB/c mice one day after IP challenge with mouse adapted (ma) EBOV resulted in 80% protection while all mice treated with non-specific pAbs succumbed. Similarly, interferon receptor 1 knockout (IFNAR −/−) mice receiving the purified IgG (100 mg/kg) by IP injection one day after IP challenge with wild type SUDV resulted in 89% survival. These results demonstrate that filovirus GP DNA vaccines administered to TcBs by IM-EP can elicit neutralizing antibodies that provide post-exposure protection.

Additionally, these data describe production of fully human IgG in a large animal system, a system which is capable of producing large quantities of a clinical grade therapeutic product.

TcBs genetically engineered to have the bovine heavy and lambda light chain loci knocked out and to express the entire non-rearranged human immunoglobulin heavy-chain and kappa light-chain loci from a human artificial chromosome are capable of producing large amounts of fully human antigen-specific polyclonal antibodies (pAbs). As such, the generated IgG products overcome the significant limitation associated with IgG products obtained from other animal sources including toxicity upon repeated administrations as well as reduced antibody half-life due to clearance by the human host. Here, EBOV and SUDV DNA vaccines were delivered by IM-EP to TcBs as a means of generating a fully human candidate polyclonal IgG product for these filoviruses. Studies were also performed to characterize the virus-binding and virus-neutralizing activity of these pAbs and to evaluate their ability to passively protect mice from otherwise lethal challenges with EBOV and SUDV.

Materials and Methods

DNA Vaccines

DNA vaccines expressing codon-optimized GP genes of EBOV and SUDV (EBOV-GPco, SUDV-GPco) were generated as previously described (Grant-Klein R J, Van Deusen N M, Badger C V, Hannaman D, Dupuy L C, Schmaljohn C S. A multiagent filovirus DNA vaccine delivered by intramuscular electroporation completely protects mice from ebola and Marburg virus challenge. Human vaccines & immunotherapeutics. 2012; 8(11):1703-6). Briefly, these genes were synthesized by GeneArt and cloned into the NotI and BglII restriction sites of the pWRG7077 eukaryotic expression vector. Research grade plasmids were manufactured by Aldevron (Fargo, N. Dak.).

Transchromosomal Bovines (TcBs)

The TcBs used in this study are triple knockouts for the endogenous bovine immunoglobulin genes, (bIGHM–/–, bIGHML1–/–, bIGL–/–), and contain a human artificial chromosome (HAC) vector labeled KcHACD. This HAC vector expresses fragments of human chromosome (HC) 14 and HC 2. The HC 14 fragment contains the entire human immunoglobulin heavy chain locus with the exception of the immunoglobulin heavy constant mu (IGHM) region which remains bovine. The HC 2 fragment contains the human immunoglobulin kappa light-chain (Igk) locus.

TcB Vaccinations

As set forth in Table 2 below, two TcBs were vaccinated with both the EBOV-GPco DNA vaccine and the SUDV-GPco DNA vaccine by IM-EP using the TriGrid Delivery System (TDS; Ichor Medical Systems) at 3-4 week intervals as previously described (van Drunen Littel-van den Hurk S, Luxembourg A, Ellefsen B, Wilson D, Ubach A, Hannaman D, et al. Electroporation-based DNA transfer enhances gene expression and immune responses to DNA vaccines in cattle. Vaccine. 2008; 26(43):5503-9. doi: 10.1016/j.vaccine.2008.07.093 PMID: 18708108). Briefly, TcBs were anesthetized with a mixture of xylazine and ketamine, the TriGrid electrode array with 8-mm spacing containing a 22 gauge syringe loaded with a 1 ml DNA solution inserted through the central injection port was inserted either on the neck or on the hind leg, and the automatic injection device was activated. Following DNA injection a 250 v/cm electrical field was applied locally for a total duration of 40 ms over a 400 ms interval. The EBOV-GPco DNA vaccine was administered on the left side of each animal while the SUDV-GPco DNA vaccine was administered on the right side of each animal. Both vaccines were administered at 5 mg/ml for a total dose of 10 mg/vaccine/TcB vaccination. To enhance the immune responses, SAB's proprietary adjuvant formulation (SABadj-1) was injected at sites adjacent to the DNA vaccination sites by standard IM injection. The adjuvant formulation was administered in a 1-ml volume.

TABLE 2

| TC Bovine | Vaccination | Vaccine Formulation |
|---|---|---|
| #2295; #2303 | V1 to V4 at 3-4 week intervals | EBOV-Zaire Vaccine (95): 10 mg plasmid (left side) + Adjuvant SUDV Vaccine: 10 mg plasmid (right side) + Adjuvant |

Purification of Fully Human IgG

Plasma collected from both TcBs prior to the first vaccination was the source material for the fully human negative control pAbs. Plasma collected from each vaccinated TcB on day 8 following the third vaccination was the source material for the fully human EBOV/SUDV pAbs used in the challenge studies though human EBOV/SUDV pabs purified from plasma collected from each vaccinated TcB on day 8 following the fourth vaccination was also analyzed by in vitro assays. Purified IgG was obtained from the plasma using a known process. Briefly, frozen plasma was thawed overnight at 25° C., pooled, and the pH adjusted to 4.8 with 20% acetic acid. The plasma was then fractionated at low pH with caprylic acid followed by a filtration step using a depth filter device to remove non-IgG proteins from bovine plasma. The filtrate was then adjusted to a pH of 7.5 with 1M Tris and further purified by using human IgG light chain kappa specific affinity chromatography followed by a second purification using bovine IgG heavy chain specific affinity chromatography. The purified EBOV/SUDV IgG has a protein concentration of 22.16 mg/ml (from the third vaccination) or 36.68 mg/ml (from the fourth vaccination) in a sterile liquid containing 10 mM glutamic acid monosodium salt, 262 mM D-sorbitol, 0.05 mg/mL Tween80, pH 5.5.

Elisa

Total IgG anti-EBOV and anti-SUDV endpoint antibody titers were determined for serum samples and the purified pAbs by standard enzyme-linked immunosorbent assay (ELISA) using sucrose gradient-purified, EBOV or SUDV virions which were inactivated by gamma irradiation, or commercially available recombinant EBOV or SUDV GP (IBT Bioservices) using a known process. Briefly, recombinant GP antigens were diluted in PBS (2 µg/ml) or whole irradiated EBOV or SUDV antigens were diluted in PBS (1 µg/ml and 0.44 µg/ml) and 50 µl/well was added to polystyrene plates (Costar 3590). Plates were incubated at 4° C. overnight. Antigen was removed prior to blocking at room temperature for 2 hours with a solution of 5% milk in PBS/0.05% Tween 20. TcB serum samples or purified pAbs were diluted in blocking buffer supplemented with 1% goat serum (42.8 µg/ml) and serial 0.5-log dilutions were performed. Antigen-coated ELISA plates were incubated with diluted samples for 2 hours at room temperature and then washed with wash buffer (PBS, 0.05% Tween 20). A gamma chain-specific mouse anti-human horseradish peroxidase (HRP)-conjugated secondary antibody (mybiosource.com) was diluted in blocking buffer, added to the plates and incubated for 1 hour at room temperature. Plates were washed and an ABTS peroxidase substrate (KPL) was added for 25-30 minutes at room temperature followed by ABTS Stop solution (KPL). The optical density at 405 nm was measured for all plates using a SpectraMax M2e microplate reader (Molecular Devices). End point titers were calculated using Softmax Pro v5.4.1 (Molecular Devices).

Pseudovirion Neutralization Assay (PsVNA)

Pseudovirions (PsV) that express luciferase were prepared in HEK 293T cells as previously described by Kwilas et. al. (Kwilas S, Kishimori J M, Josleyn M, Jerke K, Ballantyne J, Royals M, et al. A hantavirus pulmonary syndrome (HPS) DNA vaccine delivered using a spring-powered jet injector elicits a potent neutralizing antibody response in rabbits and nonhuman primates. Current gene therapy. 2014; 14(3):200-10 PMID: 24867065) using the EBOV-GPco and SUDV-GPco DNA vaccine plasmids to express the filovirus GPs. Serum samples collected from the vaccinated TcBs were heat inactivated at 56° C. for 30 min and then an initial 1:10 dilution of the heat inactivated sera or purified material was made followed by fivefold serial dilutions. Samples were diluted in complete Eagle's minimum essential medium with Earle's salts (cEMEM) containing 10% heat inactivated FBS, 10 mM Hepes (pH 7.4), 100 IU/ml penicillin, and 100 µg/ml streptomycin and analyzed in triplicate. An equal volume of cEMEM supplemented with 10% human complement (Sigma) containing 4000 focus-forming units of each filovirus PsV was added to the sera dilutions and incubated overnight at 4° C. Following incubation, Vero cell monolayers seeded in flat, clear bottom black-walled 96-well plates (Corning) were inoculated with 50 µl of the PsV: TcB serum mixture and incubated at 37° C. for 18-24 hours. The medium was discarded, the cells were lysed, and luciferase substrate was added according to the Renilla Luciferase Assay System protocol (Promega #E2820). The luciferase data were acquired using a Tecan M200 Pro microplate reader. The raw data were graphed using GraphPad Prism (version 6) to calculate percent neutralization. The data were fit to a four-parameter logistic curve and the PsVNA80 neutralization titers were interpolated.

Plaque Reduction Neutralization Test (PRNT)

Serum samples collected from the vaccinated TcBs were heat inactivated at 56° C. for 30 min and serum or purified samples were diluted to a working concentration of 2 mg/ml. Initial 1:5 dilutions of the samples were made followed by two-fold serial dilutions. Samples were diluted in complete Eagle's minimum essential medium with Earle's salts containing 2% heat inactivated FBS and 0.05% Gentamicin and analyzed in duplicate. An equal volume of cEMEM supplemented with 10% guinea pig complement (Cedarlane) containing 100 pfu of EBOV or SUDV was added to the sera dilutions and incubated at 37° C. for 1 hour. Following incubation, Vero or Vero E6 cell monolayers were inoculated, overlaid with agarose and incubated at 37° C. A second agarose overlay containing 5% neutral red was added 7 days (EBOV) or 8 days (SUDV) later and plaques were counted the next day. Neutralization titers were determined to be the reciprocal of the last dilution of serum or purified material that reduced the number of plaques by 80% compared with the virus control wells.

Viral Challenge of Mice

Female BALB/c mice (6 to 8 weeks of age) were used in all challenge experiments with maEBOV as described by Bray et. al (Bray M, Davis K, Geisbert T, Schmaljohn C, Huggins J. A mouse model for evaluation of prophylaxis and therapy of Ebola hemorrhagic fever. The Journal of infectious diseases. 1998; 178(3):651-61. PMID: 9728532). Briefly, mice were injected with 1000 pfu or 100 pfu of maEBOV diluted in PBS. Virus challenge doses were delivered by IP injection in a volume of 0.2 ml. Interferon receptor knockout (IFNAR −/−) mice (4 weeks of age) purchased from Jackson Labs (B6.12952-Ifnar1tm1Agt/Mmjax) were challenged IP with 1000 pfu of wild type SUDV (Boniface) in a volume of 0.2 ml. All challenge studies involving the use of maEBOV and SUDV were performed at USAMRIID in animal biosafety level 4 laboratories. All animal research was conducted under an IACUC approved protocol in compliance with the Animal Welfare Act, PHS Policy, and other Federal statutes and regulations relating to animals and experiments involving animals. The protocol (AP-14-031) received approval by the U.S. Army Medical Research Institute of Infectious Diseases Institutional Animal Care and Use Committee on Oct. 8, 2014. The facility where this research was conducted is accredited by the Association for Assessment and Accreditation of Laboratory Animal Care, International and adheres to principles stated in the Guide for the Care and Use of Laboratory Animals, National Research Council, 2011.

Mouse Antibody Bioavailability Study

The EBOV/SUDV pAbs were diluted in sterile PBS and delivered as single dose of 100 mg/kg in a total volume of 0.5 ml via IP injection. Prior to and at various time points after administration of the EBOV/SUDV pAbs as described in the text, submandibular blood collection was performed and sera were isolated. The serum samples were then assayed by ELISA for total anti-EBOV and anti-SUDV IgG and by PsVNA for the presence of EBOV- and SUDV-neutralizing activity.

Mouse Passive Transfer Studies

For all studies, NS pAbs or EBOV/SUDV pAbs were diluted in sterile PBS to the specified dosing in a volume of 0.5 ml and delivered via IP injection. For the first challenge study with maEBOV, groups of 10 mice (~20 g each) were administered a single injection of negative control pAbs or EBOV/SUDV pAbs at a dose of 100 mg/kg. Control mice received NS pAbs one day prior to challenge while experimental mice received EBOV/SUDV pAbs at one day pre-challenge, or one or two days post challenge with 1000 pfu of virus. In the second maEBOV challenge study, groups of 10 mice (~20 g each) were challenged with 100 pfu of virus via IP injection. Control mice received the NS pAbs at a dose of 100 mg/kg one day post challenge. Groups of experimental mice received a single injection of EBOV/SUDV pAbs at a dose of 100 mg/kg, 50 mg/kg, or 10 mg/kg starting one day post challenge. Additional groups of 10 mice received the same total doses listed above with half the dose administered one day after challenge and the second half dose administered two days after challenge. For the SUDV challenge, groups of 9 mice (~16 g each) received a single injection at a dose of 100 mg/kg of either NS pAbs one day prior to challenge or EBOV/SUDV pAbs one or two days post challenge with 1000 pfu of virus. For all challenge studies, mice were observed twice daily for clinical signs of disease for 21 days post-challenge and any animals found to be moribund were euthanized.

Statistical Analysis

GraphPad Prism software v6 for Windows (Graph, Inc.) was used to graph and conduct statistical analysis of all data. Briefly, two-way analysis of variance with Tukey's post hoc tests was used to compare ELISA and PsVNA serum titers between time points within groups; two-way analysis of variance with Sidak's post hoc tests was used to compare ELISA and PsVNA titers of purified samples between time points. Kaplan-Meier survival curve analysis and long-rank tests were performed for comparison of survival curves between groups. Probability (p) values <0.05 were considered statistically significant in all tests.

Results

Production of Human pAbs in TcBs Vaccinated by IM-EP with DNA Vaccines

Figures 6A, 6B, 6C:
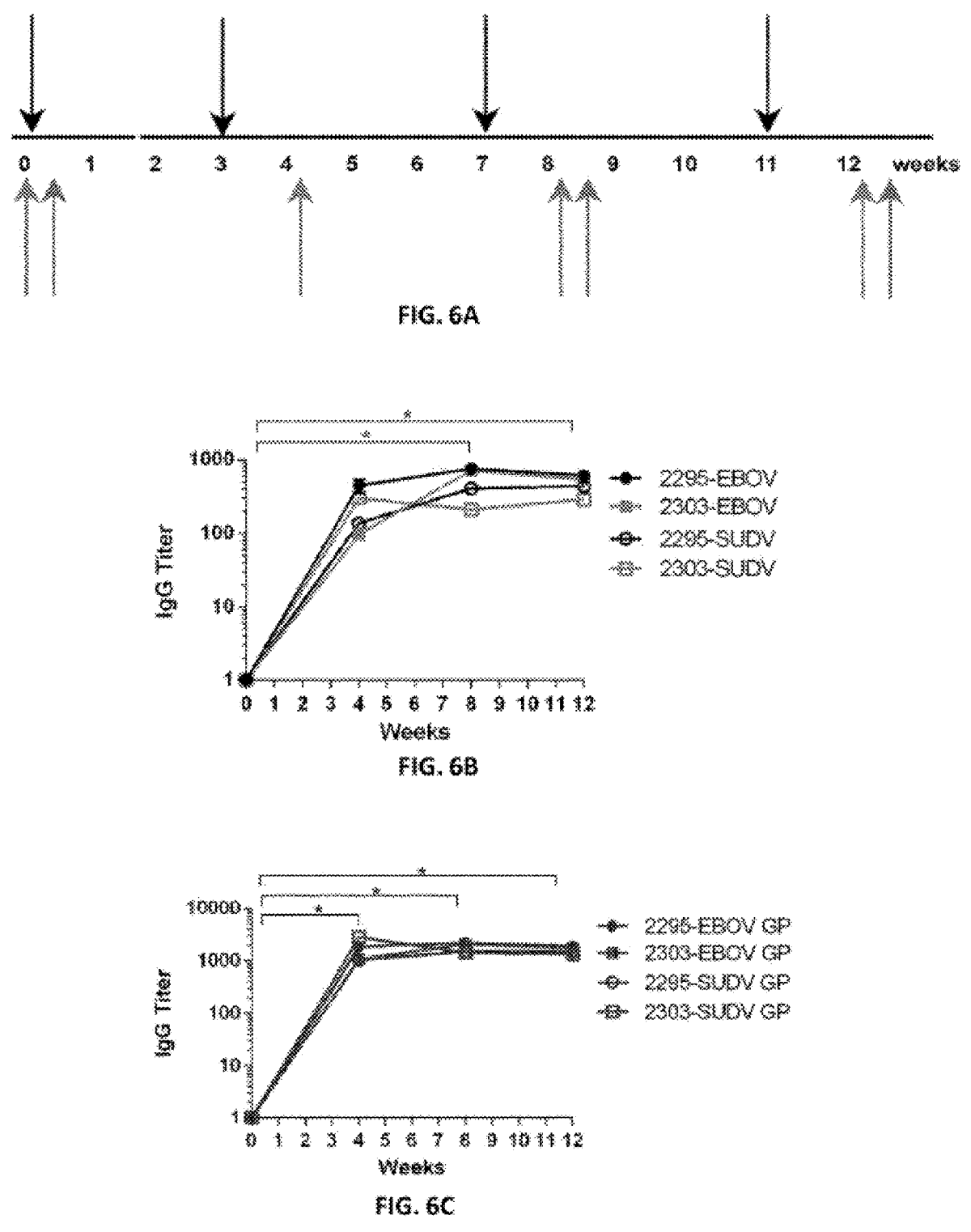

As discussed in further detail above, two TcBs (#2295, #2303) were each vaccinated four times at 3- to 4-week intervals with 10 mg each of the DNA vaccines expressing codon-optimized glycoprotein (GP) genes (EBOV-GPco, SUDV-GPco) delivered by IM-EP (FIG. 6A). Serum samples collected from each TcB prior to the first vaccination (week 0) served as negative controls for in vitro assays. Additionally, antibodies purified from large volumes of plasma collected from each TcB before the first and after the third vaccinations were used for the passive transfer studies as non-specific (NS) pAbs and EBOV/SUDV pAbs, respectively.

One week following the second vaccination (week 4), serum samples collected from each TcB displayed antibodies against EBOV and SUDV as assessed by ELISA using irradiated whole virus or recombinant EBOV-GP or SUDV-GP as antigens (FIGS. 6B and 6C). Antibody responses produced by both TcBs against EBOV- and SUDV-rGP were significantly ($p<0.0001$) higher after the second vaccination (week 4) when compared with the pre-vaccination sera controls and these titers remained significantly high (week 8 $p<0.0001$ and week 12 $p<0.0001$) in both TcBs through the fourth vaccination. Additionally, antibody responses generated in both TcBs against irradiated whole EBOV and SUDV viruses were significantly ($p<0.01$) higher after the third vaccination (week 8) when compared with pre-vaccination sera controls, and these titers remained significantly ($p<0.001$) high in both TcBs through the fourth vaccination (week 12). Maximal antibody responses generated in each TcB to the recombinant GPs were reached after the second (TcB #2303) or third (TcB #2295) vaccination but remained within the dynamic range of the ELISA as positive control human sera or the human mAb KZ52 displayed higher end point titers (data not shown).

Neutralizing Antibody Responses Generated in DNA-Vaccinated TcBs

To assess the virus-neutralizing antibody responses generated in the vaccinated TcBs, pseudovirion neutralization assays (PsVNA) were performed using vesicular stomatitis virus (VSV) pseudotyped with the GP proteins of EBOV or SUDV as well as traditional plaque reduction neutralization tests (PRNT) using a known process. Both assays provide relevant information in that the pseudovirion assay is the method used for assessing human responses in ongoing vaccine studies, while PRNT has been used in numerous past animal studies. Both TcBs generated serum neutralizing antibody responses to EBOV and SUDV (Table 3, which shows the serum neutralizing antibody responses of TcBs after vaccinations 2-4) after the second vaccination (week 4), which is congruent with the total IgG anti-GP titers. Robust neutralizing antibody responses (titers>1000), which were significantly higher than pre-vaccination control sera were detected by PsVNA in both TcBs against both EBOV (2295 $p=0.004$; 2303 $p=0.0295$) and SUDV (2295 $p<0.001$; 2303 $p=0.0009$) after the third vaccination (week 8) and these responses remained significantly higher than controls after the fourth vaccination (week 12) against EBOV (2295 $p<0.0001$; 2303 $p=0.003$) and SUDV (2295 $p=0.0001$; 2303 $p<0.0001$). Serum samples were evaluated in parallel by PRNT to confirm the results observed by PsVNA. The PRNT and PsVNA results depict similar trends with neutralizing antibody responses increasing after each vaccination, although neutralizing antibody responses detected by PRNT were much lower.

TABLE 3

| Animal ID # | PsVNA$_{80}$ Titers (EBOV/SUDV) | | | PRNT$_{80}$ Titers (EBOV/SUDV) | | |
|---|---|---|---|---|---|---|
| | Week 4 | Week 8 | Week 12 | Week 4 | Week 8 | Week 12 |
| #2295 serum | 984/522 | 3287/2696 | 4147/2259 | 10/10 | 20/20 | 160/40 |
| #2303 serum | 440/1173 | 1884/1828 | 3296/4042 | ND$^a$/20 | 10/20 | 160/80 |

$^a$ND: not detected

Characterization of Purified EBOV/SUDV Human pAbs

Figures 7A, 7B, 7C:
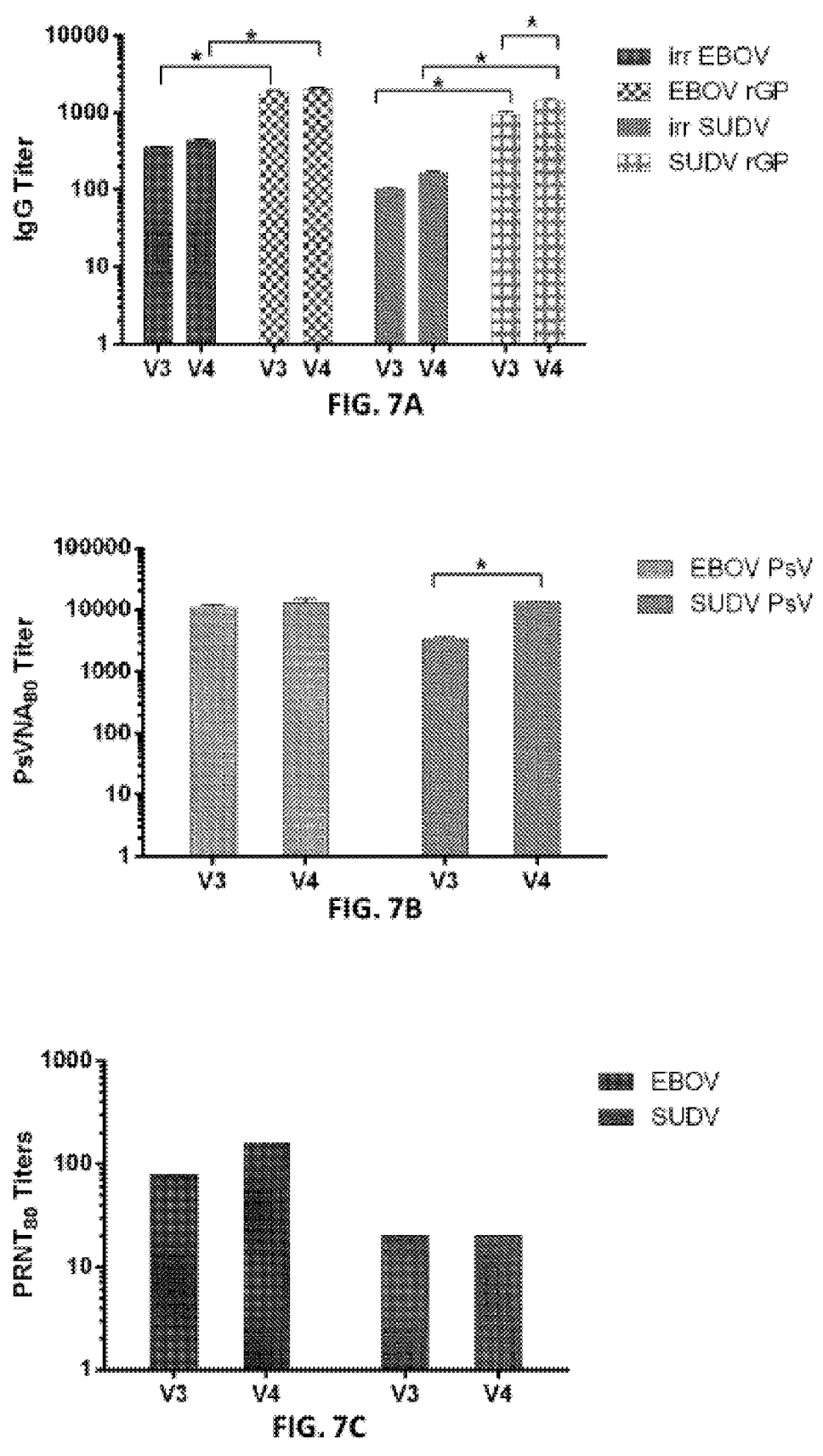

Fully human IgG was purified from large quantities of plasma collected from each vaccinated TcB eight days after the third (V3) and fourth (V4) vaccinations. The total protein concentrations of the final purified IgG preparations for the V3 and V4 materials were 22.16 mg/ml and 36.68 mg/ml, respectively. To verify the virus-binding capacity of the purified pAbs, total IgG anti-EBOV and anti-SUDV antibodies were measured by ELISA using whole-irradiated virus or rGP antigens. Consistent with the results obtained with the serum samples collected from these vaccinated TcBs, total IgG responses of the V3 and V4 EBOV/SUDV human pAb samples were significantly higher against the EBOV rGP ($p<0.0001$) and SUDV rGP ($p<0.0001$) antigens as compared to the whole-irradiated EBOV and SUDV antigens (FIG. 7A). Furthermore, the V4 EBOV/SUDV human pAbs had titers significantly ($p=0.0084$ and $p<0.0001$) higher when EBOV rGP or SUDV rGP were used as coating antigens compared to the V3 EBOV/SUDV human pAbs.

To confirm the virus-neutralizing activity of the purified V3 and V4 EBOV/SUDV human pAbs, neutralizing titers against EBOV and SUDV were determined by PsVNA and PRNT. The PsVNA80 titers of the purified V3 EBOV/SUDV human pAbs against both EBOV and SUDV were 10520 and 3260, respectively (FIG. 7B). The PsVNA80 neutralizing titers of the purified V4 EBOV/SUDV human pAbs remained relatively the same against EBOV at 12866, while the PsVNA80 titer against SUDV significantly ($p=0.0032$) increased to 14583. The PRNT80 titers of the purified V3 EBOV/SUDV human pAbs were 80 and 20 against EBOV and SUDV, respectively (FIG. 7C). The PRNT80 titers of the purified V4 EBOV/SUDV human pAbs increased to 160 against EBOV while the SUDV titer remained 20.

Bioavailability of Passively Transferred Purified Human EBOV/SUDV pAbs in Mice

Figures 8A, 8B:
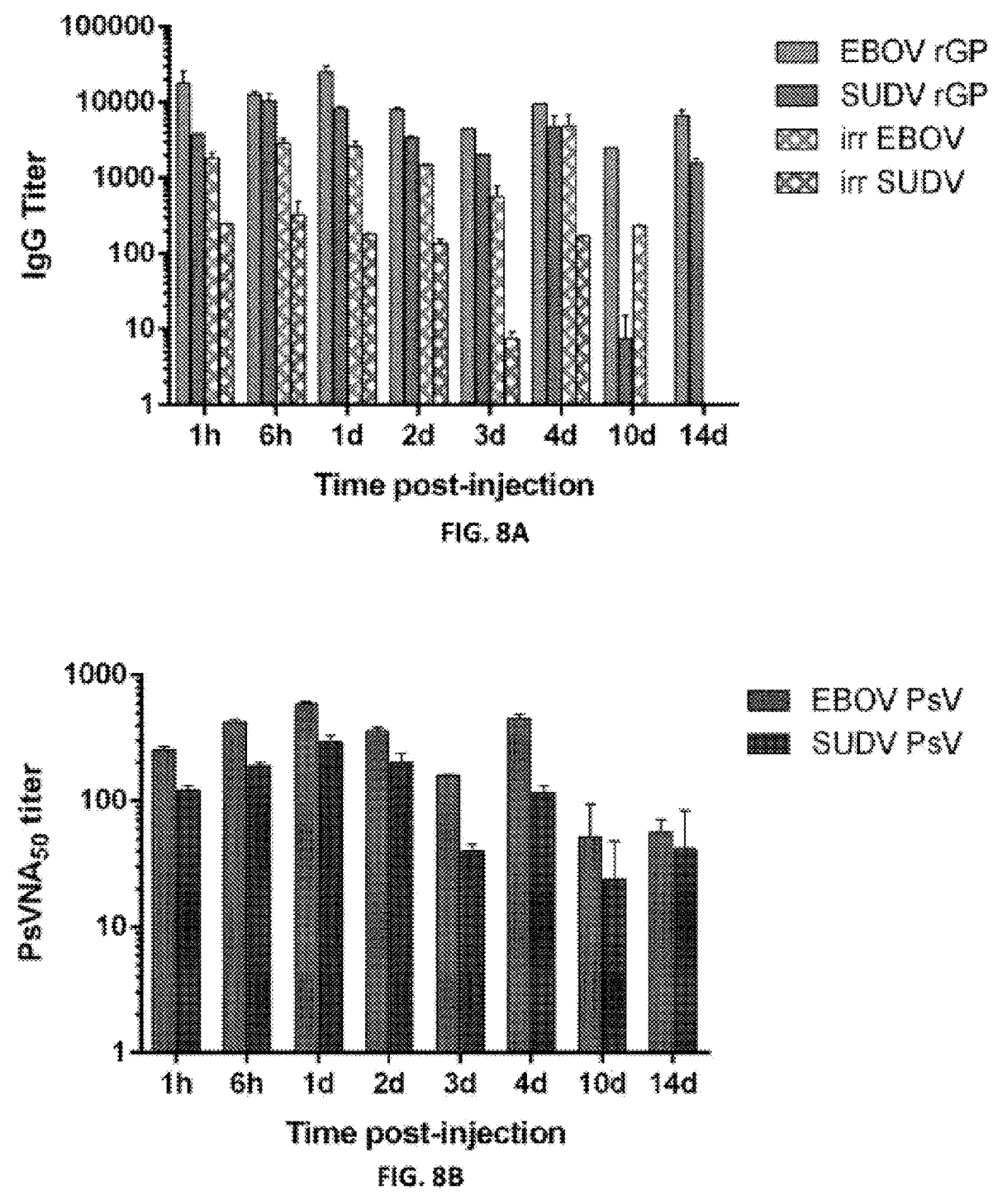

To assess the bioavailability of the purified EBOV/SUDV human pAbs in mice, 100 mg/kg of the purified V3 EBOV/SUDV human pAbs were passively transferred into mice by IP injection. Serum samples were obtained 1 h and 6 h after injection and on days 1, 2, 3, 4, 7, 10, and 14 after administration of the pAbs. The persistence of the anti-EBOV and anti-SUDV antibodies was monitored by ELISA using irradiated whole virus or recombinant EBOV-GP or SUDV-GP as antigens while neutralizing activity was monitored by PsVNA (FIGS. 8A and 8B). The purified V3 EBOV/SUDV human pAbs were detected by ELISA out to days 4 and 10 when irradiated whole SUDV or EBOV was used as the antigen, respectively. The human pabs could be detected by ELISA out to day 14 when recombinant EBOV-GP or SUDV-GP was used as the antigen. Neutralizing activity against both EBOV and SUDV peaked 24 hours after administration but could still be detected out to day 14.

Figures 9A, 9B:
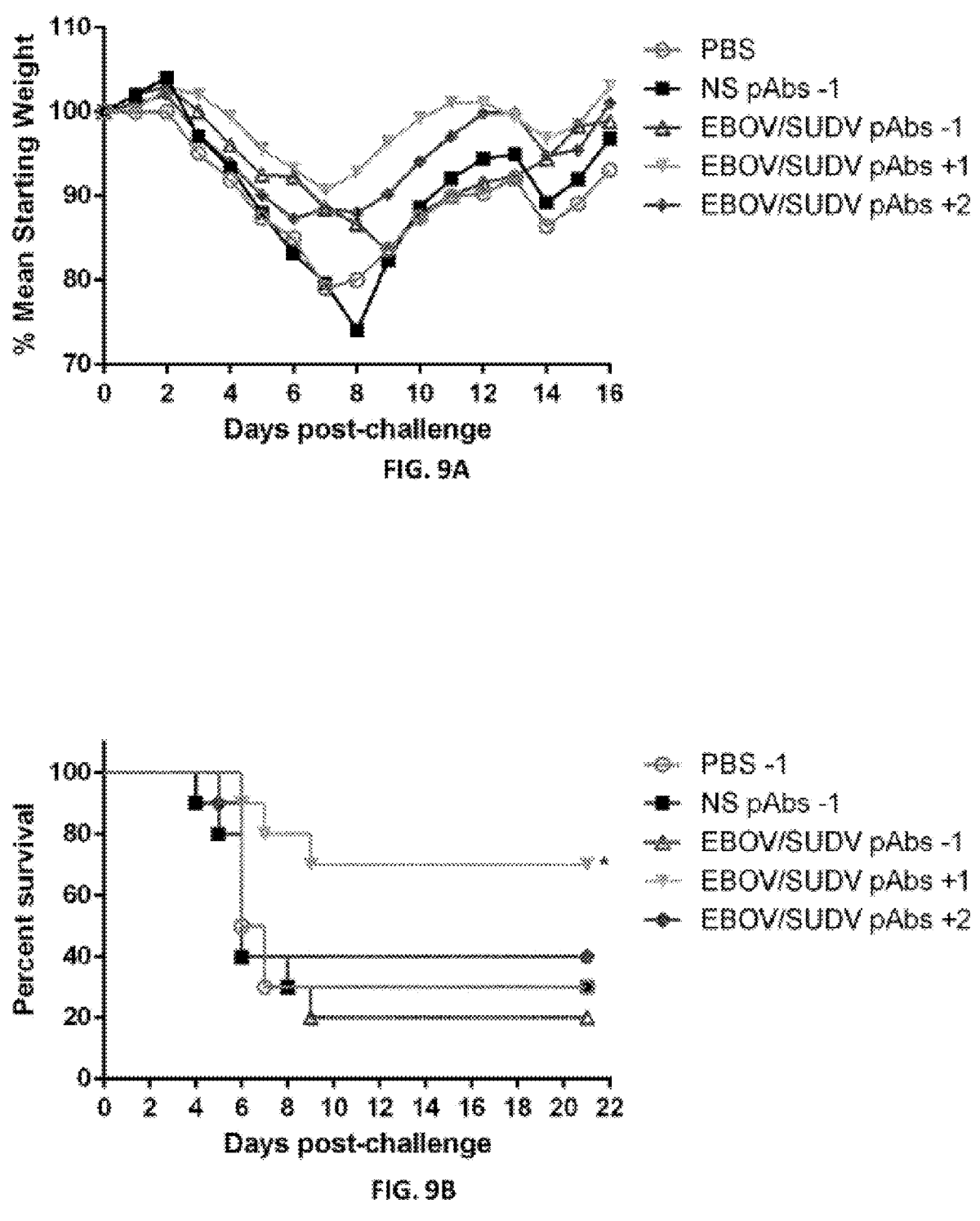

Protective Efficacy of Passively Transferred Purified EBOV/SUDV Human pAbs in Mice To assess the protective efficacy of the purified EBOV/SUDV human pAbs produced in the vaccinated TcBs against EBOV infection, groups of 6-8 week old BALB/c mice (N=10) were challenged by IP injection with 1000 plaque forming units (pfu) of mouse adapted (ma) EBOV as previously described in Bray (referenced above). Control groups of mice received phosphate buffered saline (PBS) or 100 mg/kg of NS pAbs by IP injection one day prior to challenge. Three experimental groups of mice received single 100 mg/kg doses of the purified V3 EBOV/SUDV human pAbs by IP injection one day before, one day after or two days after challenge. Mice were observed for clinical signs of EBOV infection and all mice across all groups displayed reduced grooming and subdued behavior; these clinical signs were accompanied by an increase in weight loss (FIG. 9A). Seven of the 10 mice treated with the V3 EBOV/SUDV human pAbs one day after challenge survived (FIG. 9B). There was no significant difference in the survival of control mice (30% survival in both groups) or mice receiving the V3 EBOV/SUDV antibodies one day before (20% survival) or two days after (40% survival) challenge.

A second passive protection study was performed in mice to confirm the protective efficacy of the purified V3 EBOV/SUDV human pAbs one day after challenge and to assess the effects of reduced and serial dosing. Because of the incomplete lethality in the control groups of mice in the first study, a lower challenge dose of 100 pfu of maEBOV was also used, which has been found by others to be more uniformly lethal in BALB/c mice, possibly due to the presence of fewer defective interfering (DI) viruses in the stock. One day after challenge, groups of BALB/c mice (N=10) received a single dose of the V3 EBOV/SUDV pAbs at 100 mg/kg, 50 mg/kg, or 10 mg/kg. A control group received a single dose at 100 mg/kg of the NS pAbs. To examine the effects of sequential dosing, groups were included that received 50 mg/kg, 25 mg/kg, or 5 mg/kg of the V3 EBOV/SUDV pAbs on days 1 and 2 following challenge.

Figures 10A, 10B:
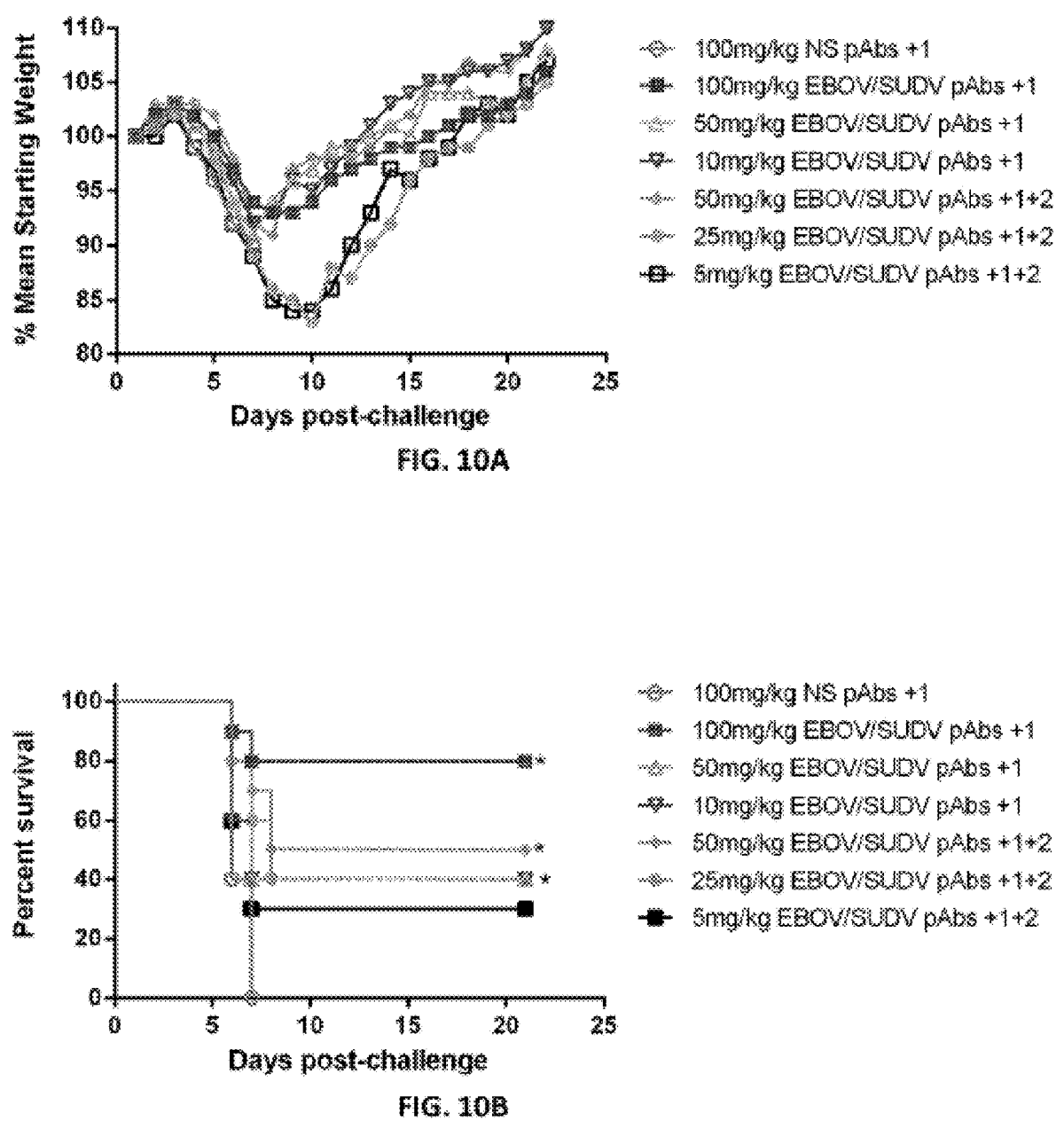

Clinical signs of EBOV infection, including weight loss, were observed beginning on days 4 or 5 in all groups of mice and by day 8 all mice receiving a 100 mg/kg dose of the NS pabs succumbed to disease (FIG. 10A). Eight of the 10 mice that received a single 100 mg/kg dose of the V3 EBOV/SUDV pAbs one day after challenge survived (FIG. 10B). Mice that received 50 mg/kg dose of the V3 EBOV/SUDV human pAbs on days 1 and 2 following challenge had a survival rate of 50%, which was significantly higher than controls ($p=0.0059$), and was not significantly less than those receiving the 100 mg/kg dose ($p=0.199$). Additionally, mice that received a single 50 mg/kg dose of the EBOV/SUDV pAbs one day post challenge or serial doses of 25 mg/kg on days one and two post challenge had a survival rate of 40%, which was also still significantly higher ($p=0.0059$; $p=0.0046$) than those receiving the NS pAbs. Mice receiving a single 10 mg/kg dose of the V3 EBOV/SUDV human pAbs one day post challenge and mice receiving serial doses at 5 mg/kg on days one and two after challenge did not have survival rates that were statistically significant when compared to mice receiving the NS pAbs.

Figures 11A, 11B:
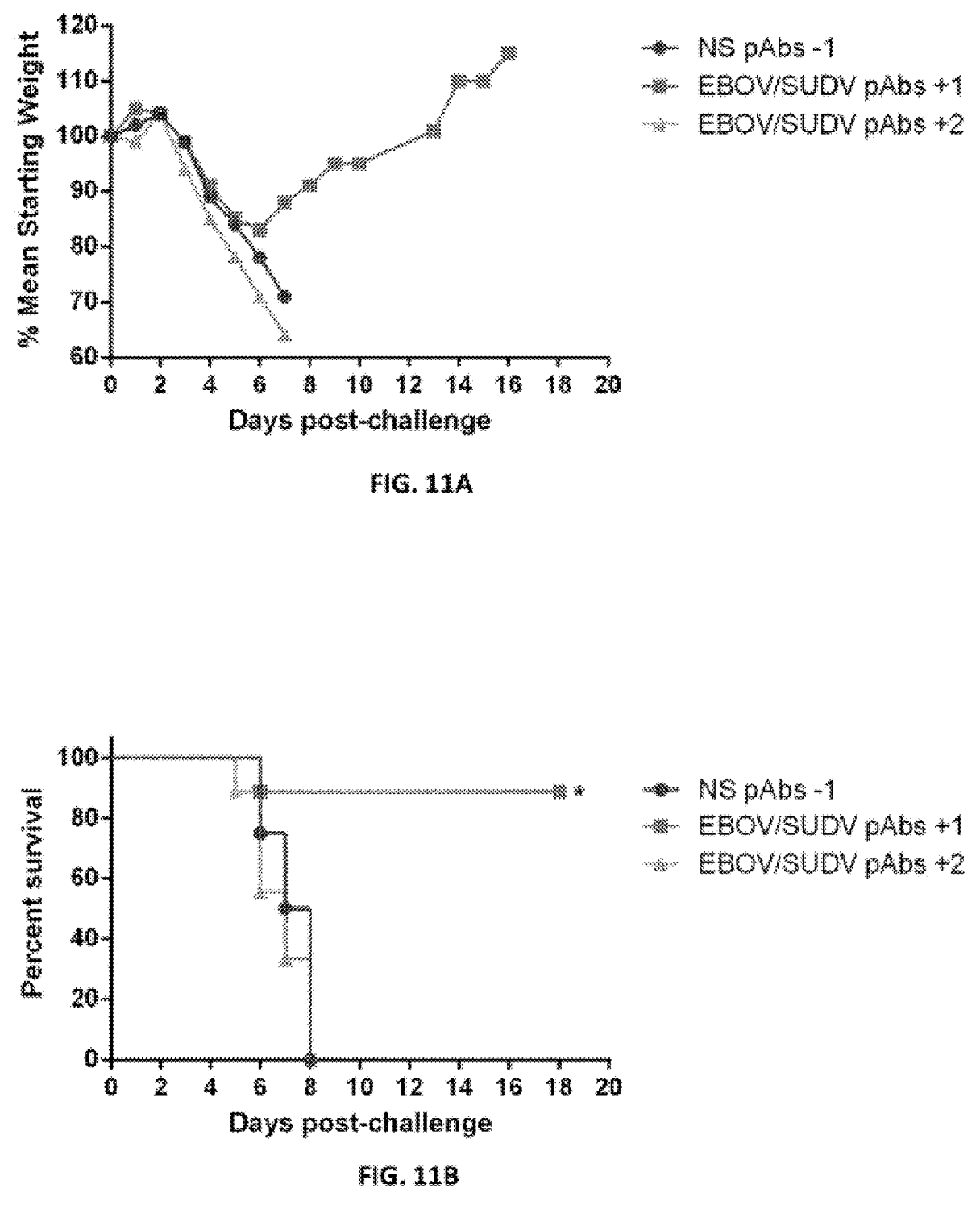

Although a mouse adapted strain of SUDV has not been reported, wild type SUDV has been shown to be lethal in interferon receptor knockout (IFNAR –/–) mice. To evaluate the protective efficacy of the purified V3 EBOV/SUDV human pAbs against SUDV challenge, groups of 4-week old IFNAR –/– mice (N=9) were challenged by IP injection with 1000 pfu of wild type SUDV. Groups received single IP injections of a 100 mg/kg dose of the V3 EBOV/SUDV human pAbs one day after or two days after challenge. A negative control group received the NS pAbs at a dose of 100 mg/kg one day before challenge. Similar to maEBOV challenge, all mice displayed clinical signs of SUDV infection, including weight loss, starting on days 4 or 5 (FIG. 11A). Eight of 9 IFNAR –/– mice treated with the purified V3 EBOV/SUDV human pAbs starting one day after challenge survived (FIG. 11B). In contrast, all mice that received the purified V3 EBOV/SUDV human pAbs two days after challenge or the NS pAbs one day before challenge succumbed.

Discussion

In the study presented here, codon-optimized EBOV and SUDV GP DNA vaccines were used to immunize two TcBs by IM-EP. The intent was to produce large quantities of a fully human polyclonal IgG product that would be suitable for immune therapy of filovirus infected humans. Within 10 weeks of initial vaccination of two TcBs, enough IgG product was produced for treatment of approximately 80 NHP, based on a 3 dose regimen. Moreover, an improved TcB genotype has been developed which has been found to produce 2-3 times the amount of purified antibody as can be recovered from the TcB genotype used for this example. For this example, both of the TcBs developed high titer antibody responses detected by ELISA and neutralizing assays. Purification of these human pAbs provided an IgG product that conferred significant post-exposure protection against lethal EBOV and SUDV challenges in mice. Thus, this approach was successful in generating a fully human filovirus-specific polyclonal antibody product.

Regarding the mechanism by which the purified IgG protects against EBOV and SUDV, without being limited by theory, it is likely that neutralizing antibodies play a role in this protection; however, it is also possible that antibodies that do not neutralize virus in cell culture play a role in protection (e.g., antibody-dependent cell-mediated cytotoxicity, antibody-dependent complement-mediated virolysis). To begin to investigate the mechanism of protection, neutralizing antibody activity was measured using two different assays, the PsVNA and PRNT. The results from both assays show a similar trend with virus neutralization titers increasing after each vaccination, although the PRNT titers are considerably lower than the PsVNA titers. The reasons for this have not been fully explored, but there are several possibilities to explain these differences. It is possible that the larger dynamic range of the PsVNA provides increased sensitivity and allows detection of inhibition by GP-mediated entry in the presence of lower antibody levels. Another possibility is that less GP-specific antibody is required to neutralize the VSV pseudovirion than EBOV virions due to their size differences. The number of GP trimers on the surface of either type of particle is unknown, but it is likely that the larger EBOV particles (~80×800 nm) have more GP displayed on their surface than the smaller VSV particles (~70×200 nm), and would require a larger quantity of antibody to achieve neutralization. One more possibility is that neutralization of live EBOV could require higher quantities of neutralizing antibodies because non-neutralized virus can replicate and spread cell to cell, while pseudovirions are non-replicating particles. Also, there are fundamental differences between how the two assays are set up that could explain the differences. For example, pseudovirions are incubated at 4° C. for 18-24 hours with test samples while EBOV is incubated at 37° C. for 1 hour. It is possible that with the shorter incubation time of the PRNT weaker neutralizing responses would not have a large enough effect on virus entry to be detected. Conversely, the longer incubation time could result in weaker neutralizing responses having more of an effect on pseudovirion entry. These and other possibilities will likely become more clearly defined as attempts are made to validate the EBOV PsVNA, which is currently being used to assess the neutralizing antibody responses of vaccines in clinical trials.

In the initial EBOV passive transfer and challenge study, reduced mortality was observed in mice treated one day after challenge with 1000 pfu of maEBOV. However, in this study, incomplete lethality of the negative controls was observed. This phenomenon has been seen in previous vaccine studies and this finding might be related to the presence of defective interfering (DI) particles in the high challenge dose. DI particles are subgenomic truncation mutants that require the parental virus to act as a helper for propagation; replication usually occurs at the expense of the infectious parental virus. DI particles occur among many RNA viruses and can modulate the disease course through attenuation of the competent virus resulting in loss of virulence. Additionally, DI particles have been shown to protect against lethal disease through modulation of the immune response and previous studies have demonstrated that EBOV DI particles are generated in cell culture. Therefore, in the follow up maEBOV challenge study, a lower challenge dose was used which was completely lethal to controls. The initial finding was confirmed that it is possible to prevent death of mice by treating them with the pAbs derived from the vaccinated TcBs one day after challenge with maEBOV. It was also showed that serial dosing spread over two days following infection was not as effective as giving a single large bolus of the pAbs.

Similar to the results with maEBOV, it was found that passive transfer of the purified EBOV/SUDV human pAbs to mice one day after infection with SUDV protected them from disease and death. However, transfer two days after challenge was ineffective. Studies by others have shown increased survival of rodents challenged with maEBOV or guinea pig-adapted EBOV when treatment with mouse mAbs was initiated at 1 or 2 days post infection rather than 1 day before infection. Taken together, these data indicate that in mice there is only a very limited treatment window available for initiation of therapy after filovirus infection.

In summary, the data presented here provide a proof of concept that filovirus DNA vaccines can be used in concert with the TcB platform to produce a safe, biologically active, fully human polyclonal IgG product that offers post-exposure protection against filovirus infection.

Example 3

In this example, human antibodies to Venezuelan Equine Encephalitis ("VEE") were produced via TC bovine. That is, the TC bovine were immunized with the VEE virus. In the current example, TC bovines have been immunized with different VEEV immunogens and the protective efficacy of purified preparations of the resultant human polyclonal antisera has been evaluated against low and high dose VEEV challenge. The example demonstrates that prophylactic or therapeutic administration of the polyclonal antibody preparations (TcpAbs) can protect mice against lethal subcutaneous or aerosol challenge with VEEV. Furthermore, significant protection can be conferred against co-infecting viral pathogens by combining individual virus-specific TcpAb preparations.

In this example, optimized immunogens (inactivated virus, expression plasmid DNA and a commercial inactivated alphavirus trivalent veterinary vaccine) have been compared for stimulation of neutralizing and protective pAb responses in Tc bovines. Subcutaneous and aerosol challenge experiments demonstrated that purified TcpAb preparations protected mice from mortality at relatively low doses (5 mg/kg) when used either prophylactically or therapeutically and the protective effect was confirmed by in vivo imaging of challenge virus replication. In addition, the inactivated virus preparation derived from wild type VEEV elicited the greatest neutralizing and most protective TcpAb responses. Finally, it is shown that the Tc bovine platform can provide significant protection to mice from lethal aerosol co-infection with multiple pathogens (VEEV and influenza virus) when TcpAb preparations are combined.

Materials and Methods

Cultured Cells.

BHK-21 cells (ATCC CCL-10) were maintained in RPMI 1640 media supplemented with 10% donor bovine serum (DBS) and 10% tryptose phosphate broth (TPB). VERO cells (ATCC CCL-81) and Huh7 cells, generously provided by Dr. Charles Rice (Rockefeller University, New York City) were maintained in DMEM supplemented with 10% fetal bovine serum (FBS). C7/10 mosquito cells, generously provided by Dr. Ilya Frolov, (University of Alabama at Birmingham, Birmingham) were maintained in DMEM supplemented with 10% FBS and 10% TPB. All media for cell lines also supplemented with penicillin (100 U/mL), streptomycin (0.05 mg/mL) and L-glutamine (0.05 mg/mL).

Viruses and Replicons.

Construction of the Venezuelan equine encephalitis virus (VEEV) Trinidad Donkey strain cDNA clone (V3000) was performed using a known process. V3000 nt3A was constructed by creating a G to A mutation at nucleotide 3 using Quick Change XL site-directed mutagenesis. The VEEV nanoluciferase reporter virus (V3000 nluc TaV) was constructed by inserting a cleavable in-frame fusion of nluc between capsid and E3 followed by the TaV 2A-like protease. This virus has a similar virulence to unmodified parental viruses in mice.

Virus stocks were generated from cDNA clones by in vitro RNA synthesis (IVT) from linearized cDNA plasmid templates using a known process. Briefly, IVT (mMessage mMachine, Ambion) was used to generate infectious, capped viral RNA genomes that were electroporated into BHK-21 or C710 cells. The supernatant was clarified by centrifugation 18-24 hours post-electroporation, and single-use aliquots were stored at −80° C. Virus stock titers were determined by standard plaque assay on BHK-21 cells.

Influenza H1N1 A/California/04/09 was obtained from BEI (NR-13658) to seed MDCK cells at an MOI of 1 and harvested 72 hours post-infection. Supernatant was clarified by centrifugation, and single-use aliquots were stored at −80° C. Virus stock titers were determined by standard plaque assay on MDCK cells. Construction and packaging of VEEV (TrD)-based eGFP replicons, generously provided by Dr. Robert Johnston (University of North Carolina, Chapel Hill) was performed using a known process. Briefly, RNA from the replicon genome along with the capsid and glycoprotein helpers were generated by IVT from linearized cDNA plasmids and co-electroporated in BHK-21 cells. Packaged replicon particles were harvested at 18-24 hrs post electroporation and clarified by centrifugation followed by concentration over 20% sucrose and resuspended in OptiMEM. For each preparation, 10% of the total volume was evaluated by serial passage on BHK-21 cells for presence of CPE to ensure that no propagation-competent viral recombinants or contaminants were present.

Transchromosomic (Tc) Bovines.

Tc bovines were produced using a known process. Briefly, the Tc bovines used in this study are homozygous for triple knock-outs in the endogenous bovine immunoglobulin genes ($IGHM^{-/-}$ $IGHML^{-/-}$ $IGL^{-/-}$) and carry a human artificial chromosome (HAC) vector labeled as isKcHACD (12-14). This HAC vector consists of two human chromosome fragments: a human chromosome 14 fragment contains the entire human immunoglobulin heavy chain locus except that the IGHM constant region remains bovine and the key regulatory sequences were bovinized; and a human chromosome 2 fragment contains the entire human immunoglobulin κ light chain locus.

Antigen Preparation.

Plasmid DNA. The DNA plasmid antigen (pDNA694) was created based on work by Dupuy et. al., the structural genes of VEEV IAB strain, Trinidad donkey (GeneBank Number: L01442), was codon optimized using GeneOptimizer® (Life Technologies) and synthesized by DNA2.0, Inc. with restriction sites EcoRI and NheI for placing into the pCAGGS expression vector in either wild type sequence or containing a 4 amino acid deletion in the capsid (aa64-68) that limits capsid protein-mediated host transcription shut off. Bulk preparation of plasmid DNA for bovine immunization was produced by DNA 2.0 and expression of antigen was confirmed by western blot (not shown).

Inactivated virus (V3000 nt3A AMT). VEEV V3000 nt3A virus was generated from electroporation of the C7/10 mosquito cell line as described above and then purified by discontinuous sucrose gradient. Virus was inactivated using 10 ug/mL of the psoralen derivative 4'-aminomethyltrioxsalen (AMT) (Sigma) with 10 min UV inactivation ($\geq 13$ $J/cm^2$). Virus was considered inactivated if no plaques were detected by plaque assay, no cytopathic effect was observed after inactivated material was co-cultured with BHK cells, and no morbidity or mortality was observed after intracranial injection of undiluted material into interferon alpha/beta/gamma receptor-deficient mice.

Immunization of Transchromosomic Bovines.

Commercial livestock vaccine (CLV). Two Tc bovines (#2180; #2221) were immunized with a licensed animal vaccine containing inactivated VEEV, EEEV and WEEV (encephalomyelitis vaccine; Intervet) at two times the recommended equine doses (2 mls) for V1 and V2 and at four times the recommended dose for V3 (4 mls). To enhance the immune responses, an SAB proprietary adjuvant formulation (SAB-adj-2) was multiply injected adjacent to the licensed animal vaccine vaccination sites.

Plasmid DNA. Two Tc bovines (#2184; #2186) were immunized with VEE pDNA694 DNA vaccine at 10 mg per animal per vaccination by intramuscular-electroporation (IM-EP) using the TriGrid Delivery System (TDS; Ichor Medical Systems) using a known process. One ml of SAB-adj-1 was multiply injected adjacent to the DNA vaccination sites using a needle and syringe. The Tc bovines in both groups were vaccinated 5 times (V1-V5) at 3 week intervals.

Inactivated VEEV nt3A. Two Tc bovines (#2178 and #2183) were immunized with inactivated V3000 nt3A AMT at $1 \times 10^8$ pfu/dose formulated with SAB-adj-2. The Tc bovines in both groups were vaccinated 5 times (V1-V5) at 3 week intervals.

As set forth in Table 4 below, inactivated influenza virus Two Tc bovines (#2186 and #635) were immunized with a licensed 2012-2013 tri-valent seasonal influenza vaccine (Fluzone TIV—Sanofi-Pasteur containing A/California/07/2009 (H1N1), A/Victoria/361/2011 (H3N2), and B/Texas/6/2011 [B/Wisconsin/1/2010-like]) at total 1 mg of HA/dose formulated with SAB-adj-2. The Tc bovines were vaccinated 4 times (V1-V4) at 3 week intervals.

TABLE 4

| TC Bovine | Vaccination | Vaccine Formulation |
|---|---|---|
| #2178; #2186 | V1 to V5 at 3 week intervals | VEE Vaccine: 2 × 5 mg plasmid (both sides of hind legs) + Adjuvant |

Plasma collection and human immunoglobulin production. Prior to the first immunization (V1), plasma was collected from each Tc bovine as the negative control. Hyperimmune plasma (up to 2.1% of the body weight of each cow) was collected from immunized Tc bovines 10 days after each vaccination starting from the second immunization (V2) to the fifth immunization (V5). Plasma was collected using an automated plasmapheresis system (Baxter Healthcare, Autopheresis C Model 200). Plasma samples were stored frozen at −80° C. until purifications were performed. The frozen Tc plasma bags were thawed at room temperature (RT) overnight and equal volumes of plasma from each Tc bovine within a group at the selected time point were pooled. Samples were then pH adjusted to 4.80 with dropwise addition of 20% acetic acid, fractionated by caprylic acid at a caprylic acid/total protein ratio of 1.0 for 30 minutes at RT, and then clarified by centrifugation at 10,000× g for 20 minutes at RT. The supernatant containing IgG was then neutralized to pH 7.50, filtered by a 0.22 μm filter, and affinity purified by an anti-human IgG light chain specific column, KappaSelect (GE Healthcare Life Sciences). Residual bovine IgG in the KappaSelect-purified IgG sample was then removed by passing through an anti-bovine IgG heavy chain specific affinity column, Capto HC15 (GE Healthcare Life Sciences). The Capto HC15 column flow thru that contains fully human IgG was then formulated by a Millipore Labscale tangential flow filtration (TFF) System. The final purified fully human IgG was in a buffer at a pH of 5.5 consisting of 10 mM of glutamic acid monosodium salt, 262 mM of d-sorbitol, and 0.05 mg/mL of Tween 80. The purified hIgG was sterile-filtered with 0.22 μm filter. Analysis of purified IgG product by HPLC size exclusion chromatography indicated that there were no IgG aggregates or IgG dimers (not shown).

Infectivity Reduction Neutralization Test (IRNT). V3000 eGFP propagation-incompetent replicons were diluted in virus diluent (PBS-1% DBS) and reacted with bovine or mouse serum for 1 hr at 37° C. before being used to infect 24-well plates of VERO cells for 1 hr at 37° C. Culture media was added to the cells and the cells were incubated for 24 hrs before being fixed with 4% PFA. GFP-expressing (infected) cells were then quantified on an Olympus CKX41 inverted fluorescence microscope.

ELISA. Polysorp ELISA plates were coated 50 μL/well of 2 μg/mL of antigen (either inactivated V3000 nt3A or chimeric SINV-VEEV virus (Sun et al., manuscript in prep) diluted in pH 9.0 sodium bicarbonate overnight at 4° C. Plates were blocked with PBS with 0.1% Tween-20 and 3% BSA overnight at 4° C. Bovine serum was diluted in PBS with 0.1% Tween-20 and 3% BSA and added to the plates in duplicate overnight at 4° C. A 1:2000 dilution of human IgG-HRP (KPL) was added for 1 hr at room temperature. 2,2'-azino-bis (3-ethylbenzothiazoline-6-sulphonic acid) (ABTS) was incubated with the IgG-HRP for 30-1 hr at room temperature and the reaction was stopped with 1% SDS. The plates were read at OD405 nm (Spectra Max, Molecular Devices).

Mice. All mice were housed under specific pathogen-free conditions and all experiments were conducted at ABSL-3 in accordance with AAALAC-approved institutional guidelines for animal care and used approved by the University of Pittsburgh IACUC committee.

Protection conferred by transchromosomic polyclonal antibody (TcpAb). Six-week-old Balb/c mice (Charles River Laboratories) received 100 μg TcpAbs intraperitoneally or 100 μg intraperitoneally and 100 μg intranasally either prophylactically or therapeutically as described in figure legends. Mice were challenged either subcutaneously with 1000 PFU of V3000-derived virus in the rear footpad or via aerosol with either 50-100 LD50 or >100 LD50 of V3000 (GraphPad PRISM Software) was used to determine statistical significance differences in percent survival. A one tailed Student's t test (Microsoft Excel) was used to determine statistical significance for all other experiments.

Results

Tc bovines hyperimmunized with VEEV-antigens produce VEEV-specific antibodies.

Tc bovines were immunized up to five times with VEEV-specific antigens (Table 5) in a twelve-week period and serum was collected for analysis of VEEV-specific antibodies. In order to determine if the choice of antigen used to generate the VEEV-specific human pAbs resulted in pAbs of varying efficacy, Tc bovines were immunized with one of three different VEEV antigens: 1) the commercial livestock vaccine (CLV), a trivalent vaccine containing formalin-inactivated VEEV, EEEV, and WEEV; 2) the plasmid DNA (pDNA694) containing codon-optimized structural genes with a 4 aa deletion in capsid; and 3) the V3000 nt3A virus inactivated by treatment with the psoralen derivative, AMT, coupled with short duration UV irradiation.

TABLE 5

| Antigen | Bovine | Serum Collection[1] | | | | | | | |
|---|---|---|---|---|---|---|---|---|---|
| | | V1D21 | V2D10 | V2D21 | V3D9/10 | V3D21 | V4D10 | V4D21 | V5D10 |
| CLV | 2221 | | | | x | | | | |
| | 2180 | | | | x | | | | |
| pDNA694 | 2184 | x | x | x | x | | x | | |
| | 2186 | x | x | x | x | | x | | |
| V3000 nt3A | 2178 | x | x | x | x | x | x | x | x |
| AMT | 2183 | x | x | x | x | x | x | x | x |

[1]V = immunization D = day serum collected post immunization nLuc TAV virus. For the co-infection aerosol exposure, six week old DBA2 (Charles River) mice were exposed to a lethal dose of V3000 and A/California/07/2009 (H1N1) and treated intraperitoneally with the combined anti-VEEV/anti-Flu TcpAb preparation either prophylactically or therapeutically as described in the figure legend. All mice were weighed daily and monitored for clinical signs of disease, which was increased to twice daily upon onset of clinical signs of disease.

In Vivo Imaging (IVIS). At 5 days post-challenge, mice were injected with 10 μg Nano-Glo™ substrate (Promega) either subcutaneously (sc) or intravenously (iv) and imaged using the IVIS Spectrum CT instrument (Perkin Elmer) for either 2 min (iv) or 4 min (sc) post-substrate injection on the auto exposure setting. Images of representative animals from each group were chosen based on the animals exhibiting the greatest or least weight loss to illustrate the range of disease detected by the IVIS system. The total flux (photons/second) in the head region, taken as a measure of brain replication, was calculated for 3-4 animals in each treatment group based on the radiance (photons/second/cm$^2$/steradian) and was quantified using Living Image Software (Perkin Elmer). We demonstrated previously (27) that nLuc reporter virus signal as measured by IVIS gives similar results for virus replication to titration of plaque forming units from tissues of infected mice. In the current studies, the dynamic range of the IVIS imager signal from the heads of uninfected mice to highly infected mice is approximately one hundred-fold (~1-2×10$^5$ photons/second to ~1-2×10$^7$ photons/second, respectively).

Figure 12A:
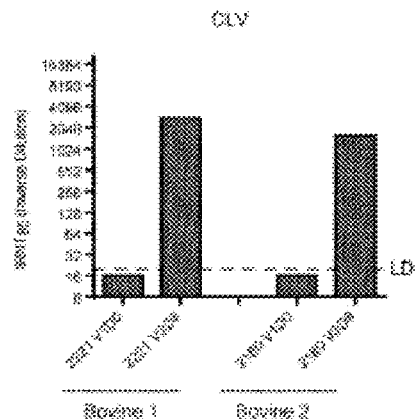
FIG. 12A shows VEEV-specific antibody responses generated by CLV hyperimmunization of transchromosomic (Tc) bovines.
Figure 12B:
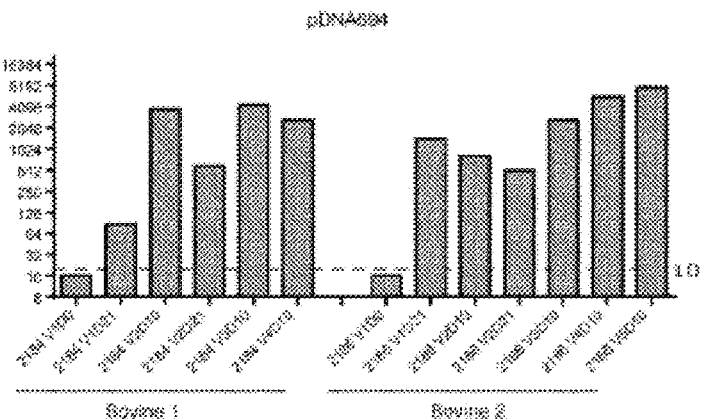
FIG. 12B shows VEEV-specific antibody responses generated by pDNA694 hyperimmunization of transchromosomic (Tc) bovines.
Figure 12C:
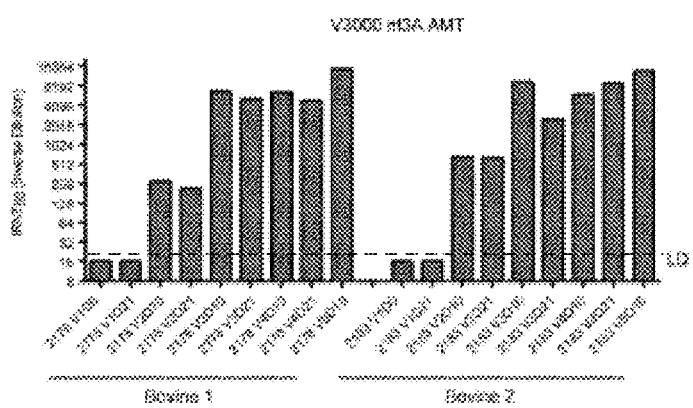
FIG. 12C shows VEEV-specific antibody responses generated by V3000 nt3A AMT hyperimmunization of transchromosomic (Tc) bovines.

Statistical Analysis. Mantel-Cox Log Rank test (GraphPad PRISM Software) was used to determine statistically significant differences in survival time while Chi Square test First, the serum was tested for VEEV-specific neutralizing antibodies (FIG. 12A-C) using an infectivity reduction neutralization test (IRNT). VEEV-specific neutralization activity was detected in the V3D9 serum of Tc bovines hyperimmunized with CLV antigen (1:2800; FIG. 12A). A more extensive time course determining when VEEV-specific neutralization could be detected was performed in Tc bovines hyperimmunized with pDNA694 (FIG. 12B) or V3000 nt3A AMT (FIG. 12C). Neutralization activity was present after the first immunization with pDNA694 but not V3000 nt3A AMT; however, further immunizations with V3000 nt3A AMT resulted in higher levels of VEEV-specific neutralization activity than in serum from Tc bovines hyperimmunized with pDNA694 (~1:14000 vs ~1:7500 respectively). It is worth noting that the CLV immunizations likely contained much more virus protein, even if only ⅓ was VEEV, than the V3000 nt3A AMT immunizations which, at ~1×10$^8$ pfu, were below the level of detection of a Bradford protein assay.

Figure 12D:
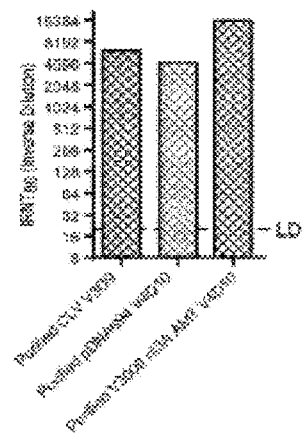
FIG. 12D shows data quantifying neutralizing antibody generated by hyperimmunization of TcBs.
Figure 12E:
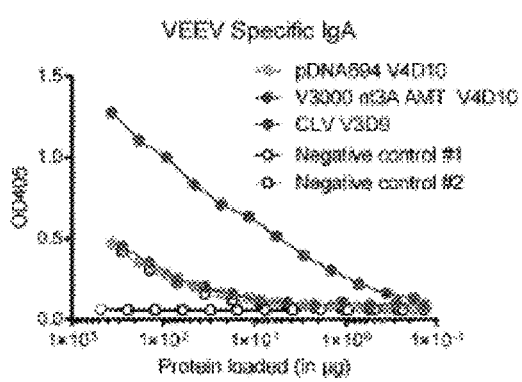
FIG. 12E shows data quantifying VEEV-specific human IgA generated by hyperimmunization of TcBs.
Figure 12F:
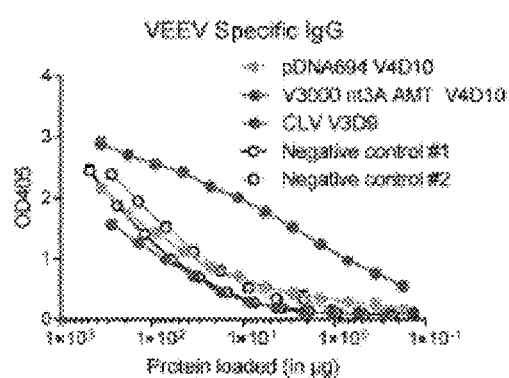
FIG. 12F shows data quantifying VEEV-specific human IgG generated by hyperimmunization of TcBs.
Figure 13A:
FIG. 13A shows exemplary data from IVIS imaging from control animals.
Figure 13B:
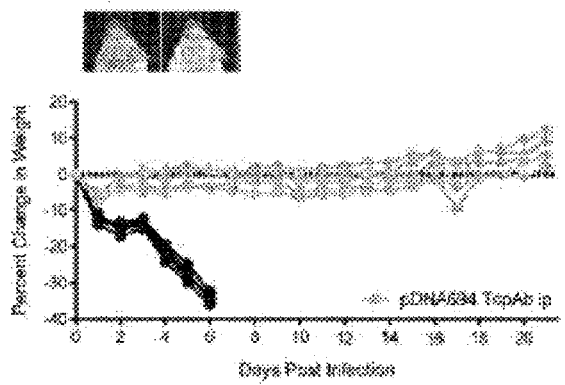
FIG. 13B shows exemplary data from IVIS imaging and clinical data from prophylactically treated animals.
Figure 13C:
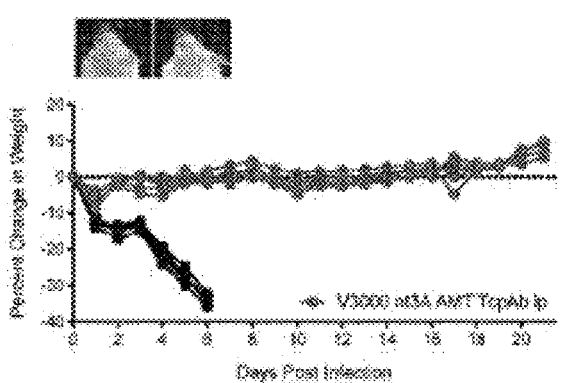
FIG. 13C shows exemplary data from IVIS imaging and clinical data from prophylactically treated animals.
Figure 13D:
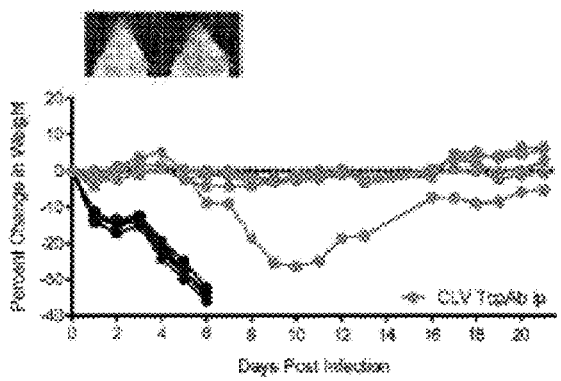
FIG. 13D shows exemplary data from IVIS imaging and clinical data from prophylactically treated animals.
Figure 13E:
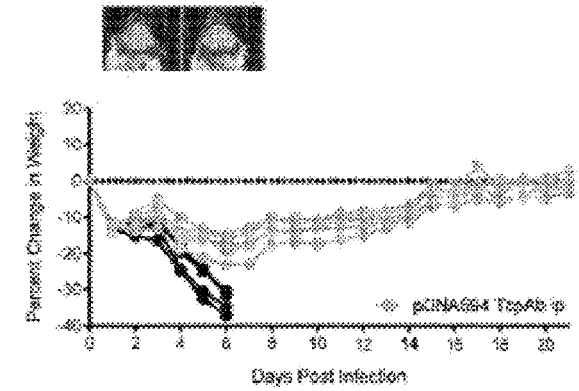
FIG. 13E shows exemplary data from IVIS imaging and clinical data from theraputically treated animals.
Figure 13F:
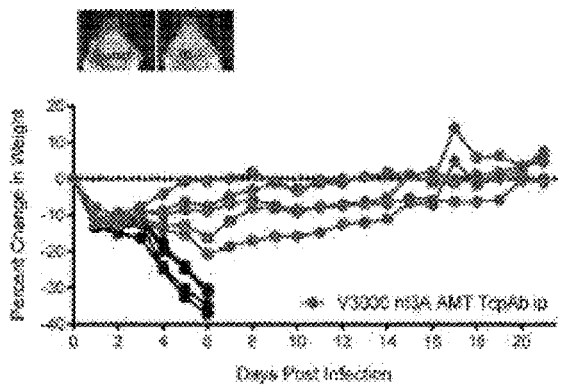
FIG. 13F shows exemplary data from IVIS imaging and clinical data from theraputically therapeutically treated animals.
Figure 13G:
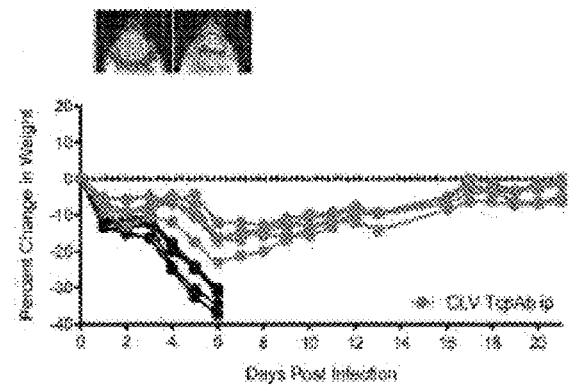
FIG. 13G shows exemplary data from IVIS imaging and clinical data from therapeutically treated animals.
Figure 13H:
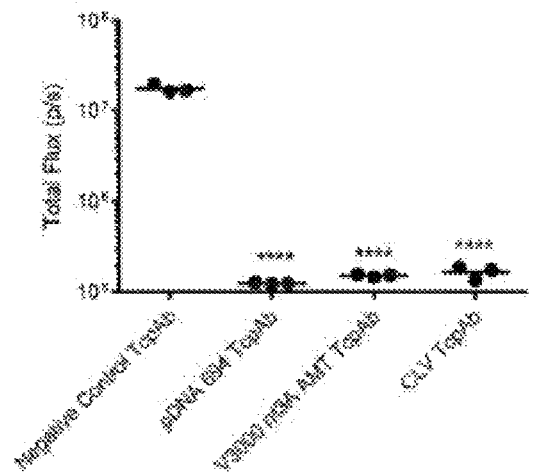
FIG. 13H shows quatification of data from the IVIS studies.
Figure 13I:
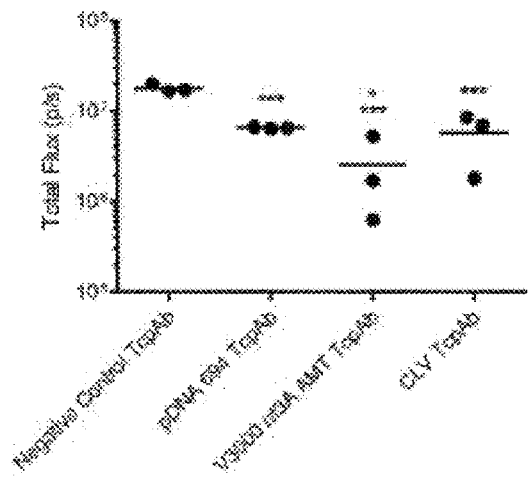
FIG. 13I shows quantification of data from the IVIS studies.

After human antibody purification from Tc bovine serum, CLV V3D9, pDNA694 V4D10 and V3000 nt3A AMT V4D10 preparations were tested for VEEV-specific neutralization activity and human IgG, and IgA levels (FIG. 12D-F). All three purified TcpAb preparations retained high VEEV-specific neutralization capacity (FIG. 12D). In the VEEV-specific ELISA, very high background was observed in the purified TcpAb pre-immunization negative control preparations and there were large differences in background between the two negative controls. The first negative control consistently exhibited lower background levels for both IgA and IgG, while the second negative control produced ELISA reactivity similar to the pDNA694-generated VEEV TcpAb preparation (FIG. 12E-F). It is possible that the Tc bovines were exposed to an ELISA cross-reactive, non-neutralizing immunogen prior to the initial VEEV immunization resulting in high background levels in the VEEV-specific ELISA. Regardless, the purified TcpAb from V3000 nt3A AMT hyperimmunized bovines had consistently higher levels of both VEEV-specific IgA (FIG. 12E) and IgG (FIG. 12F) compared to both negative controls, CLV and pDNA694 hyperimmunized bovines.

Purified VEEV TcpAbs Can Protect Against Subcutaneous Challenge

The ability of purified VEEV TcpAbs to protect against a subcutaneous challenge with single dose intraperitoneal prophylactic or therapeutic treatment was tested initially (FIG. 13). All mice who received the negative control TcpAbs succumbed to infection by 6 d.p.i. and had high levels of replication in the head region at 5 d.p.i. as determined by IVIS imaging (FIG. 13A). Virtually all mice treated prophylactically survived challenge (FIGS. 13B-D) and exhibited no clinical signs of disease, including weight loss, and did not have detectable replication in the head (as determined by IVIS). One mouse treated with the CLV TcpAb (FIG. 13D) had weight loss beginning at 6 dpi but had no detectible signs of replication in the head at 5 d.p.i. as determined by IVIS (FIG. 13H). All mice treated therapeutically with VEEV TcpAbs survived (FIG. 13E-G), but exhibited clinical signs of disease, including weight loss, and virus was detectable at 5 d.p.i. in the heads of all mice imaged (FIG. 13I). The level of IVIS signal in mice treated with anti-VEEV TcpAbs therapeutically was significantly less (p<0.001) when compared to negative control TcpAb group (FIG. 13I). When comparing the different anti-VEEV TcpAb therapeutic groups, the V3000 nt3A-derived TcpAb mice had less IVIS signal in the head than the pDNA694 TcpAb group (p<0.05) but not the mice treated with CLV-derived TcpAbs (FIG. 13I). These data indicate that all three VEEV TcpAbs could prevent measureable disease in nearly all mice after a lethal VEEV sc challenge with prophylactic treatment, however, therapeutic treatment could prevent death but not protect from disease.

Purified VEEV TcpAbs Can Protect Against Aerosol Challenge

Aerosol exposure is more likely to occur in the context of bioweapons use and represents a more stringent route of challenge with VEEV as compared with sc infection. Therefore, this route was used to determine if there was a difference in efficacy between the different anti-VEEV TcpAb preparations. Considering the difficulty in protecting from VEEV aerosol exposure, it was decided to treat the mice with TcpAb by two different routes: intraperitoneal (ip) or both intraperitoneal and intranasal (ip/in). The additional Ab treatment route has been demonstrated to increase the efficacy of protection against aerosol alphavirus exposure.

Figure 14A:
FIG. 14A shows exemplary data from IVIS imaging from control animals.
Figure 14B:
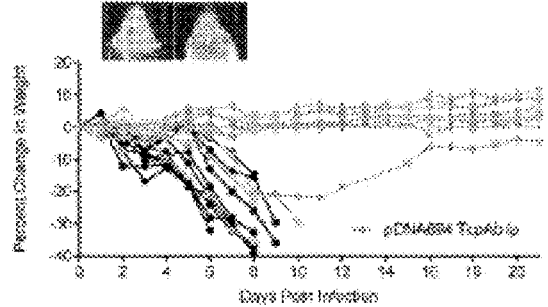
FIG. 14B shows exemplary data from IVIS imaging and clinical data from prophylactically treated animals.
Figure 14C:
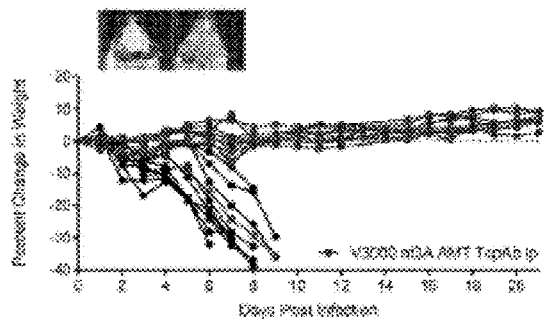
FIG. 14C shows exemplary data from IVIS imaging and clinical data from prophylactically treated animals.
Figure 14D:
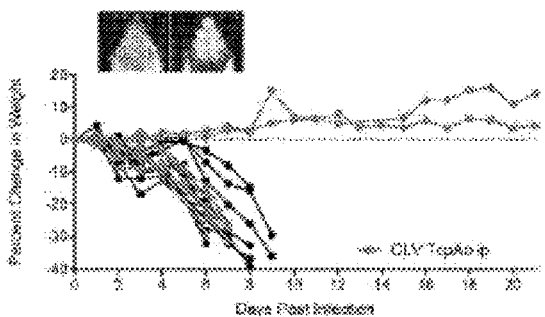
FIG. 14D shows exemplary data from IVIS imaging and clinical data from prophylactically treated animals.
Figure 14E:
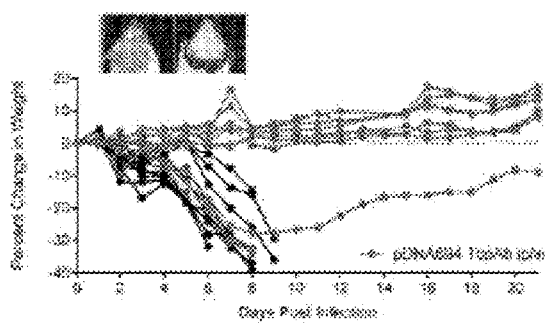
FIG. 14E shows exemplary data from IVIS imaging and clinical data from prophylactically treated animals.
Figure 14F:
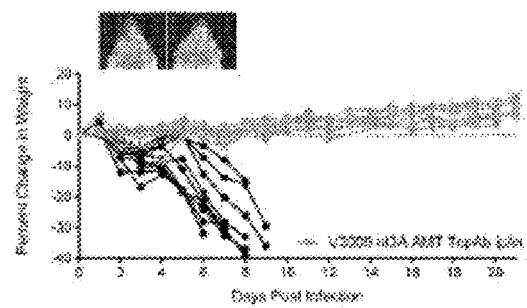
FIG. 14F shows exemplary data from IVIS imaging and clinical data from prophylactically treated animals.
Figure 14G:
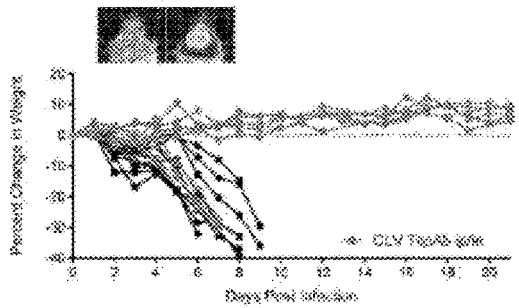
FIG. 14G shows exemplary data from IVIS imaging and clinical data from prophylactically treated animals.
Figure 14H:
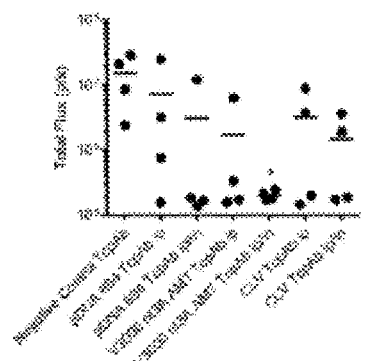
FIG. 14H shows quatification of data from the IVIS studies.
Figure 15A:
FIG. 15A shows exemplary data from IVIS imaging from control animals.
Figure 15B:
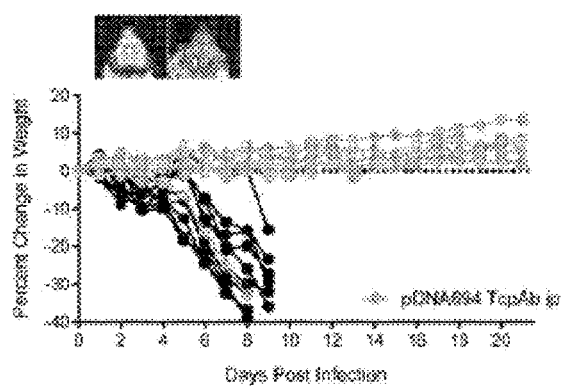
FIG. 15B shows exemplary data from IVIS imaging and clinical data from theraputically treated animals.
Figure 15C:
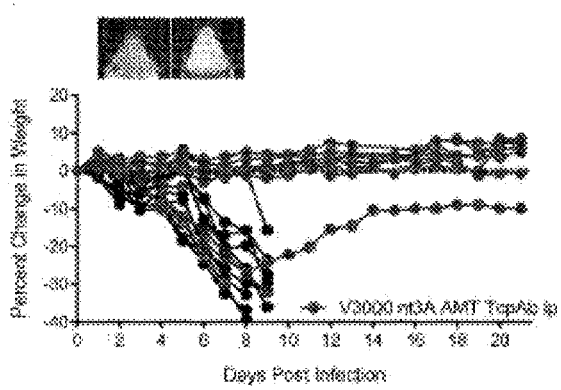
FIG. 15C shows exemplary data from IVIS imaging and clinical data from theraputically treated animals.
Figure 15D:
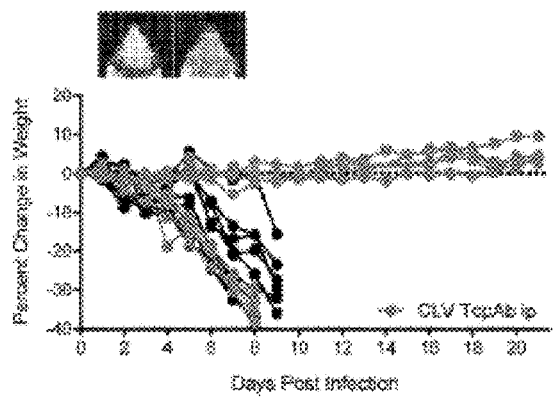
FIG. 15D shows exemplary data from IVIS imaging and clinical data from theraputically treated animals.
Figure 15E:
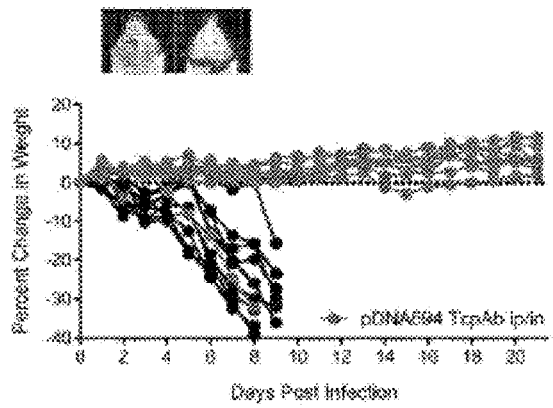
FIG. 15E shows exemplary data from IVIS imaging and clinical data from theraputically treated animals.
Figure 15F:
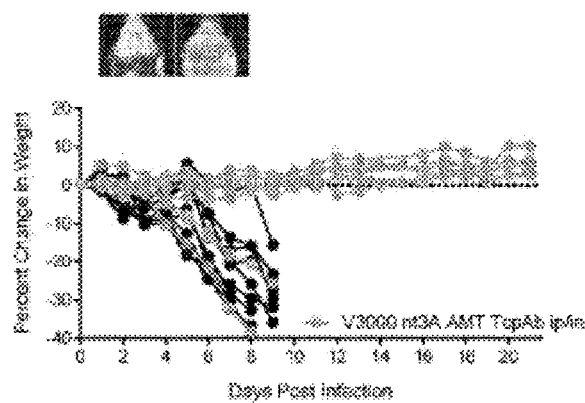
FIG. 15F shows exemplary data from IVIS imaging and clinical data from theraputically treated animals.
Figure 15G:
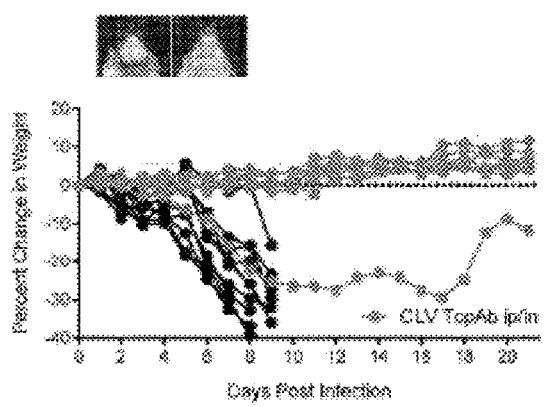
FIG. 15G shows exemplary data from IVIS imaging and clinical data from theraputically treated animals.
Figure 15H:
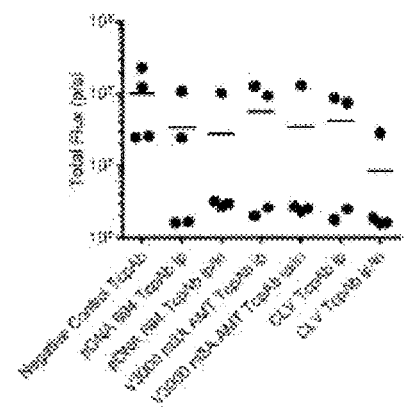
FIG. 15H shows quatification of data from the IVIS studies.

At a standard dose aerosol exposure (50-100 LD50), which causes uniform mortality in 6-9 days, CLV-derived TcpAbs (FIG. 14D) demonstrated less efficacy, especially in ip prophylactic treatment, compared to pDNA694-(FIG. 14B) or V3000 nt3A AMT-(FIG. 14C) derived TcpAbs, both of which produced significantly more survivors and extended average survival times (AST) (p<0.05; Table 6). Additionally, only mice treated prophylactically ip/in with V3000 nt3A AMT-derived TcpAb had significantly less IVIS signal in the head compared to mice treated with the negative control TcpAb while all of the other anti-VEEV TcpAb prophylactically treated mice had at least one mouse exhibiting levels of IVIS signal in the head similar to mice treated with the negative control TcpAb (FIG. 14H). Interestingly, the CLV-derived TcpAb was more effective when mice were treated therapeutically ip/in vs prophylactically ip/in (p=0.01; Table 6; FIG. 14G vs 15G). However, there was not a significant difference between mice who received the negative control TcpAb therapeutically and mice who received the anti-VEEV TcpAbs because at least one mouse had similar levels of IVIS signal in the head compared to the control mice (FIG. 15H). There was no significant difference in percentage mortality or survival time for the pDNA694 or V3000 nt3A AMT-derived TcpAbs (Table 6) between prophylactic treatment (FIG. 14) and therapeutic treatment (FIG. 15).

TABLE 6

Efficacy of human VEEV specific TcpAb to protect against standard dose aerosol challenge

| TcpAb | Route | Timing[1] | Percent survival | AST[2] |
|---|---|---|---|---|
| Negative Control | | prophylactic | 0% | 7.6 ± 1.1 d |
| | | therapeutic | 0% | 8.6 ± 0.5 d |
| CLV | ip | prophylactic | 20% | 6.9 ± 0.2 d |
| | ip/in | | 60% | 7.0 ± 0.0 d |
| | ip | therapeutic | 50% | 7.8 ± 0.4 d |
| | ip/in | | 100% | N/A[3] |
| pDNA694 | ip | prophylactic | 80%* | 9.3 ± 1.3 d# |
| | ip/in | | 80% | 8.0 ± 0.0 d |
| | ip | therapeutic | 90% | 8.5 ± 0.0 d |
| | ip/in | | 90% | 8.0 ± 0.0 d |
| V3000 nt3A AMT | ip | prophylactic | 90%* | 9.0 ± 0.0 d# |
| | ip/in | | 100% | N/A[3] |
| | ip | therapeutic | 80% | 7.8 ± 0.3 d |
| | ip/in | | 70% | 8.3 ± 0.8 d |

[1]Propylactic treatment 12 hrs before challenge; therapeutic treatment 12 hrs post challenge
[2]Average survival time (AST) in days (d)
[3]Not applicable (N/A)
*p < 0.05 Chi-square test CLV vs pDNA694 and V3000 nt3A AMT
p < 0.05 Mantel-Cox Log Rank test CLV vs pDNA694 and V3000 nt3A AMT To further explore efficacy differences between the different VEEV TcpAb preparations, mice were exposed to a high dose aerosol challenge (>100 LD50; Table 6). Increasing the aerosol dose dramatically decreased efficacy of all three preparations when the mice only received one dose of the TcpAb, however efficacy differences, as measured by survival, were apparent (Table 6). CLV TcpAb treatment no longer provided protection either prophylactically or therapeutically against VEEV aerosol challenge and yielded ASTs similar to mice treated with the negative control TcpAbs (Table 6). Although pDNA694 TcpAbs offered little protection (10-20%), mice had a significant increase in AST compared to CLV (Table 6) and negative control (Table 6) TcpAb-treated mice. Interestingly, the mice treated with the V3000 nt3A AMT TcpAbs exhibited significantly greater survival (40-50%) and extended AST compared to both CLV and pDNA694 TcpAb-treated mice. These data suggest that the repertoire of pAbs generated from Tc bovines hyperimmunized with V3000 nt3A AMT is more effective at protecting mice both prophylactically and therapeutically against a high dose aerosol challenge.

TABLE 6

Efficacy of human VEEV specific TcpAb to protect against high dose aerosol challenge

| TcpAb | Route | Timing | One Dose[1] % survival | AST[3] | Route | Timing | Two Doses[2] % survival | AST[3] |
|---|---|---|---|---|---|---|---|---|
| Negative Control | | prophylactic | 0% | 6.0 ± 0.0 d | | prophylactic | 0% | 6.3 ± 0.6 d |
| | | therapeutic | 0% | 6.5 ± 0.5 d | | therapeutic | 0% | 6.4 ± 0.8 d |
| CLV | ip | prophylactic | 0% | 6.5 ± 0.5 d | ip | prophylactic | 0% | 6.4 ± 0.5 d |
| | ip/in | | 0% | 6.5 ± 0.5 d | ip/in | | 0% | 6.3 ± 0.5 d |
| | ip | therapeutic | 0% | 6.4 ± 0.5 d | ip | therapeutic | 0% | 6.6 ± 0.5 d |
| | ip/in | | 0% | 6.5 ± 0.5 d | ip/in | | 0% | 6.8 ± 0.4 d |
| pDNA694 | ip | prophylactic | 0% | 7.7 ± 0.8 d[#] | ip | prophylactic | 10% | 7.8 ± 0.5 d[#] |
| | ip/in | | 20% | 7.8 ± 0.5 d[#] | ip/in | | 20% | 9.0 ± 1.6 d[#] |
| | ip | therapeutic | 10% | 7.9 ± 0.9 d[#] | ip | therapeutic | 30% | 8.4 ± 1.6 d[#] |
| | ip/in | | 0% | 7.5 ± 2.1 d[#] | ip/in | | 40%*** | 8.7 ± 2.1 d[#] |
| V3000 nt3A AMT | ip | prophylactic | 40%*,** | 8.4 ± 0.8 d[#,##] | ip | prophylactic | 66%*,** | 9.7 ± 1.2 d[#] |
| | ip/in | | 40%* | 10.0 ± 1.0 d[#,##] | ip/in | | 88%*,** | 10.5 ± 0.0 d[#,##] |
| | ip | therapeutic | 50%*,** | 8.3 ± 0.4 d[#,##] | ip | therapeutic | 88%*,** | 9.0 ± 0.0 d[#] |
| | ip/in | | 50%*,** | 9.5 ± 2.3 d[#,##] | ip/in | | 100%*,** | N/A[4,#] |

[1]Propylactic treatment 12 hrs before challenge; therapeutic treatment 12 hrs post challenge
[2]Propylactic treatment 12 hrs before challenge and again 48 hrs post challenge; therapeutic treatment 12 hrs post challenge and again 48 hrs post challenge
[3]Average survival time (AST) in days (d)
[4]Not applicable (N/A)
*$p < 0.05$ Chi-square test CLV vs V3000 nt3A AMT
**$p < 0.05$ Chi-square test pDNA694 vs V3000 nt3A AMT
***$p < 0.05$ Chi-square test CLV vs pDNA694
[#]$p < 0.05$ Mantel-Cox Log Rank test CLV vs V3000 nt3A AMT and pDNA694
[##]$p < 0.05$ Mantel-Cox Log Rank test CLV vs V3000 nt3A AMT and pDNA694 vs V3000 nt3A AMT Finally, it was determined if the dosing multiplicity affected efficacy of the anti-VEEV TcpAb preparations versus a high dose aerosol challenge, considering that multiple doses are likely to be given in the context of human therapeutic treatment. Mice were given two doses of TcpAbs (Table 6) using either prophylactic (FIGS. 16 and 17) or therapeutic treatment strategies (FIGS. 18 and 19). Administering two doses of CLV-derived TcpAbs either in the prophylactic group (FIGS. 16D and 16G) or in the therapeutic group (FIGS. 18D and G) did not increase survival or extend AST (Table 6) compared mice who received the negative control TcpAbs. Additionally, clinical signs were similar between mice who received the negative control TcpAb (FIGS. 17A and 19A) and mice who received the CLV TcpAb using either strategy (FIGS. 17D and G and FIGS. 19D and G). Similarly, in the prophylactic group, two doses of pDNA694-derived TcpAbs did not alter survival or extend AST compared to a single dose (Table 4). However, in the therapeutic ip/in group, two doses of pDNA694-derived TcpAbs significantly increased the number of survivors compared to a single dose (p=0.03). Furthermore, prophylactic doses of pDNA694-derived TcpAbs given ip produced a two-day delay in onset of clinical signs of disease compared to mice who received the negative control TcpAbs (FIGS. 17A and 17B). Mice that received two doses of V3000 nt3A AMT TcpAbs had twice the number of survivors compared to one dose, both prophylactically ip/in (40% to 88% survival; p=0.03) and therapeutically ip/in (50% to 100% survival; p=0.01). Unlike other groups, not all mice that received the V3000 nt3A AMT TcpAbs prophylactically exhibited clinical signs of disease (FIG. 17F). Additionally, when mice were treated prophylactically, only the V3000 nt3A AMT TcpAb groups exhibited significantly less IVIS signal in the head than the negative control TcpAb group (FIG. 16H).

Figure 16A:
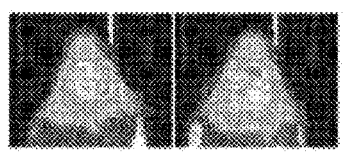
FIG. 16A shows exemplary data from IVIS imaging from control animals.
Figure 16B:
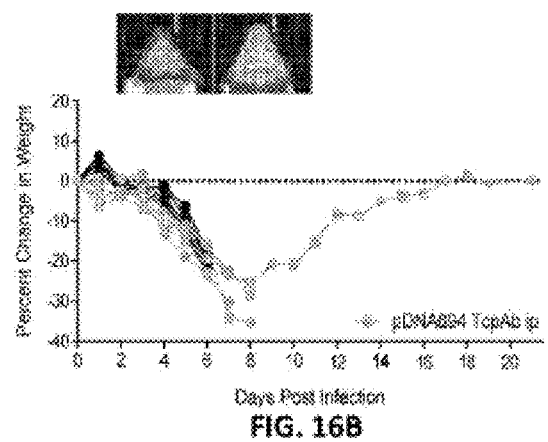
FIG. 16B shows exemplary data from IVIS imaging and clinical data from prophylactically treated animals.
Figure 16C:
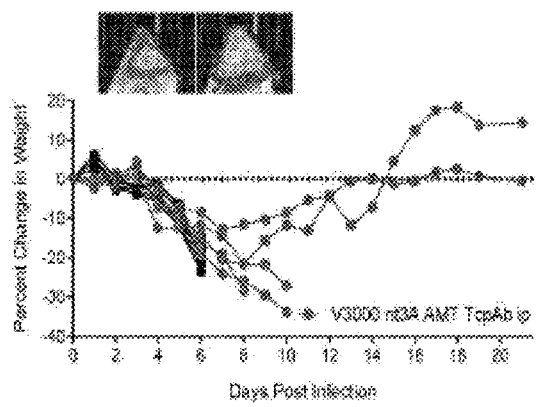
FIG. 16C shows exemplary data from IVIS imaging and clinical data from prophylactically treated animals.
Figure 16D:
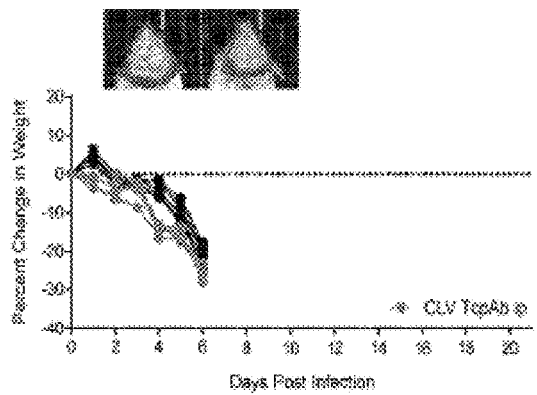
FIG. 16D shows exemplary data from IVIS imaging and clinical data from prophylactically treated animals.
Figure 16E:
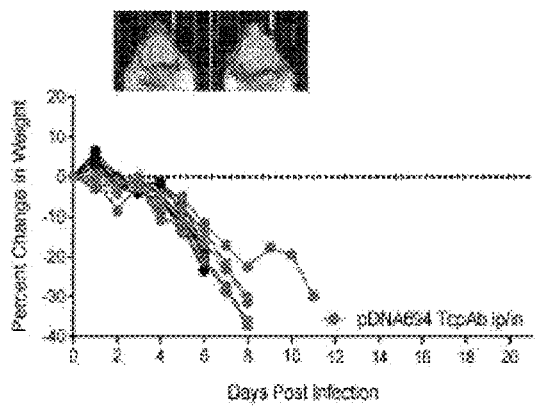
FIG. 16E shows exemplary data from IVIS imaging and clinical data from prophylactically treated animals.
Figure 16F:
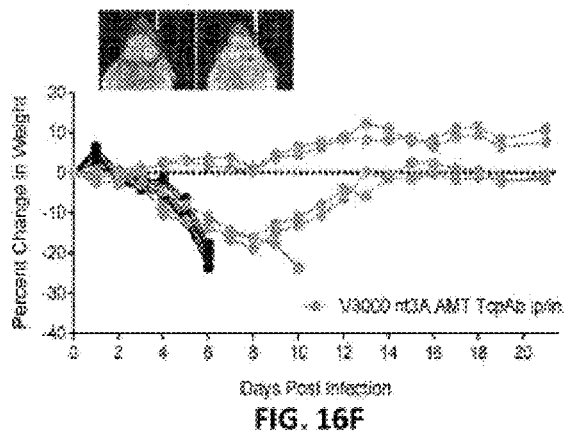
FIG. 16F shows exemplary data from IVIS imaging and clinical data from prophylactically treated animals.
Figure 16G:
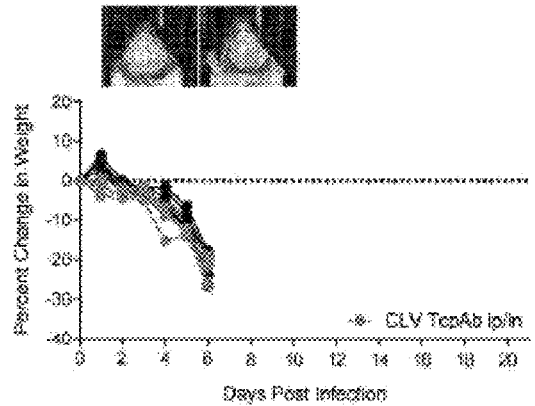
FIG. 16G shows exemplary data from IVIS imaging and clinical data from prophylactically treated animals.
Figure 17A:
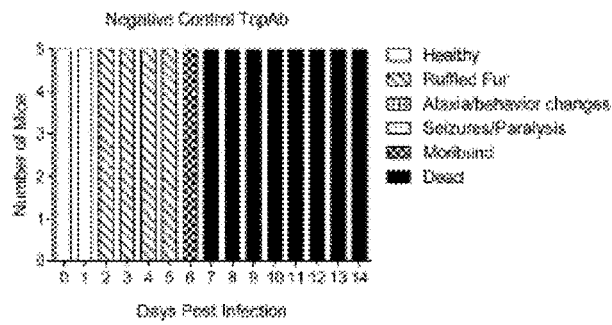
FIG. 17A shows clinical data for the negative control group.
Figure 17B:
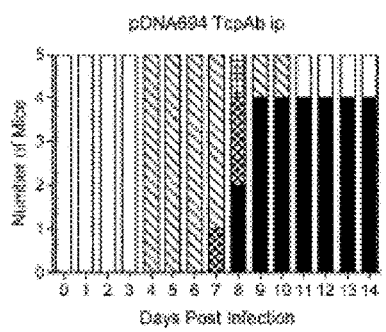
FIG. 17B shows clinical data from animals receiving pDNA694 TcpAb via IP administration.
Figure 17C:
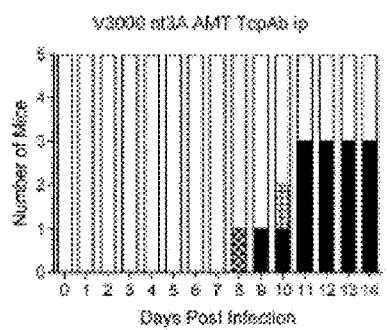
FIG. 17C shows clinical data from animals receiving V3000 nt3A AMT TcpAb via IP administration.
Figure 17D:
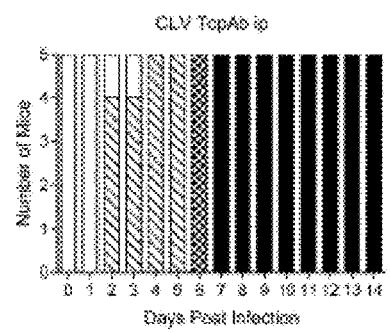
FIG. 17D shows clinical data from animals receiving CLV TcpAb via IP administration.
Figure 17E:
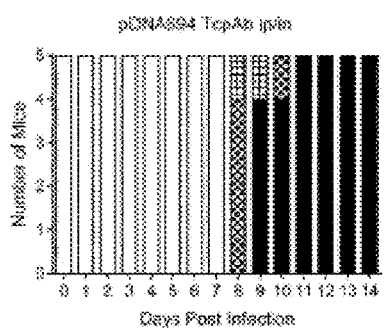
FIG. 17E shows clinical data from animals receiving pDNA694 TcpAb via IP/IN administration.
Figure 17F:
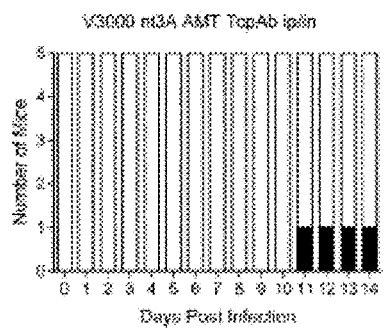
FIG. 17F shows clinical data from animals receiving V3000 nt3A AMT TcpAb via IP/IN administration.
Figure 17G:
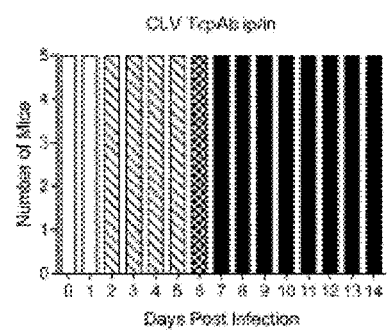
FIG. 17G shows clinical data from animals receiving CLV TcpAb via IP/IN administration.
Figure 18A:
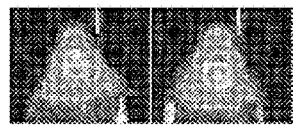
FIG. 18A shows exemplary data from IVIS imaging from the negative control group.
Figure 18B:
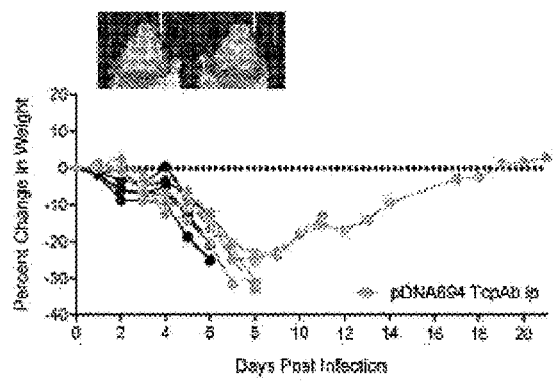
FIG. 18B shows exemplary data from IVIS imaging and clinical data from animals receiving pDNA694 TcpAb via IP administration.
Figure 18C:
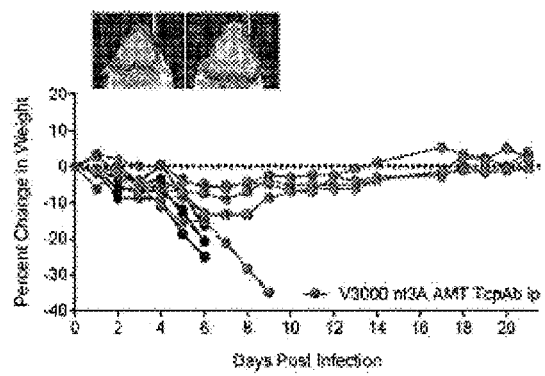
FIG. 18C shows exemplary data from IVIS imaging and clinical data from animals receiving V3000 nt3A AMT TcpAb via IP administration.
Figure 18D:
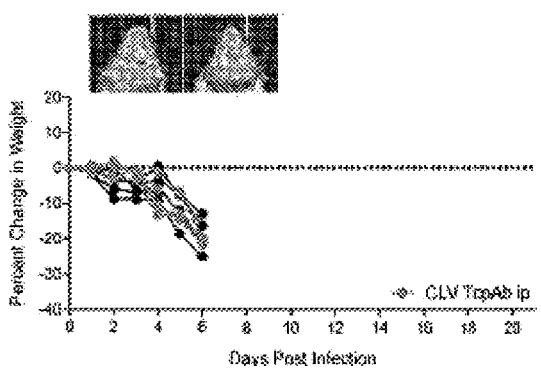
FIG. 18D shows exemplary data from IVIS imaging and clinical data from animals receiving CLV TcpAb via IP administration.
Figure 18E:
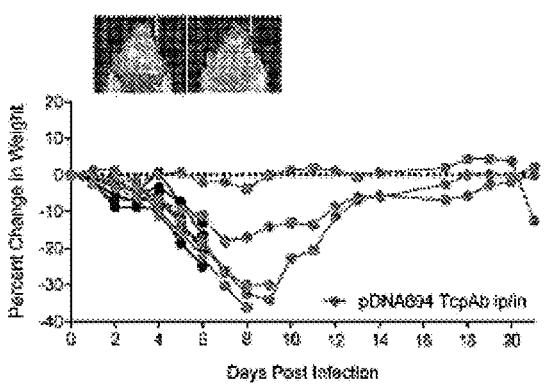
FIG. 18E shows exemplary data from IVIS imaging and clinical data from animals receiving pDNA694 TcpAb via IP/IN administration.
Figure 18F:
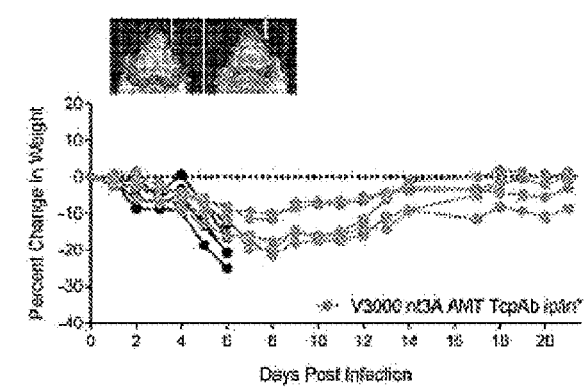
FIG. 18F shows exemplary data from IVIS imaging and clinical data from animals receiving V3000 nt3A AMT TcpAb via IP/IN administration.
Figure 18G:
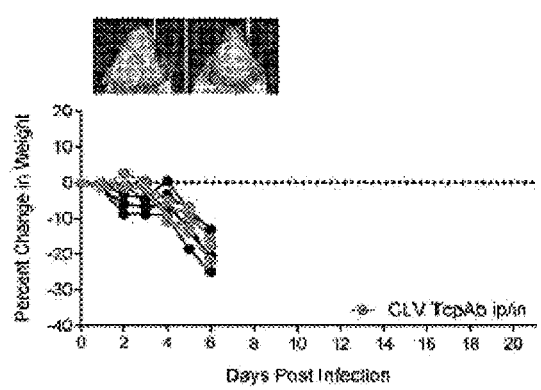
FIG. 18G shows exemplary data from IVIS imaging and clinical data from animals receiving CLV TcpAb via IP/IN administration.
Figure 19A:
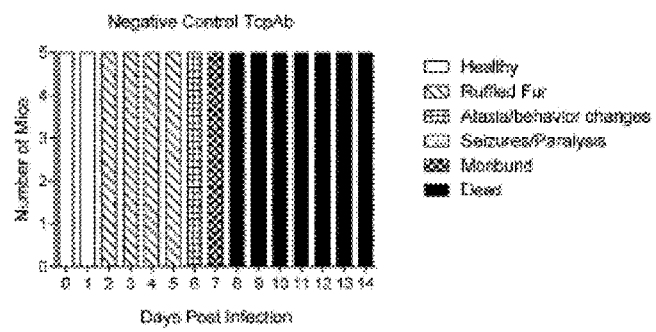
FIG. 19A shows clinical data from the negative control group.
Figure 19B:
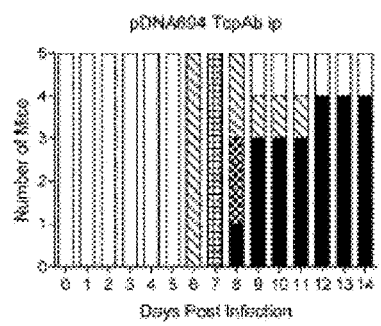
FIG. 19B shows clinical data from animals receiving pDNA694 TcpAb via IP administration.
Figure 19C:
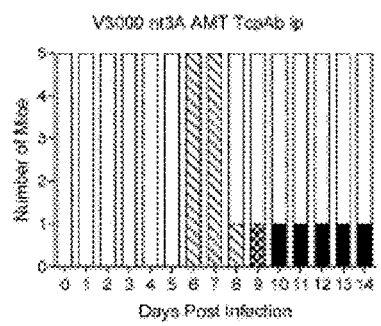
FIG. 19C shows clinical data from animals receiving V3000 nt3A AMT TcpAb via IP administration.
Figure 19D:
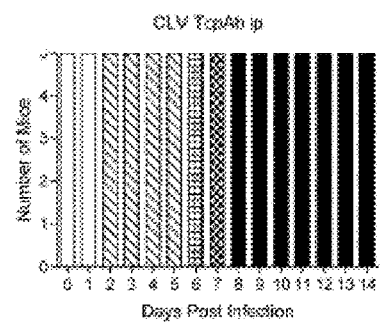
FIG. 19D shows clinical data from animals receiving CLV TcpAb via IP administration.
Figure 19E:
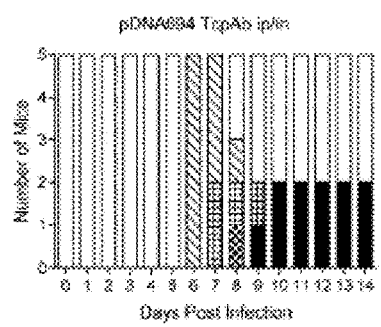
FIG. 19E shows clinical data from animals receiving pDNA694 TcpAb via IP/IN administration.
Figure 19F:
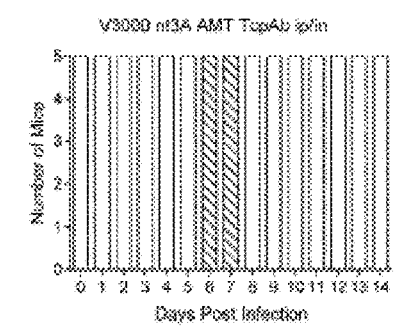
FIG. 19F shows clinical data from animals receiving V3000 nt3A AMT TcpAb via IP/IN administration.
Figure 19G:
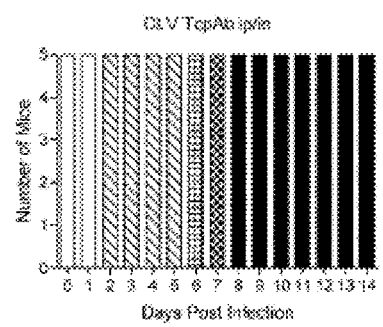
FIG. 19G shows clinical data from animals receiving CLV TcpAb via IP/IN administration.

When comparing the pDNA694 TcpAbs and V3000 nt3A AMT TcpAb groups only, the V3000 nt3A AMT TcpAb treatments produced significantly more survival (FIG. 16A, D, C, F and FIG. 18A, D, C, F). Furthermore, although all mice who received TcpAbs therapeutically exhibited clinical signs of disease (FIG. 19), mice who received V3000 nt3A AMT TcpAbs exhibited clinical signs for fewer days (FIGS. 19C and F) compared to surviving mice who received pDNA694 TcpAbs (FIGS. 19B and E). Overall, the hierarchy of efficacy of the different VEEV TcpAbs remained when mice receiving two doses of anti-VEEV TcpAbs, with CLV TcpAbs exhibiting the least efficacy and V3000 nt3A AMT TcpAbs exhibiting the greatest. The superior protective efficacy of V3000 nt3A AMT-derived TcpAb preparations is consistent with the higher IRNT80 and IgG/IgA levels measured in the in vitro assays.

Virus Replication and Weight Loss at 5 Days After Challenge.

Figure 20A:
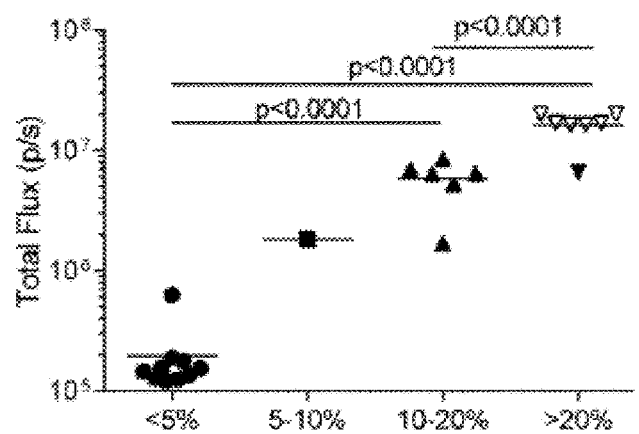
FIG. 20A shows data plotting IVIS signal versus weight loss groups for subcutaneous challenge of negative control TcAb and anti-VEEV TcAB treated mice.
Figure 20B:
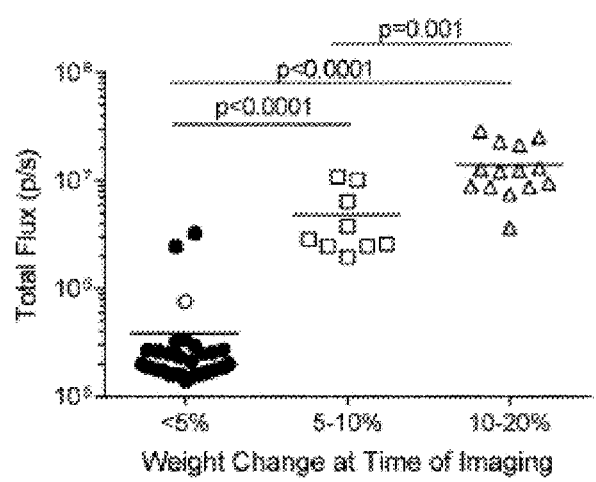
FIG. 20B shows data plotting IVIS signal versus weight loss groups for low dose aerosol challenge of negative control TcAb and anti-VEEV TcAB treated mice.

Assessment of the disease and virus replication characteristics of mice challenged by different routes may be informative regarding establishment of TcpAb treatment regimens. To study this, the quantitated IVIS imaging signals in comparison with weight loss and mortality data for all VEEV-infected mice (negative TcpAb control and anti-VEEV TcpAb treatment) were analyzed. In these studies, all mice given negative control TcpAb succumbed to infection and exhibited high levels of virus replication in the head as measured by IVIS signal. IVIS imaging confirmed that for all challenge types, mice exhibiting little/no weight loss also have little/no replication in the head compared to mice with weight loss (FIG. 20). Furthermore, the data suggest that the different challenge routes resulted in different disease profiles in the mice after TcpAb treatment. With sc challenge, surviving mice, all of which were treated with anti-VEEV TcpAb, could exhibit substantial virus replication in the head and weight loss (FIG. 20A). However, with both aerosol doses, manifestation of either of these disease characteristics was nearly always associated with mortality (FIGS. 20B and C). Furthermore, while significant differences replication measured by IVIS signal could be associated with increased weight loss (e.g., 5-10% versus 10-20% weight loss with standard dose aerosol; 5-10% versus >20% with high dose aerosol; FIGS. 20B and C), these were not associated with differences in mortality. This suggests that complete protection from disease and replication will be required for the aerosol challenge route. Therefore, additional, higher concentration doses of TcpAb may be required.

TcpAbs can Protect Against Simultaneous Infection with Two Pathogens

Figures 21, 22:
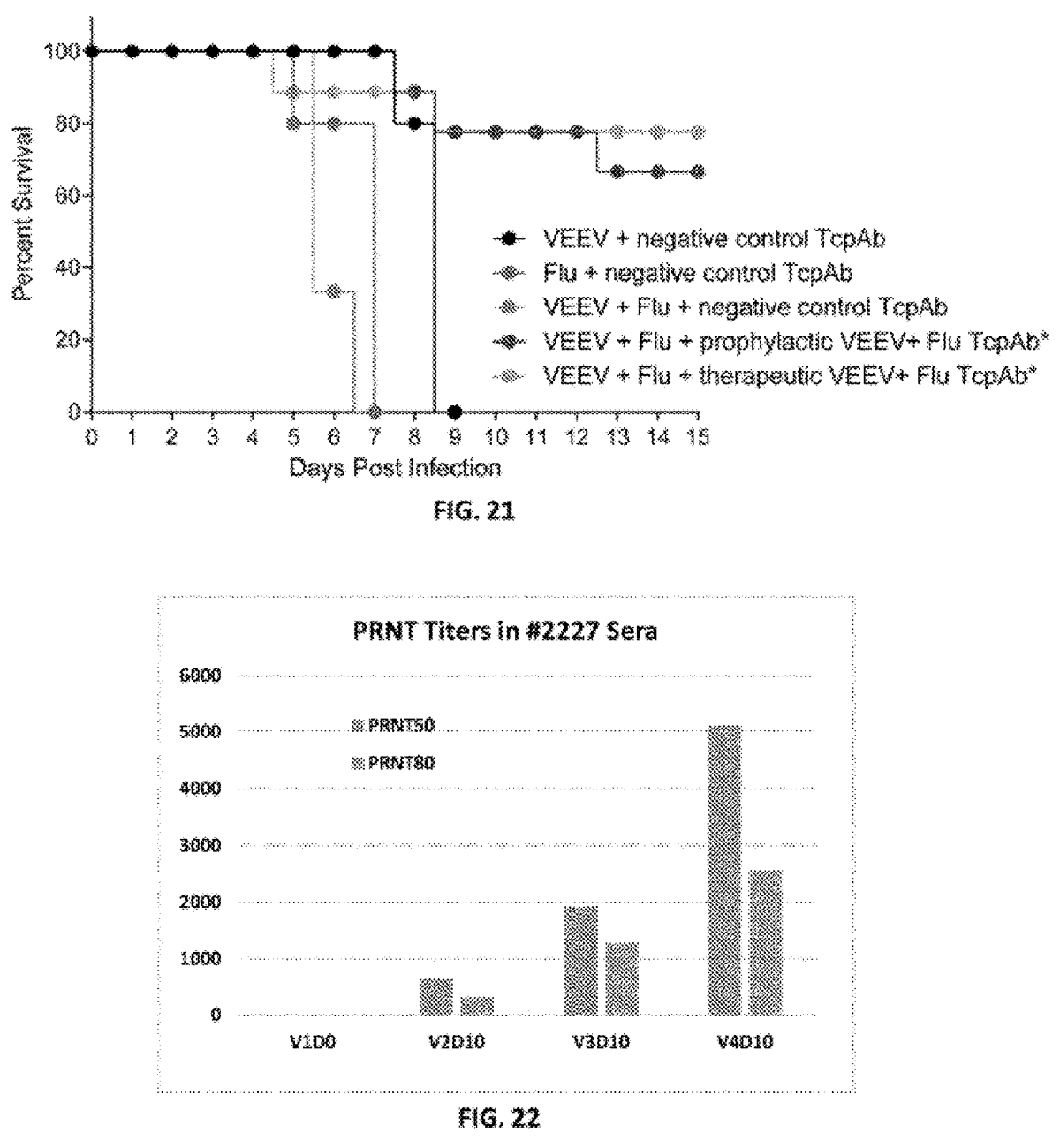

A significant advantage in protection from a bioweapons/bioterrorism attack would be the ability to treat infections with multiple pathogens, either before the time that an infecting organism is identified or in the case of a multi-organism release. Therefore, development of a multi-agent specific antiviral therapeutic is of high priority. To test the potential use of the TcpAb preparations in this context, DBA2 influenza-sensitive mice were treated either prophylactically or therapeutically with an equal mixture of VEEV TcpAbs (V3000 nt3A AMT TcpAbs) and influenza TcpAbs or given negative control TcpAbs then exposed to a lethal aerosol dose of VEEV and H1N1 influenza combination. As a baseline measure of disease manifestation, negative control-treated mice were also exposed to each virus individually. In control TcpAb-treated animals, the combination of the two viruses significantly ($p<0.001$) lowered the AST versus individual infections (FIG. 21) suggesting an increase in disease severity with co-infection. As an additional control, co-infected mice were treated with the individual TcpAbs (VEEV TcpAb or influenza TcpAb) and all succumbed to infection (DNS), further demonstrating that the co-infected mice received a lethal dose of both viruses. In contrast, co-infected mice treated either prophylactically (67% survival; $p=0.0013$) or therapeutically (78% survival; $p=0.0004$) with the two TcpAbs exhibited significantly higher survival compared to mice who were given the negative control TcpAbs (0%) (FIG. 21). These data suggest the TcpAb platform can be useful in the treatment of infections with multiple co-infecting pathogens.

Discussion

In this study, Tc bovines that produce genetically human pAbs were hyperimmunized with either a commercial trivalent alphavirus vaccine, pDNA expressing VEEV TrD WT structural proteins or inactivated cDNA clone-derived TrD virus. These approaches were used since live-attenuated viruses are not permitted to be used to immunize food livestock. Rigorous safety testing must occur to demonstrate complete inactivation of BSL-3 pathogens, therefore, the attenuated nt3A mutant of VEEV was utilized for inactivation and stringent interferon receptor-null mouse safety testing for validation of inactivation of the preparations. The three immunogens were then compared to determine 1) the antibody stimulation provided by each immunogen; 2) the protective efficacy of TcpAbs against sc and aerosol challenge with WT VEEV TrD; and 3) if the antigen used to hyperimmunize Tc bovines resulted in different efficacies of the resulting TcpAb preparations.

All three antigens used to hyperimmunze the Tc bovines produced VEEV-specific neutralizing Abs that were similarly protective in vivo from a subcutaneous challenge. However, differences in efficacy between the TcpAbs were observed during an aerosol challenge. Previous work with both mouse pAbs or mAbs demonstrated that protecting mice from aerosol challenge is more difficult than sc challenge. Furthermore, clade IA/B viruses like TrD are the most difficult to protect against from in an aerosol challenge. This example demonstrates that antigen-specific TcpAbs can protect against aerosol exposure. Additionally, when comparing efficacy between the two TcpAbs generated from inactivated virus, it is not unexpected that the VEEV-specific TcpAbs generated from V3000 nt3A AMT inactivation were more effective than those generated from the CLV antigen, for two reasons. First, CLV is created by formalin inactivation of TC83, the unlicensed vaccine strain of VEEV. Formalin has been shown to alter immunogenic epitopes by cross-linking adjacent proteins on the virion. Second, the majority of the neutralizing antibodies are raised against the E2/E1 glycoprotein. TC83 has mutations in the E2/E1 glycoprotein compared to TrD, potentially altering the efficacy of the antibodies versus the WT. However, it must also be noted that, due to timing and TcpAb processing constraints, only three bovine immunizations of the CLV were performed compared with four for the pDNA694 and V3000 nt3A AMT.

This example with VEEV-specific TcpAbs demonstrates that the type of antigen used to hyperimmunize Tc bovines influences the efficacy of the treatment in vivo against an aerosol challenge. Differences in efficacy following a high dose aerosol challenge between the pDNA694-derived TcpAbs and V3000 nt3A AMT-derived TcpAbs mirror the differences observed in vitro with higher neutralization and higher levels the VEEV-specific IgA and IgG ELISA in V3000-derived nt3A AMT TcpAbs. Similar results were observed when generating TcpAbs against MERS-CoV: killed whole virus generated TcpAbs with superior neutralization results in vitro compared with those from recombinant spike protein nanoparticles; however, the two MERS-CoV TcpAbs were not tested for differences in efficacy in vivo.

Further, this example has demonstrated efficacy of anti-VEEV TcpAbs to protect mice from mortality after either a sc or aerosol challenge with WT TrD. As described above, the V3000 nt3A AMT-derived TcpAbs were most protective in virtually all cases with a single low dose of Ab (5 mg/kg) delivered ip protecting mice challenged against lethality in both prophylactic and therapeutic treatments and completely preventing disease when given prophylactically. Prophylactic treatment with a single low dose given ip and in also protected from lethality and disease after a standard aerosol challenge and was partially protective from mortality with a therapeutic treatment. In a more realistic human treatment scenario, two doses given ip and in significantly reduced disease signs and protected most mice from lethality even after a high dose aerosol challenge. In other studies, pathogen-specific TcpAbs have required the use of 25 mg/kg TcpAbs or higher for protection. A MERS-CoV TcpAb was demonstrated to be reduce virus replication at 5 mg/kg; however, the mouse model used is not a lethal model of infection, and protection from lethal infection could not be ascertained. Furthermore, as seen with previous studies using mouse Abs, supplementing with intranasal administration of TcpAbs increased the efficacy VEEV TcpAbs against aerosol challenge. Considering the stringency of the high dose TrD aerosol challenge model in mice (100% mortality within 6 days) this suggests a significant potential for efficacy in humans who only rarely succumb to VEEV infection.

Co-infections commonly occur both during respiratory infections and also in individuals who are immunocompromised or as a result of co-infection of arthropod vectors with co-circulating arboviruses, such as the causative agents of the emerging diseases chikungunya and Zika fever. Additionally, it is conceivable that multiple pathogens could be combined in a malicious release of biowarfare agents. In this example, significant protection from mortality and reduced clinical signs was observed after prophylactic or therapeutic treatment combined with a lethal dual aerosol challenge of VEEV and influenza viruses. This suggests that that the Tc bovine pAb platform is an effective tool for treating co-infections in addition to individual pathogen exposures.

In summary, the feasibility of using anti-VEEV TcpAbs to prevent or treat disease was investigated. This platform provides the ability to generate pathogen-specific antibodies on a large scale in a short period of time, as would be needed after release of a bioterrorism agent or during an epidemic/pandemic outbreak. Furthermore, the demonstration that TcpAbs are able to protect both prophylactically and therapeutically against co-infection with VEEV and H1N1 influenza indicates that the system is highly flexible and adaptable to many possible viral threats. It is estimated that it would only require approximately 6 months or less from the first isolation of an emerging virus to production of commercial-quality human therapeutics with this system. Thus, the Tc bovines represent significant resource for combating natural and malicious infections with many viral pathogens.

Example 4

In this example, human antibodies to the Zika virus were produced via TC bovine. That is, the TC bovine were immunized with the Zika virus DNA vaccine.

The use of DNA vaccine technology and transchromosomal bovines (TcBs) to produce fully human polyclonal immunoglobulin (IgG) with potent antiviral neutralizing activity against the Zika virus is demonstrated. Specifically, a DNA vaccine was used to produce a candidate immunoglobulin product for the prevention and treatment of Zika virus infection. A needle-free jet injection device was used to vaccinate TcB, and high titer neutralizing antibodies (titers>100 were produced within six weeks. Plasma collected at day 10 after the third and fourth vaccination was used to produce anti-Zika human IgG. Subsequent challenge of hamsters with the Zika Puerto Rican strain and treatment with the candidate anti-Zika TcB produced human IgG protected ten out of eleven animals while most of the controls died from this partially lethal animal model. The findings that anti-Zika TcB human IgG is capable of protecting animal models of partially lethal Zika virus challenge when administered one day prior to challenge provides proof of concept that this approach can be used to develop candidate anti-Zika human polyclonal immunoglobulin based medical products without the need for human donors, humanization also known as despeciation, or inactivated/attenuated vaccine antigens.

Methods and Materials

First, DNA plasmids coding for the Zika virus were produced and purified. Next, as set forth in Table 4 below, the TC bovine (IGHM-/-IGHML1-/-IGL-/- and containing human artificial chromosome (HAC) vector labeled as isKcHACD) was vaccinated sub-dermally with 12 mg per dose of plasmids in at least two locations on the animal via needle-free PharmaJet™ injections without electroporation. For each vaccination, an adjuvant (formulated from ISA-206 (50% solution) with Quil A (0.5 mg/ml) as a 1 ml injection) was injected intra-muscularly adjacent to the site of the DNA vaccination using a syringe and needle. These vaccinations occurred every 21 days as set forth in Table 4 below to significantly boost the titer, affinity, and avidity of the polyclonal human antibodies produced.

TABLE 4

| TC Bovine | Vaccination | Vaccine Formulation |
|---|---|---|
| #2227 | V1 to V4 at 3 week intervals | Zika Vaccine: 2 × 6 mg plasmid (both sides of hind legs) + Adjuvant |

Plasma was collected on day 10 and/or day 14 of V2, V3, and V4. The antibodies were then purified from the plasma and can be used as an antibody reagent or therapeutic/prophylactic for passive transfer/passive vaccination against the specific targeted virus. Briefly, plasma was thawed at room temperature overnight, pH-adjusted to 4.8-0 with dropwise addition of 20% acetic acid (Fisher, catalog #A491), fractionaed by caprylic acid (Amresco, catalog #E499_) at a caprylic acid/total ratio of 1.0, and then clarified by centrifugation at 10,000 g for 20 min at room temperature. The supernatant containing IgG was then neutralized to pH 7.5 with 1 M tris, 0.22 mm-filtered, and affinity-purified with an anti-human IgG light chain-specific column, KappaSelect (GE Healthcare, catalog #17545804). Fully human IgG was further purified by passage over an anti-bovine IgG heavy-chain specific affinity column (Capto HC15 from GE Healthcare, catalog #17-5457-03). The purified anti-Zika human IgG has a concentration of 13.41 mg/ml in a sterile-filtered buffer consisting of 10 mM glutamic acid monosodium salt, 262 mM D-sorbitol, and Tween (0.05 mg/ml) (pH 5.5).

Plaque Reduction Neutralization Test (PRNT)

Serum samples collected from the vaccinated TcB were heat inactivated at 56° C. for 30 min and serum or purified samples were diluted to a working concentration of 2 mg/ml. Initial 1:5 dilutions of the samples were made followed by two-fold serial dilutions. Samples were diluted in complete Eagle's minimum essential medium with Earle's salts containing 2% heat inactivated FBS and 0.05% Gentamicin and analyzed in duplicate. An equal volume of cEMEM supplemented with 10% guinea pig complement (Cedarlane) containing 100 pfu of Zika virus was added to the sera dilutions and incubated at 37° C. for 1 hour. Following incubation, Vero or Vero E6 cell monolayers were inoculated, overlaid with agarose and incubated at 37° C. A second agarose overlay containing 5% neutral red was added 7 days later and plaques were counted the next day. Neutralization titers were determined to be the reciprocal of the last dilution of serum or purified material that reduced the number of plaques by 80% compared with the virus control wells.

Zika Virus Partially Lethal Disease Model Using Hamsters

Subsequently, hamsters were challenged with the Zika Puerto Rican strain, generally according to the methods described in the previous three examples. The antibody treatments were given at 100 mg/kg via IP to three different groups. SAB-155 (anti-Zika human polyclonal immunoglobulin derived from TcB) (V3) was administered to Group 1 (n=11), NC Ab was administered to Group 2 (n=12), and Group 3 was untreated and uninfected (used for body weight control).

Results

Neutralizing Activity of Plasma and Purified TcB Human IgG

Fully human IgG (referred hitherto as TcB human IgG) were purified from plasma collected from one immunized animal (TcB #2227). Serum samples as well as purified TcB human immunoglobulin was evaluated for Zika virus neutralizing activity in the Plaque Reduction Neutralization Test (PRNT). The results of the PRNT for both serum samples at vaccination timepoints V1-V4 are shown in FIG. 22 as well as for purified samples. The bovine developed neutralizing antibodies against the Zika virus as shown. Briefly, from V1 to V4, serum neutralizing titers increased from the baseline of eleven (value given for graphic purposes only) to as high as a PRNT50 (50% neutralization) of 1:5120 or a PRNT80 (80% neutralization) of 1:2560). Purified antibody at differing concentrations showed expected results.

Protection From Partially Lethal Zika Virus Challenge

Figure 24A:
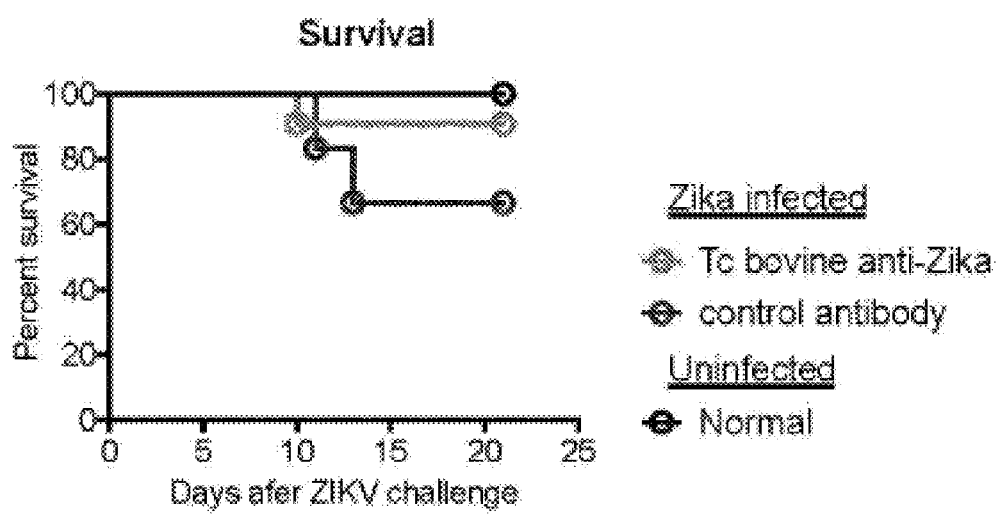
FIG. 24A shows Zika challenge survival data in treated and untreated groups.

To determine the protective efficacy of anti-Zika TcB human IgG in a model of partially lethal Zika challenge, hamsters were given 100 mg/ml (no dose finding or dose saving studies were intended and dose was chosen to provide the best possible results with finding minimum efficacious dose or maximum tolerable dose) of either negative control antibody or ant-Zika TcB human IgG. Ten of eleven hamsters treated with anti-Zika TcB human IgG survived. With respect to survival, as shown in FIG. 24A, one animal died in Group 1, but it did not display any signs of disease. In contrast, four animals died through day 9 of the study in Group 2 (negative control antibody), and all animals in Group 2 showed significant signs of disease.

Figure 24B:
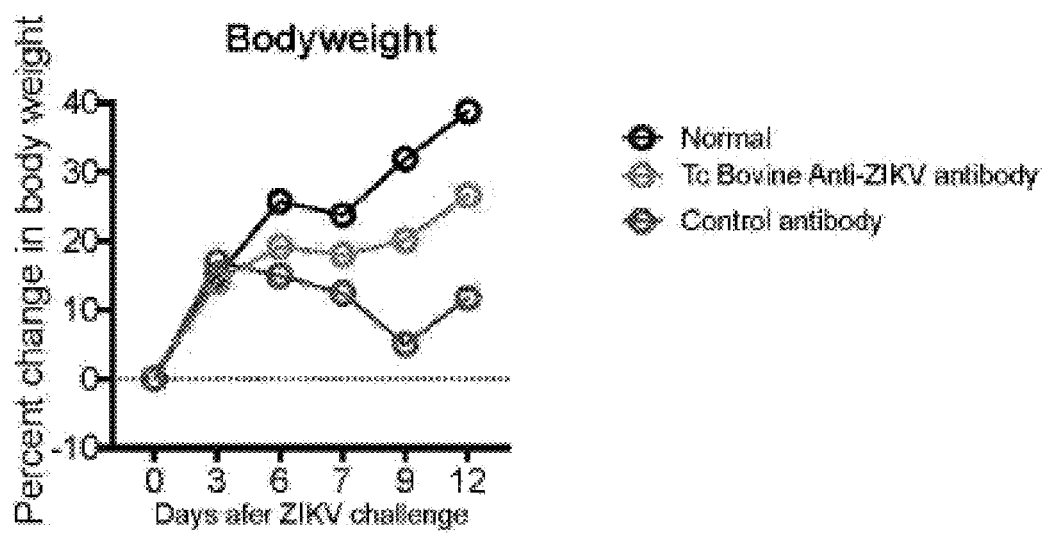
FIG. 24B shows group average body weight data in treated, untreated (control antibody), and uninfected groups.
Figure 24C:
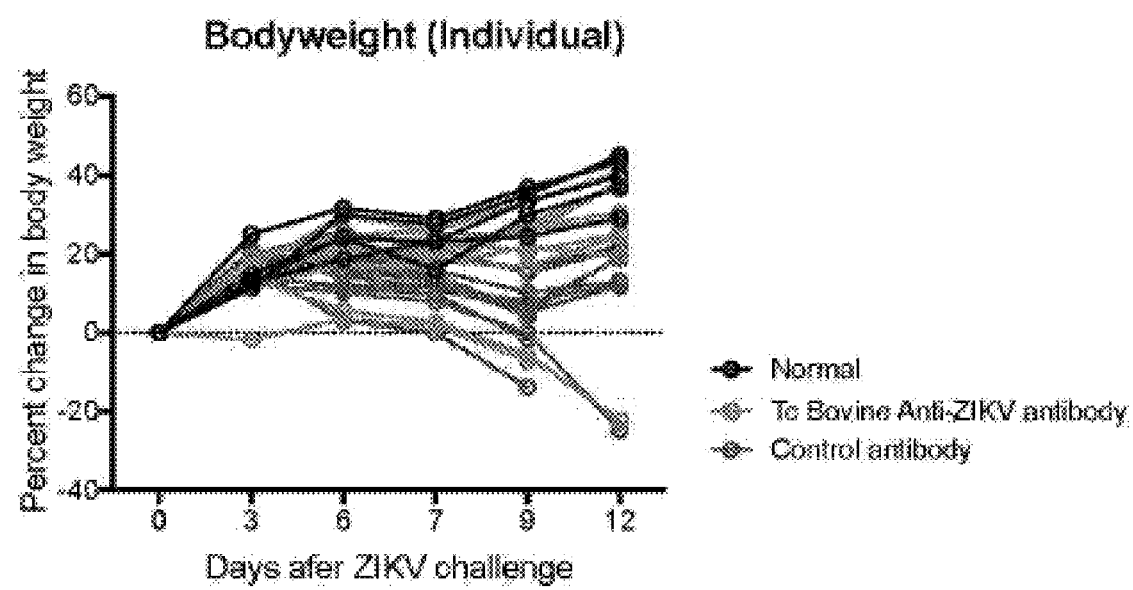
FIG. 24C shows individual animal body weight data following Zika challenge.

With respect to body weight as shown in FIGS. 24B and 24C, Group 1 averaged no reduction, while Group 2 exhibited loss of bodyweight from day 3 to day 9 post challenge.

With respect to displaying signs of disease, Group 1 displayed no signs, while Group 2 displayed signs of disease, such as conjunctivitis, ruffled fur, and lethargy.

Discussion

Here, it is demonstrated that it is possible to use DNA vaccination technology to the Zika virus in the TcB platform along with adjuvant injection adjacent to the DNA vaccination to produce polyclonal human IgG specially targeting Zika virus. It was possible to rapidly synthesize vaccine, vaccinate TcB, collect large volumes of plasma, and purify human polyclonal antibodies with potent neutralizing activity against the Zika virus. Using a DNA vaccine with simultaneous administration of intramuscular adjuvant resulted in consistent patterns of neutralizing antibody response against Zika virus as measured by PRNT. The flexibility of the DNA vaccine with adjuvant injection and the TcB platform allows for the rapid design and development of human polyclonal formulation against multiple viruses.

Figure Legends

FIGS. 1A-C shows data demonstrating the neutralizing antibody responses in TcBs vaccinated with hantavirus DNA vaccine plasmids. Two (TcB #1 and TcB #2) were vaccinated with an HPS vaccine consisting of an ANDV DNA vaccine and an SNV DNA vaccine component. (FIG. 1A) Schedule of vaccinations V1 to V4 (black arrows) and blood collection (red arrows). ANDV and SNV neutralizing antibody assays were performed on sera collected before vaccination (week 0) and on the indicated weeks after the first vaccination. (FIGS. 1B and C) PsVNA80 (FIG. 1B) and PRNT80 (FIG. 1C) titers for ANDV (red symbols) or SNV (blue symbols) for both animals. The cutoff for positive titers is 20. The a-ANDV titer of convalescent FFP from an HPS survivor is shown (red triangle).

Figure 2A:
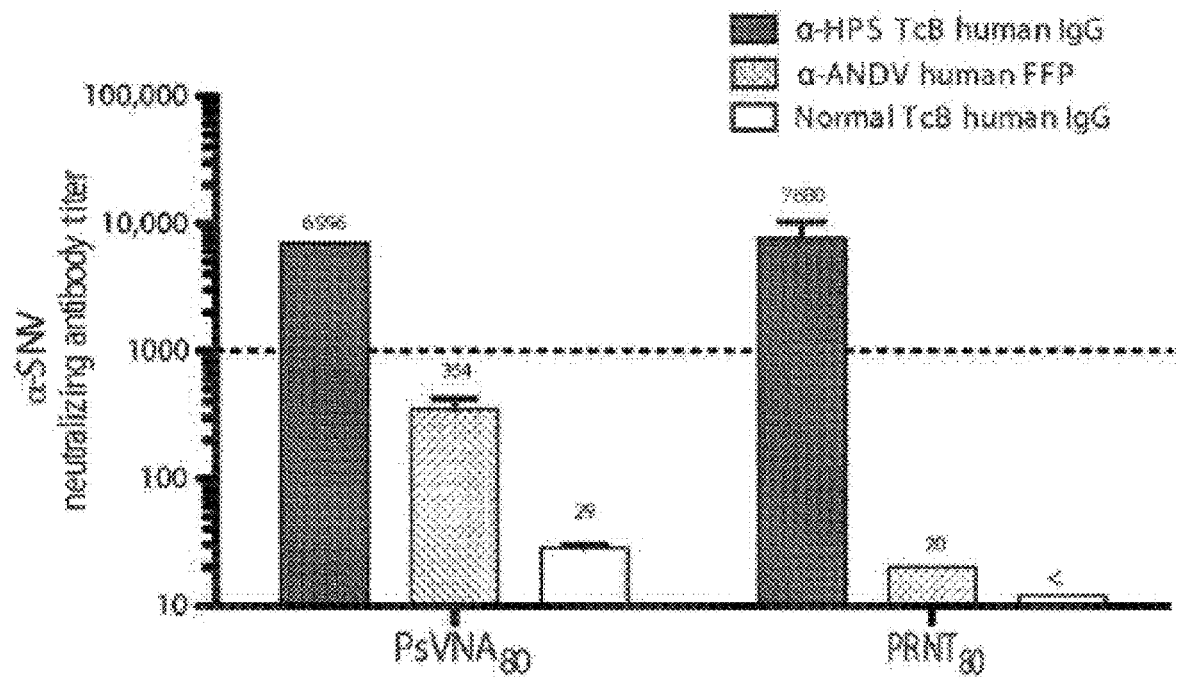
FIG. 2A shows data showing neutralizing activity in purified IgG from TcB.
Figure 2B:
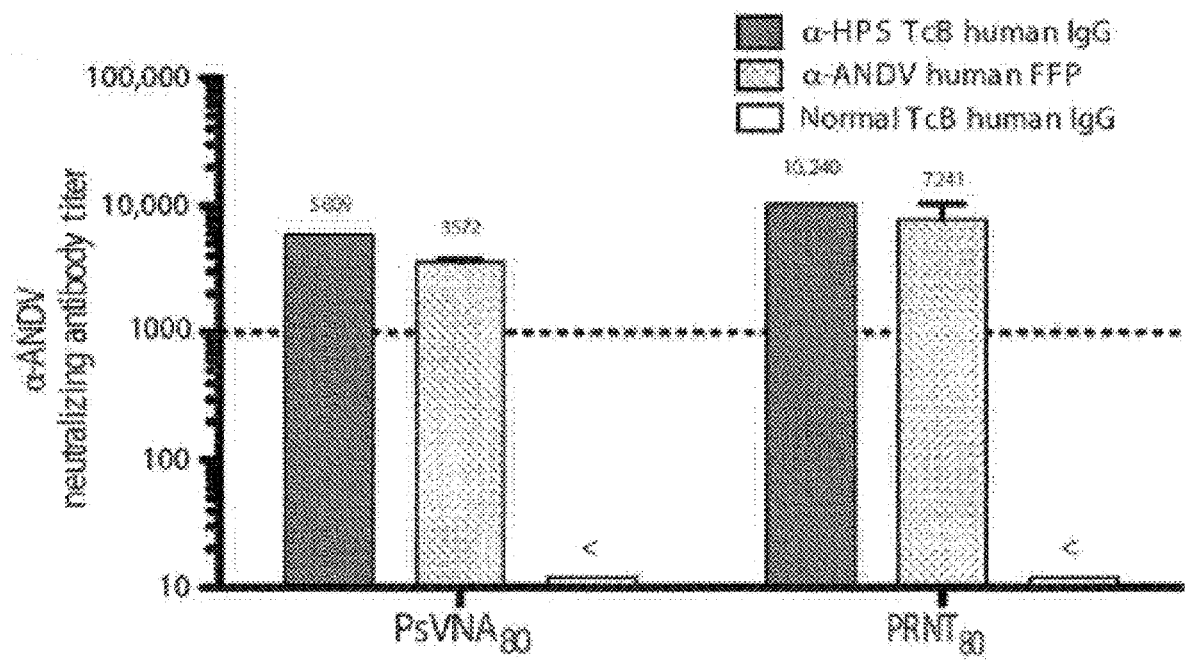
FIG. 2B shows data showing neutralizing activity in purified IgG from TcB.

FIGS. 2A-B show data showing neutralizing activity in purified IgG from TcB. IgG antibodies were purified from plasma collected from TcB #2. a-HPS TcB human IgG (8.42 mg/ml) (solid bar), positive control a-ANDV convalescent FFP (stippled bar), and negative control normal TcB IgG (9.04 mg/ml) (empty bar) were evaluated for neutralizing antibody activity by PsVNA and PRNT. (FIGS. 2A and B) a-SNV (FIG. 2A) and a-ANDV (FIG. 2B) PsVNA80 and PRNT80 titers. Samples with neutralizing antibody titers >1000 are considered to contain "high-titer" antibodies (dashed line). Samples with titers below 20 are denoted with a "<" symbol.

FIG. 3 shows data demonstrating the bioavailability of purified a-HPS TcB human IgG in Syrian hamsters. Three hamsters each were injected subcutaneously with either a high dosage [a-ANDV (64,000 NAU/kg)/a-SNV (77,000 NAU/kg), solid lines] or low dosage [a-ANDV (12,000 NAU/kg)/a-SNV (14,000 NAU/kg), dashed lines] of purified a-HPS TcB human IgG. The dosage was based on a-ANDV and a-SNV neutralizing activity. Sera collected from hamsters on the indicated days after injection were analyzed for a-ANDV and a-SNV neutralizing titer by PsVNA. Mean titers±SE are shown. The dashed line indicates limit of detection for the assay (PsVNA80 ≤20).

FIGS. 4 A-B shows data demonstrating the efficacy of a-HPS TcB human IgG to protect against lethal HPS caused by ANDV when administered after exposure. Four groups of eight hamsters were challenged intramuscularly with ANDV. (FIG. 4A) On days 5 and 8 after exposure, one group of hamsters was injected subcutaneously with a-HPS TcB human IgG [containing a-ANDV (20,000 NAU/kg)]. A second group was injected with the purified normal TcB human IgG. A third group of hamsters was injected with a-ANDV (12,000 NAU/kg) produced in rabbits (Rb) on day 5 as published previously (16). A fourth group of eight hamsters was not treated (No antibody). P values were determined using Kaplan-Meier survival analysis with logrank tests. (FIG. 4B) Sera collected from surviving hamsters on day 28 were tested by ELISA for evidence of ANDV infection. Symbols represent antibody titers of individual animals.

FIGS. 5A-B show data demonstrating the efficacy of a-HPS TcB human IgG to protect against lethal HPS caused by SNV when administered after exposure. Four groups of eight hamsters each were immunosuppressed with a combination of dexamethasone and cyclophosphamide described previously (15) and challenged intramuscularly with SNV. (FIG. 5A) On days 5 and 8, one group of hamsters was injected subcutaneously with a-HPS TcB human IgG [containing a-SNV (20,000 NAU/kg)]. A second group was injected with purified normal TcB human IgG. A third group was injected on day 5 only with a-SNV (20,000 NAU/kg) produced in rabbits (13). A fourth group remained untreated (No antibody). P values were determined using Kaplan-Meier survival analysis with logrank tests. (FIG. 5B) Lung tissue isolated on day 28 after infection was evaluated for viral genome by reverse transcription polymerase chain reaction (RT-PCR). Symbols represent viral genome detected in individual animals. P value was determined by Student's t test.

FIGS. 6A-C show data related to the production of human antibodies in TcBs. (FIG. 6A) Timeline of the vaccinations (black arrows), blood collections (red arrows) and plasma collections (blue arrows) for the TcBs. Serum samples obtained from two TcBs (#2295 and #2303) before vaccination (week 0) or 8-10 days after vaccinations 2-4 with EBOV-GPco and SUDV-GPco DNA vaccines were analyzed for total IgG antibodies by ELISA using (FIG. 6B) whole irradiated EBOV or SUDV antigens, and (FIG. 6C) EBOV rGP or SUDV rGP. Symbols represent the titers at each time point for each TcB.

FIGS. 7A-C show purified pAbs from vaccinated TcBs demonstrate neutralizing activity against EBOV and SUDV. Antibodies were purified from plasma collected from both TcBs eight days following the third and fourth vaccinations. (FIG. 7A) These purified V3 (22.16 mg/ml) and V4 (36.68 mg/ml) EBOV/SUDV human pAbs were evaluated by standard ELISA for total IgG antibody responses using whole-irradiated EBOV or SUDV antigen, and EBOV rGP or SUDV rGP antigen. (FIG. 7B) EBOV- and SUDV-neutralizing activity of the purified EBOV/SUDV human pAbs was determined by PsVNA, (FIG. 7C) and PRNT. Significant differences between titers are denoted by (*) where p<0.05.

FIGS. 8A-B show bioavailability of purified EBOV/SUDV human pAbs in mice. BALB/c mice (N=10) received a single IP injection of 100 mg/kg of the purified V3 EBOV/SUDV human pAbs. (FIG. 8A) Sera collected from individual mice at the indicated time points after injection were analyzed by standard ELISA for total human IgG using whole-irradiated EBOV or SUDV antigen, and EBOV rGP or SUDV rGP antigen. (FIG. 8B) Serum samples were also evaluated for EBOV- and SUDV-neutralizing activity by PsVNA.

FIGS. 9A-B show weight loss and survival of BALB/c mice challenged with maEBOV when administered purified EBOV/SUDV human pAbs before or after challenge. Groups of BALB/c mice (N=10) received a single IP injection of PBS, 100 mg/kg NS pAbs, or 100 mg/kg EBOV/SUDV pAbs one day before, or one or two days after challenge with 1000 pfu of maEBOV by IP injection. (FIG. 9A) Mean weight was determined daily for each dosing group and graphed as the percent mean of the starting weight. (FIG. 9B) Kaplan-Meier survival curves indicating the percentage of surviving mice at each day of the 21-day post-challenge observation period are shown. Survival of mice receiving the NS pAbs compared to the EBOV/SUDV pAbs one day before challenge (p=0.9573), NS pAbs vs EBOV/SUDV pAbs one day after challenge (p=0.0449), and NS pAbs vs EBOV/SUDV pAbs two days after challenge (p=0.5720). Significant differences between survival curves are denoted by (*) where p<0.05.

FIGS. 10A-B show weight loss and survival of BALB/c mice administered high, medium, or low doses of purified EBOV/SUDV human pAbs after maEBOV challenge. Groups of BALB/c mice (N=10) received a single IP injection of 100 mg/kg NS pAbs, 100 mg/kg EBOV/SUDV pAbs, 50 mg/kg EBOV/SUDV pAbs, or 10 mg/kg EBOV/SUDV pAbs one day after challenge or 50 mg/kg EBOV/SUDV pAbs, 25 mg/kg EBOV/SUDV pAbs, or 5 mg/kg EBOV/SUDV pAbs on day 1 and day 2 after challenge with 100 pfu maEBOV. (FIG. 10A) Mean weight was determined daily for each dosing group and graphed as the percent mean of the starting weight. All mice receiving the NS pabs succumb by day 8 post-challenge. (FIG. 10B) Kaplan-Meier survival curves indicating the percentage of surviving mice at each day of the 21-day post-challenge observation period are shown. The p-values for the following comparisons are as follows: 100 mg/kg NS pAbs vs. 100 mg/kg EBOV/SUDV pAbs +1 (p=0.0003), 100 mg/kg NS pAbs vs. 50 mg/kg EBOV/SUDV pAbs +1 (p=0.0059), NS pAbs vs. 10 mg/kg EBOV/SUDV pAbs +1 (p=0.0630), NS pAbs vs. 50 mg/kg EBOV/SUDV pAbs +1 and +2 (p=0.002), NS pAbs vs. 25 mg/kg EBOV/SUDV pAbs +1 and +2 (p=0.0046), NS pAbs vs. 5 mg/kg EBOV/SUDV pAbs +1 and +2 (p=0.1082), 100 mg/kg EBOV/SUDV pAbs +1 vs. 50 mg/kg EBOV/SUDV pAbs +1 and +2 (p=0.1988), 50 mg/kg EBOV/SUDV +1 vs. 25 mg/kg EBOV/SUDV pAbs +1 and +2 (p=0.9968), and 10 mg/kg EBOV/SUDV pAbs +1 vs. 5 mg/kg EBOV/SUDV pAbs +1 and +2 (p=0.7275). Significant differences between survival curves are denoted by (*) where p<0.05.

FIGS. 11A-B show data demonstrating weight loss and survival of IFNR −/− mice challenged with SUDV when administered purified EBOV/SUDV human pAbs after challenge. Groups of IFNR −/− mice (N=9) received a single IP injection of 100 mg/kg NS pAbs one day before, or 100 mg/kg EBOV/SUDV pAbs one day or two days after challenge via the IP route with 1000 pfu of SUDV. (FIG. 11A) Mean weight was determined daily for each dosing group and graphed as the percent mean of the starting weight. All mice in the NS pabs or the EBOV/SUDV pabs +2 groups succumb to disease by day 8 post-challenge. (FIG. 11B) Kaplan-Meier survival curves indicating the percentage of surviving mice at each day of the 19-day post-challenge observation period are shown. Survival of mice receiving the NS pAbs compared to the EBOV/SUDV pAbs one day after challenge (p=0.0009), and NS pAbs versus EBOV/SUDV pAbs two days after challenge (p=0.3981). Significant differences between survival curves are denoted by (*) where p<0.05.

FIGS. 12A-F show VEEV-specific antibody responses generated by hyperimmunization of transchromosomic (Tc) bovines. (FIGS. 12A-C) Neutralizing antibody in serum from Tc bovines hyperimmunized with (FIG. 12A) CLV, (FIG. 12B) pDNA694 or (FIG. 12C) V3000 nt3A AMT at various times post immunization. (FIGS. 12D-F) Serum from two Tc bovines hyperimmunized with CLV (V3D9), pDNA694 (V4D10) or V3000 nt3A AMT (V4D10) were pooled and purified for human antibodies as described in Materials and Methods. Purified antibodies were then tested for (FIG. 12D) neutralizing antibody (FIG. 12E) VEEV-specific human IgA or (FIG. 12F) VEEV-specific human IgG.

FIGS. 13A-I show efficacy of anti-VEEV TcpAb treatment against subcutaneous challenge. Six week-old Balb/c mice were either untreated or treated once intraperitoneally with 100 ug of anti-VEEV TcpAb prophylactically, 12 hrs before (FIGS. 13B-D) or therapeutically, 12 hrs after (FIGS. 13E-G), subcutaneous challenge in the rear footpad with 1000 PFU of V3000 nluc TAV. Three mice from control, prophylactic or therapeutic groups were imaged with IVIS at 5 days post challenge and photon flux quantitated for the head (FIGS. 13 H, I, respectively). One mouse representing the least clinical infection signs and one mouse representing the greatest clinical infection signs are shown in IVIS images from control (FIG. 13A), prophylactic (FIGS. 13B-D) or therapeutic (FIGS. 13E-G) groups. All IVIS images are set to the same scale. Daily weights are shown for mice who received the negative control TcpAb (black lines, FIGS. 13B-G), prophylactic (colored lines, FIGS. 13B-D) or therapeutic (colored lines, E-G) treatments. (FIGS. 13H-I) Statistical significance for IVIS imaging as determined by student's ttest. *p<0.05 pDNA694 TcpAb vs V3000 nt3A AMT TcpAb, *p<0.001 negative control vs VEEV TcpAb., ***p<0.0001 negative control vs VEEV TcpAb.

FIGS. 14A-H show efficacy of prophylactic anti-VEEV TcpAb treatment against standard dose aerosol challenge. Six week-old Balb/c mice were treated once intraperitoneally (ip) or intraperitoneally/intranasally (ip/in) with 100 m of either control TcpAb or the indicated anti-VEEV TcpAb 12 hrs before aerosol challenge with a standard dose aerosol (50-100 $LD_{50}$) of V3000 nluc TAV. (FIG. 14H) Three mice from control or prophylactic groups were imaged with IVIS at 5 days post challenge and photon flux quantitated for the head. One mouse representing the least clinical infection signs and one mouse representing the greatest clinical infection signs are shown in IVIS images from control (FIG. 14A) or prophylactic (FIGS. 14B-G) groups. All IVIS images are set to the same scale. Daily weights are shown for mice who received the negative control TcpAb (black lines, FIGS. 14B-G) or prophylactic (colored lines, FIGS. 14 B-G) treatments. (FIG. 14H) Statistical significance for IVIS imaging as determined by student's ttest. *p<0.05 compared to negative control TcpAb.

FIGS. 15A-H shows the efficacy of therapeutic anti-VEEV TcpAb treatment against standard dose aerosol challenge. Six week-old Balb/c mice were treated once intraperitoneally (ip) or intraperitoneally/intranasally (ip/in) with 100 μg of either control TcpAb or the indicated anti-VEEV TcpAb 12 hrs after aerosol challenge with a standard dose aerosol (50-100 $LD_{50}$) of V3000 nluc TAV. (FIG. 15H) Three mice from control or therapeutic groups were imaged with IVIS at 5 days post challenge and photon flux quantitated for the head. One mouse representing the least clinical infection signs and one mouse representing the greatest clinical infection signs are shown in IVIS images from control (FIG. 15A) or therapeutic (FIGS. 15B-G) groups. All IVIS images are set to the same scale. Daily weights are shown for mice who received the negative control TcpAb (black lines, FIGS. 15B-G) or therapeutic (colored lines, FIGS. 15B-G) treatments. (FIG. 15H) None of the treatments were significantly different from control in a Student's ttest (p>0.05).

FIGS. 16A-G show the efficacy of prophylactic anti-VEEV TcpAb treatment against high dose aerosol challenge. Six week-old Balb/c mice were treated with 100 m of either control TcpAb or the indicated anti-VEEV TcpAb followed by a high dose aerosol (>100 $LD_{50}$) challenge with V3000 nluc TAV. Two doses of TcpAb were administered either intraperitoneally (ip) (FIGS. 16B-D) or intraperitoneally and intranasally (ip/in) (FIGS. 16E-G) with the first dose 12 hrs before challenge and the second dose 48 hrs after challenge. One mouse exhibiting the least clinical infection signs and one mouse exhibiting the greatest clinical infection signs are shown in IVIS images from control (FIG. 16A) or prophylactic (FIGS. 16B-G) groups. All IVIS images are set to the same scale. Daily weights are shown for mice who received the negative control TcpAb (black lines, FIGS. 16B-G) or prophylactic (colored lines, FIGS. 16B-G) treatments.

FIG. 17 shows the efficacy of prophylactic anti-VEEV TcpAb treatment against clinical signs of disease after high dose aerosol challenge. Six week-old Balb/c mice were treated with 100 m of either control TcpAb or the indicated anti-VEEV TcpAb followed by a high dose aerosol (>100 $LD_{50}$) challenge with V3000 nluc TAV. Two doses of TcpAb were administered either intraperitoneally (B-D) or intraperitoneally and intranasally (E-G) with the first dose 12 hrs before challenge and the second dose 48 hrs after challenge. Mice were monitored daily for clinical signs of disease.

FIGS. 18A-G show the efficacy of therapeutic anti-VEEV TcpAb treatment against high dose aerosol challenge. Six week-old Balb/c mice were treated with 100 m of either control TcpAb or the indicated anti-VEEV TcpAb followed by a high dose aerosol (>100 $LD_{50}$) challenge with V3000 nluc TAV. Two doses of TcpAb were administered either intraperitoneally (ip) (FIGS. 18B-D) or intraperitoneally and intranasally (ip/in) (FIGS. 18E-G) with the first dose 12 hrs after challenge and the second dose 48 hrs after challenge. One mouse representing the least clinical infection signs and one mouse representing the greatest clinical infection signs are shown in IVIS images from control (FIG. 18A) or therapeutic (FIGS. 18B-G) groups. All IVIS images are se to the same scale. Daily weights are shown for mice who received the negative control TcpAb (black lines, FIGS. 18B-G) or therapeutic (colored lines, FIGS. 18B-G) treatments.

FIGS. 19A-G show the efficacy of therapeutic anti-VEEV TcpAb treatment against clinical signs of disease after high dose aerosol challenge. Six week-old Balb/c mice were treated with 100 m of either control TcpAb or the indicated anti-VEEV TcpAb followed by a high dose aerosol (>100 $LD_{50}$) challenge with V3000 nluc TAV. Two doses of TcpAb were administered either intraperitoneally (ip) (FIGS. 19B-D) or intraperitoneally and intranasally (ip/in) (FIGS. 19E-G) with the first dose 12 hrs after challenge and the second dose 48 hrs after challenge. Mice were monitored daily for clinical signs of disease.

Figure 20C:
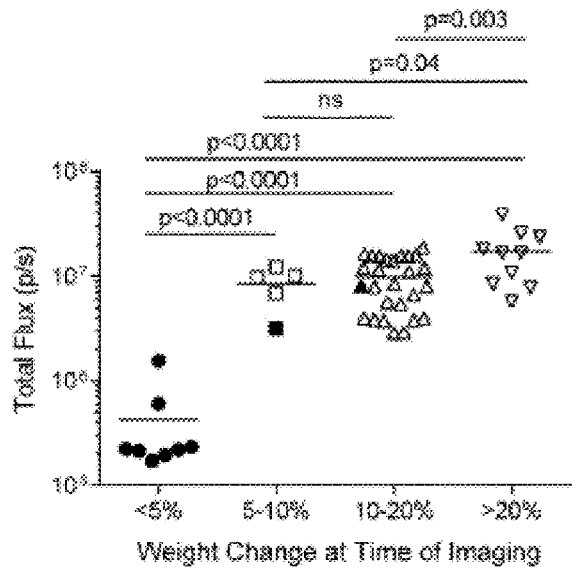
FIG. 20C shows data plotting IVIS signal versus weight loss groups for high dose aerosol challenge of negative control TcAb and anti-VEEV TcAB treated mice.

FIGS. 20A-C show the relationship of quantitated IVIS signal with weight loss for infected mice. Data plotting IVIS signal versus weight loss groups for subcutaneous (FIG. 20A), low dose aerosol (FIG. 20B) of high dose aerosol (FIG. 20C) challenge of negative control TcAb and anti-VEEV TcAB treated mice. Closed figures are mice that survived and open symbols are mice that succumbed to the challenge. All negative control Tc-Ab treated mice succumbed to infection.

FIG. 21 Shows the efficacy of combined TcpAb treatment against aerosol co-infection with influenza and VEEV. Six week old DBA2 mice were treated with negative control TcpAb or treated either prophylactically or therapeutically with anti-VEEV TcpAb (V3000 nt3A AMT) or anti-Influenza TcpAb (H1N1-H3N2) before lethal aerosol challenge with VEEV and Influenza (H1N1). Mice treated prophyclactically received two intraperitoneal doses of 100 μm anti-VEEV and 200 μm anti-flu TcpAb with the first dose 12 hrs before challenge and the second dose 48 hrs post-challenge. Mice treated therapeutically received two intraperitoneal doses of 100 μm anti-VEEV and 200 μm anti-flu TcpAb with the first dose 12 hrs after challenge and the second dose 48 hrs after challenge. Statistical significance was determined by Mantel Cox Log-Rank test. *p<0.001 versus negative control TcpAb. In negative control groups, survival time for each virus singly was significantly longer than the combined infection (p<0.01).

FIG. 22 shows data demonstrating Zika virus neutralization activity in a Plaque Reduction Neutralization Test (PRNT).

Figure 23:
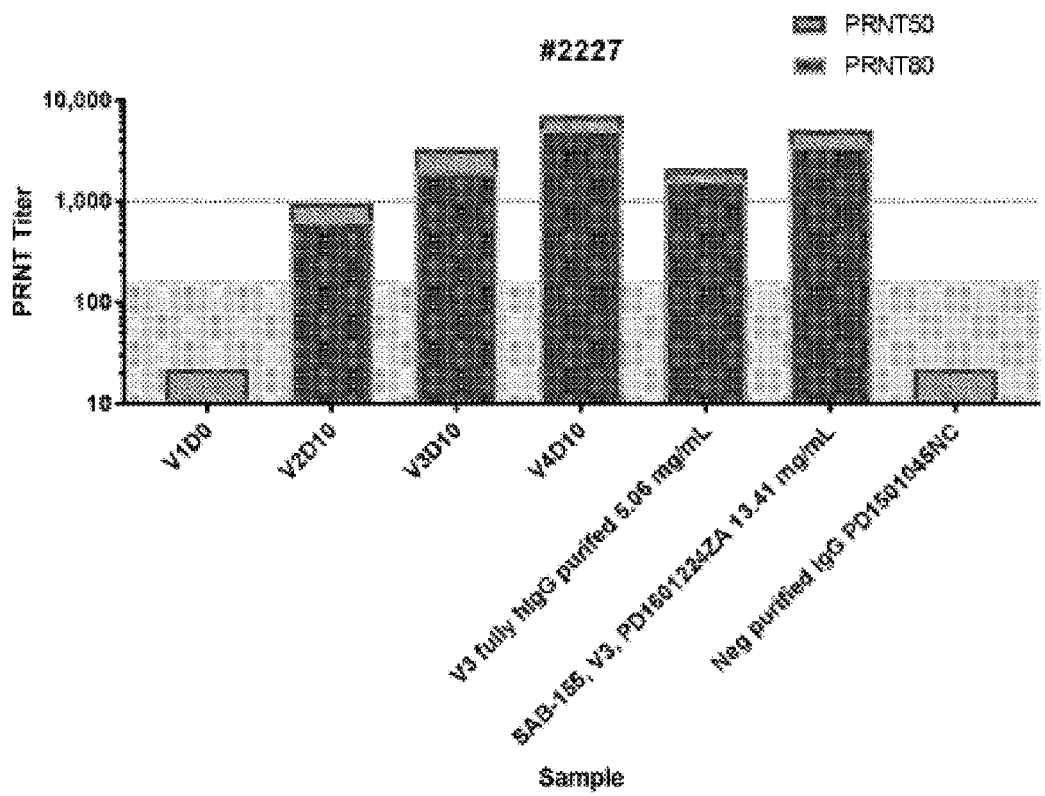
FIG. 23 shows data demonstrating protective efficacy of anti-Zika TcB human IgG in partially lethal Zika challenge.

FIG. 23 shows data demonstrating protective efficacy of anti-Zika TcB human IgG in partially lethal Zika challenge.

FIG. 24A shows Zika challenge survival data in treated and untreated groups.

FIG. 24B shows group average body weight data in treated, untreated (control antibody), and uninfected groups.

FIG. 24C shows individual animal body weight data following Zika challenge.

Although the disclosure has been described with reference to preferred embodiments, persons skilled in the art will recognize that changes may be made in form and detail without departing from the spirit and scope of the disclosed apparatus, systems and methods.

What is claimed is:

1. A method for producing human antibodies against a viral pathogen-derived DNA vaccine, comprising:
   a) injecting at least two DNA vaccines in at least two separate locations of a transchromosomal ungulate, the at least two DNA vaccines comprising:
      (i) a first DNA vaccine encoding a first antigen from a first strain of a viral pathogen, and
      (ii) a second DNA vaccine encoding a second antigen from a second strain of the same viral pathogen,
      wherein the first antigen is injected at a first location and the second antigen is injected at a second location, wherein each of the first and second locations is on a separate quarter of the transchromosomal ungulate;
      wherein the transchromosomal ungulate produces fully human IgG antibodies, wherein the transchromosomal ungulate is a knock-out for endogenous ungulate immunoglobulin genes, and comprises a human artificial chromosome (HAC) containing the full germ line sequence of human immunoglobulins;
   b) injecting an adjuvant to the transchromosomal ungulate in a location different from the first DNA vaccine location and the second DNA vaccine location;
   c) collecting plasma from the transchromosomal ungulate; and
   d) purifying polyclonal human IgG antibodies from the plasma.

2. The method of claim 1, wherein the viral pathogen is selected from a group consisting of: Hantavirus, Ebola virus, Venezuelan Equine Encephalitis, and Zika virus.

3. The method of claim 1, wherein the viral pathogen is Hantavirus, wherein the first strain of Hantavirus is Sin Nombre Hantavirus and the second strain of Hantavirus is Andes Hantavirus.

4. The method of claim 1, wherein the viral pathogen is Ebola virus, wherein the first strain of Ebola virus is Zaire Ebola virus and the second strain of Ebola virus is Sudan Ebola virus.

5. The method of claim 1, wherein each of the first and second DNA vaccines is injected subcutaneously or subdermally.

6. The method of claim 1, wherein each of the first and second DNA vaccines is injected at a dose of about 2 mg to about 40 mg per injection.

7. The method of claim 6, wherein each of the first and second DNA vaccines is injected at a dose of about 3 to 12 mg per injection.

8. The method of claim 1, further comprising repeating steps (a) and (b) at an interval of about 21 to about 28 days.

9. The method of claim 1, wherein plasma is collected from the transchromosomal ungulate between about 6 days to about 16 days after steps (a) and (b).

10. The method of claim 1, wherein the HAC comprises genes encoding:
    a) one or more human antibody heavy chains, wherein each gene encoding an antibody heavy chain is operatively linked to a class switch regulatory element;
    b) one or more human antibody light chains; and
    c) one or more human antibody surrogate light chains, and/or an ungulate derived IgM heavy chain constant region; wherein at least one class switch regulatory element of the genes encoding the one or more human antibody heavy chains is replaced with an ungulate-derived class switch regulatory element.

11. The method of claim 1, wherein the adjuvant is injected within 1 to 2 centimeters of the first and second locations.

12. The method of claim 1, wherein the adjuvant is injected intramuscularly.

13. The method of claim 1, wherein the knock-out for endogenous ungulate immunoglobulin genes comprises a triple knock-out for endogenous ungulate immunoglobulin genes IGHM(−/−), IGHML1(−/−), and IGL(−/−).

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Hantavirus Monongahela-1

<400> SEQUENCE: 1
ctacgactaa agctggaatg agc                                              23

<210> SEQ ID NO 2
<211> LENGTH: 22
<212> TYPE: DNA
<213> ORGANISM: Hantavirus Monongahela-1

<400> SEQUENCE: 2
gagttgttgt tcgtggagag tg                                               22
```